(12) United States Patent
Hood et al.

(10) Patent No.: US 9,714,429 B2
(45) Date of Patent: Jul. 25, 2017

(54) REGULATORY SEQUENCE OF CUPIN FAMILY GENE

(71) Applicant: Arkansas State University, Jonesboro, AR (US)

(72) Inventors: Elizabeth Hood, Jonesboro, AR (US); Thomas Teoh, Jonesboro, AR (US)

(73) Assignee: ARKANSAS STATE UNIVERSITY, State University, AR (US)

( * ) Notice: Subject to any disclaimer, the term of this patent is extended or adjusted under 35 U.S.C. 154(b) by 137 days.

(21) Appl. No.: 14/606,552

(22) Filed: Jan. 27, 2015

(65) Prior Publication Data

US 2015/0211014 A1 Jul. 30, 2015

Related U.S. Application Data

(60) Provisional application No. 61/932,511, filed on Jan. 28, 2014.

(51) Int. Cl.
*C12N 15/82* (2006.01)

(52) U.S. Cl.
CPC .............................. *C12N 15/8234* (2013.01)

(58) Field of Classification Search
None
See application file for complete search history.

(56) References Cited

U.S. PATENT DOCUMENTS

| | | | |
|---|---|---|---|
| 4,654,465 A | 3/1987 | Brar et al. | 800/1 |
| 4,683,195 A | 7/1987 | Mullis et al. | 435/6.11 |
| 4,683,202 A | 7/1987 | Mullis | 435/91.2 |
| 4,684,611 A | 8/1987 | Schilperoort et al. | 435/172.3 |
| 4,727,219 A | 2/1988 | Brar et al. | 800/1 |
| 4,965,188 A | 10/1990 | Mullis et al. | 435/6.12 |
| 5,015,580 A | 5/1991 | Christou et al. | 435/172.3 |
| 5,352,605 A | 10/1994 | Fraley et al. | 435/418 |
| 5,550,318 A | 8/1996 | Adams et al. | 800/205 |
| 5,584,807 A | 12/1996 | McCabe | 604/71 |
| 5,591,616 A | 1/1997 | Hiei et al. | 435/172.3 |
| 5,618,682 A | 4/1997 | Scheirer | 435/8 |
| 5,674,713 A | 10/1997 | McElroy et al. | 435/69.7 |
| 5,859,341 A | 1/1999 | Albertsen et al. | 800/205 |
| 5,976,796 A | 11/1999 | Szalay et al. | 435/6.11 |
| 6,013,859 A | 1/2000 | Fabijanski et al. | 800/274 |
| 6,074,859 A | 6/2000 | Hirokawa et al. | 435/189 |
| 6,252,148 B1 | 6/2001 | Armstrong | 800/320.1 |
| 7,790,873 B2 * | 9/2010 | Duwenig | C12N 15/8234 435/320.1 |

FOREIGN PATENT DOCUMENTS

| | | |
|---|---|---|
| EP | 0342926 A2 | 11/1989 |
| WO | WO/85/01856 | 5/1985 |
| WO | WO/91/19806 | 12/1991 |
| WO | WO/95/14098 | 5/1995 |

OTHER PUBLICATIONS

Saha et al., In Silico Biol 7(1):7-19 (2007).*
Potenza et al., In Vitro Cell Dev Biol Plant 40:1-22 (2004).*
Khuri et al, Mol Biol Evol 18(4):593-605 (2001).*
Dunwell et al., Phytochem 65:7-17 (2004).*
Donald & Cashmore, EMBO J 9:1717-26 (1990).*
Kim et al., Plant Mol Biol 24:105-17 (1994).*
Dolferus et al., Plant Physiol 105:1075-87 (1994).*
Alexandrov, N. N. et al. (2009) "Insights into corn genes derived from large-scale cDNA sequencing," *Plant Molecular Biology* 69(1-2), 179-194.
Anderson, M. L. M. et al. (1985) "Quantitative Filter Hybridization," in *Nucleic Acid Hybridisation: A Practical Approach* (Hames, B. D., et al., Eds.), pp. 73-111, Oxford University Press, USA.
Armstrong, C. et al. (1991) "Development and availability of germplasm with high type II culture formation response," *Maize Genet Coop Newsletter 13*, 92-93.
Armstrong, C. L. et al. (1985) "Establishment and maintenance of friable, embryogenic maize callus and the involvement of L-proline," *Planta* 164(2), 207-214.
Bailey, M. R. et al. (2004) "Improved recovery of active recombinant laccase from maize seed," *Applied Microbiology and Biotechnology* 63(4), 390-397.
Baker, J. et al. (1988) "Sequence and characterization of 6 Lea proteins and their genes from cotton," *Plant Molecular Biology* 13(3), 277-291.
Becker, T. W. et al. (1992) "Thecab-m7 gene: a light-inducible, mesophyll-specific gene of maize," *Plant Molecular Biology* 20(1), 49-60.
Belanger, F. C. et al. (1991) "Molecular basis for allelic polymorphism of the maize Globulin-1 gene," *Genetics* 129(3), 863-872.
Benjamini, Y. et al. (1995) "Controlling the false discovery rate: a practical and powerful approach to multiple testing," *Journal of the Royal Statistical Society. Series B (Methodological)* 57(1), 289-300.
Bowman, V. B. et al. (1988) "Expression of lipid body protein gene during maize seed development. Spatial, temporal, and hormonal regulation," *Journal of Biological Chemistry* 263(3), 1476-1481.
Brinch-Pedersen, H. et al. (2003) "Concerted action of endogenous and heterologous phytase on phytic acid degradation in seed of transgenic wheat (*Triticum aestivum* L.)," *Transgenic Research* 12(6), 649-659.
Broglie, R. et al. (1984) "Light-regulated expression of a pea ribulose-1,5-bisphosphate carboxylase small subunit gene in transformed plant cells," *Science* 224(4651), 838-843.
Bustos, M. M. et al. (1989) "Regulation of beta-glucuronidase expression in transgenic tobacco plants by an A/T-rich, cis-acting sequence found upstream of a French bean beta-phaseolin gene," *Plant Cell and Environment* 1(9), 839-853.
Caddick, M. X. et al. (1998) "An ethanol inducible gene switch for plants used to manipulate carbon metabolism," *Nature Biotechnology* 16(2), 177-180.

(Continued)

*Primary Examiner* — Cathy Kingdon Worley
*Assistant Examiner* — Russell Boggs
(74) *Attorney, Agent, or Firm* — Medlen & Carroll, LLP

(57) ABSTRACT

This invention is in the field of plant biology and agriculture and relates to novel seed specific promoter regions. The present invention further provide methods of producing proteins and other products of interest and methods of controlling expression of nucleic acid sequences of interest using the seed specific promoter regions.

10 Claims, 21 Drawing Sheets

(56) References Cited

OTHER PUBLICATIONS

Carrillo, C. et al. (1998) "Protective immune response to foot-and-mouth disease virus with VP1 expressed in transgenic plants," *Journal of Virology 72*(2), 1688-1690.

Casas, A. M. et al. (1993) "Transgenic sorghum plants via microprojectile bombardment," *Proceedings of the National Academy of Sciences 90*(23), 11212-11216.

Chamberlin, M. et al. (1970) "New RNA Polymerase from *Escherichia coli* infected with Bacteriophage T7," *Nature 228*(5268), 227-231.

Christensen, A. H. et al. (1992) "Maize polyubiquitin genes: structure, thermal perturbation of expression and transcript splicing, and promoter activity following transfer to protoplasts by electroporation," *Plant Molecular Biology 18*(4), 675-689.

Clough, R. C. et al. (2006) "Manganese peroxidase from the white-rot fungus Phanerochaete chrysosporium is enzymatically active and accumulates to high levels in transgenic maize seed," *Plant Biotechnology Journal 4*(1), 53-62.

Coleman, C. E. et al. (2012) "The Maize [gamma]-Zein Sequesters [alpha]-Zein and Stabilizes Its Accumulation in Protein Bodies of Transgenic Tobacco Endosperm," *Plant Cell 13*(12), 2335-2345.

Cornejo, M.-J. et al. (1993) "Activity of a maize ubiquitin promoter in transgenic rice," *Plant Molecular Biology 23*(3), 567-581.

Coruzzi, G. et al. (1984) "Tissue-specific and light-regulated expression of a pea nuclear gene encoding the small subunit of ribulose-1,5-bisphosphate carboxylase," *EMBO Journal 3*(8), 1671-1679.

Creissen, G. et al. (1992) "Molecular characterization of glutathione reductase cDNAs from pea (*Pisum sativum* L.)," *The Plant Journal 2*(1), 129-131.

Crossway, A. et al. (1986) "Integration of foreign DNA following microinjection of tobacco mesophyll protoplasts," *Molecular Genetics and Genomics 202*, 179-185.

Daniell, H. et al. (2001) "Medical molecular farming: production of antibodies, biopharmaceuticals and edible vaccines in plants," *Trends in Plant Science 6*(5), 219-226.

Davidson, R. M. et al. (2011) "Utility of RNA Sequencing for Analysis of Maize Reproductive Transcriptomes," *Plant Genetics 13*(3), 191-203.

De Wet, J. R. et al. (1987) "Firefly luciferase gene: structure and expression in mammalian cells," *Molecular and Cellular Biology 7*(2), 725-737.

De Wilde, C. et al. (2000) "Plants as bioreactors for protein production: avoiding the problem of transgene silencing," *Plant Molecular Biology 43*(2-3), 347-359.

Della-Cioppa, G. et al. (1987) "Protein trafficking in plant cells," *Plant Physiology 84*(4), 965-968.

Dure, L. et al. (1989) "Common amino acid sequence domains among the LEA proteins of higher plants," *Plant Molecular Biology 13*(5), 475-486.

Elroy-Stein, O. et al. (1989) "Cap-independent translation of mRNA conferred by encephalomyocarditis virus 5' sequence improves the performance of the vaccinia virus/bacteriophage T7 hybrid expression system," *Proceedings of the National Academy of Sciences 86*(16), 6126-6130.

Erlich, H. A., (Ed.) (1989) *PCR Technology: Principles and Applications for DNA Amplcation,* Stockton Press, New York.

Estruch, J. J. et al. (1997) "Transgenic plants: An emerging approach to pest control," *Nature Biotechnology 15*(2), 137-141.

Fontes, E. B. et al. (1991) "Characterization of an immunoglobulin binding protein homolog in the maize floury-2 endosperm mutant," *Plant Cell and Environment 3*(5), 483-496.

Fraley, R. T. et al. (1983) "Expression of bacterial genes in plant cells," *Proceedings of the National Academy of Sciences 80*(15), 4803-4807.

Fromm, M. et al. (1985) "Expression of genes transferred into monocot and dicot plant cells by electroporation," *Proceedings of the National Academy of Sciences 82*(17), 5824-5828.

Gallie, D. R. et al. (1995) "The tobacco etch viral 5' leader and poly(A) tail are functionally synergistic regulators of translation," *Gene 165*(2), 233-238.

Garbarino, J. E. et al. (1994) "Isolation of a ubiquitin-ribosomal protein gene (ubi3) from potato and expression of its promoter in transgenic plants," *Plant Molecular Biology 24*(1), 119-127.

Geffers, R. et al. (2000) "Anaerobiosis-specific interaction of tobacco nuclear factors with cis-regulatory sequences in the maize GapC4 promoter," *Plant Molecular Biology 43*(1), 11-21.

Gideon, G. et al. (1995) "Endoreduplication in Maize Endosperm: Involvement of M Phase-Promoting Factor Inhibition and Induction of S Phase-Related Kinases," *Science 269*(5228), 1262-1264.

Girke, T. et al. (2000) "Microarray analysis of developing Arabidopsis seeds," *Plant Physiology 124*(4), 1570-1581.

Gordon-Kamm, W. et al. (1990) "Transformation of Maize Cells and Regeneration of Fertile Transgenic Plants," *Plant Cell 2*(7), 603-618.

Gould, S. J. et al. (1989) "A conserved tripeptide sorts proteins to peroxisomes," *Journal of Cell Biology 108*(5), 1657-1664.

Graham, F. L. et al. (1973) "A new technique for the assay of infectivity of human adenovirus 5 DNA," *Virology 52*(2), 456-467.

Grdzelishvili, V. Z. et al. (2000) "Mapping of the Tobacco mosaic virus movement protein and coat protein subgenomic RNA promoters in vivo," *Virology 275*(1), 177-192.

Gruber. (1993) "Vectors for plant transformation," in *Methods in Plant Molecular Biology and Biotechnology,* pp. 89-119, CRC Press.

Guilley, H. et al. (1982) "Transcription of cauliflower mosaic virus DNA: detection of promoter sequences, and characterization of transcripts," *Cell 30*(3), 763-773.

Gurley, W. B. et al. (1986) "Upstream sequences required for efficient expression of a soybean heat shock gene," *Molecular and Cellular Biology 6*(2), 559-565.

Haq, T. A. et al. (1995) "Oral immunization with a recombinant bacterial antigen produced in transgenic plants," *Science 268*(5211), 714-716.

Hayano-Kanashiro, C. et al. (2009) "Analysis of gene expression and physiological responses in three Mexican maize landraces under drought stress and recovery irrigation," *PLoS ONE 4*(10), e7531.

Herman, E. M. et al. (1999) "Protein storage bodies and vacuoles," *Plant Cell 11*(4), 601-614.

Hiei, Y. et al. (1994) "Efficient transformation of rice (*Oryza sativa* L.) mediated by Agrobacterium and sequence analysis of the boundaries of the T-DNA," *The Plant Journal 6*(2), 271-282.

Hood, E. E. et al. (2003) "Criteria for high-level expression of a fungal laccase gene in transgenic maize," *Plant Biotechnology Journal 1*(2), 129-140.

Hood, E. E. et al. (2012) "Manipulating corn germplasm to increase recombinant protein accumulation," *Plant Biotechnology Journal 10*(1), 20-30.

Hood, E. E. et al. (1986) "The hypervirulence of Agrobacterium tumefaciens A281 is encoded in a region of pTiBo542 outside of T-DNA," *Journal of Bacteriology 168*(3), 1291-1301.

Hood, E. E. et al. (2007) "Subcellular targeting is a key condition for high-level accumulation of cellulase protein in transgenic maize seed," *Plant Biotechnology Journal 5*(6), 709-719.

Hood, E. E. et al. (1997) "Commercial production of avidin from transgenic maize: characterization of transformant, production, processing, extraction and purification," *Molecular Breeding 3,* 291-306.

Hood, E. E. et al. (2002) "Monoclonal antibody manufacturing in transgenic plants—myths and realities," *Current Opinion in Biotechnology 13*(6), 630-635.

Innis, M. et al. (1995) *PCR Strategies,* Academic Press, New York.

Innis, M. et al. (1999) *PCR Applications: Protocols for Functional Genomics,* Academic Press, New York.

Innis, M. A. et al. (1990) *PCR Protocols: A guide to methods and applications,* Academic Press, New York.

Ishida, Y. et al. (1996) "High efficiency transformation of maize (*Zea mays* L.) mediated by Agrobacterium tumefaciens," *Nature Biotechnology 14*(6), 745-750.

(56) References Cited

OTHER PUBLICATIONS

Jefferson, R. A. et al. (1987) "GUS fusions: beta-glucuronidase as a sensitive and versatile gene fusion marker in higher plants," *EMBO Journal* 6(13), 3901-3907.
Jobling, S. A. et al. (1987) "Enhanced translation of chimaeric messenger RNAs containing a plant viral untranslated leader sequence," *Nature* 325(6105), 622-625.
Kacian, D. L. et al. (1972) "A Replicating RNA Molecule Suitable for a Detailed Analysis of Extracellular Evolution and Replication," *Proceedings of the National Academy of Sciences of the United States of America* 69(10), 3038-3042.
Kader, J. C. (1990) "Intracellular transfer of phospholipids, galactolipids, and fatty acids in plant cells," *Sub-Cellular Biochemistry* 16, 69-111.
Kalderon, D. et al. (1984) "A short amino acid sequence able to specify nuclear location," *Cell* 39(3), 499-509.
Klein, T. M. et al. (1992) "Transformation of microbes, plants and animals by particle bombardment," *Nature Biotechnology* 10(3), 286-291.
Kowles, R. V. et al. (1985) "DNA amplification patterns in maize endosperm nuclei during kernel development," *Proceedings of the National Academy of Sciences* 82(20), 7010-7014.
Kriz, A. (1989) "Characterization of embryo globulins encoded by the maizeGlb genes," *Biochemical Genetics* 27(3-4), 239-251.
Lamphear, B. J. et al. (2002) "Delivery of subunit vaccines in maize seed," *Journal of Controlled Release* 85(1-3), 169-180.
Lee, J.-M. et al. (2002) "DNA array profiling of gene expression changes during maize embryo development," *Functional & Integrative Genomics* 2(1-2), 13-27.
Lee, N. et al. (1991) "Efficient transformation and regeneration of rice small cell groups," *Proceedings of the National Academy of Sciences* 88(15), 6389-6393.
Lessard, P. A. et al. (2002) "Manipulating gene expression for the metabolic engineering of plants," *Metabolic Engineering* 4(1), 67-79.
Leung, J. et al. (1991) "Functional analysis of cis-elements, auxin response and early developmental profiles of the mannopine synthase bidirectional promoter," *Molecular and General Genetics* 230(3), 463-474.
Li, P. et al. (2010) "The developmental dynamics of the maize leaf transcriptome," *Nature Genetics* 42(12), 1060-1067.
Lommel, S. A. et al. (1991) "Identification of the Maize chlorotic mottle virus capsid protein cistron and characterization of its subgenomic messenger RNA," *Virology* 181(1), 382-385.
Luo, M. et al. (2008) "Characterization of gene expression profiles in developing kernels of maize (Zea mays) inbred Tex6," *Plant Breeding* 13(6), 569-578.
Macejak, D. G. et al. (1991) "Internal initiation of translation mediated by the 5' leader of a cellular mRNA," *Nature* 353(6339), 90-94.
Maiti, I. B. et al. (1997) "Promoter/leader deletion analysis and plant expression vectors with the figwort mosaic virus (FMV) full length transcript (FLt) promoter containing single or double enhancer domains," *Transgenic Research* 6(2), 143-156.
Maniatis, T. et al. (1987) "Regulation of inducible and tissue-specific gene expression," *Science* 236(4806), 1237-1245.
Mason, H. S. et al. (1992) "Expression of hepatitis B surface antigen in transgenic plants," *Proceedings of the National Academy of Sciences* 89(24), 11745-11749.
Mathur, J. et al. (1998) "PEG-Mediated Protoplast Transformation with Naked DNA," in *Arabidopsis Protocols* (Martinez-Zapater, J., et al., Eds.), pp. 267-276, Humana Press.
Matsuoka, K. et al. (1991) "Propeptide of a precursor to a plant vacuolar protein required for vacuolar targeting," *Proceedings of the National Academy of Sciences* 88(3), 834-838.
McCarty, D. R. (1995) "Genetic control and integration of maturation and germination pathways in seed development," *Annual Review of Plant Physiology and Plant Molecular Biology* 13, 71-93.
Meinkoth, J. et al. (1984) "Hybridization of nucleic acids immobilized on solid supports," *Analytical Biochemistry* 138(2), 267-284.

Miki, B. et al. (2004) "Selectable marker genes in transgenic plants: applications, alternatives and biosafety," *Journal of Biotechnology* 107(3), 193-232.
Moloney, M. M. et al. (1989) "High efficiency transformation of Brassica napus using Agrobacterium vectors," *Plant Cell Reports* 8(4), 238-242.
Mortazavi, A. et al. (2008) "Mapping and quantifying mammalian transcriptomes by RNA-Seq," *Nature Methods* 5(7), 621-628.
Nakashima, K. et al. (2006) "Transcriptional regulation of ABI3- and ABA-responsive genes including RD29B and RD29A in seeds, germinating embryos, and seedlings of Arabidopsis," *Plant Molecular Biology* 60(1), 51-68.
Needleman, S. B. et al. (1970) "A general method applicable to the search for similarities in the amino acid sequence of two proteins," *Journal of Molecular Biology* 48(3), 443-453.
Nessler, C. L. (1994) "Metabolic engineering of plant secondary products," *Transgenic Research* 3(2), 109-115.
Odell, J. T. et al. (1985) "Identification of DNA sequences required for activity of the cauliflower mosaic virus 35S promoter," *Nature* 313(6005), 810-812.
Ohlrogge, J. et al. (1995) "Lipid biosynthesis," *Plant Cell* 7(7), 957-970.
Oldach, K. H. et al. (2001) "Heterologous expression of genes mediating enhanced fungal resistance in transgenic wheat," *Molecular Plant-Microbe Interactions* 14(7), 832-838.
Pearson, W. R. et al. (1988) "Improved tools for biological sequence comparison," *Proceedings of the National Academy of Sciences* 85(8), 2444-2448.
Pla, M. et al. (1991) "Regulation of the abscisic acid-responsive gene rab28 in maize viviparous mutants," *Molecular and General Genetics MGG* 230(3), 394-400.
Poirier, Y. et al. (1995) "Production of polyhydroxyalkanoates, a family of biodegradable plastics and elastomers, in bacteria and plants," *Nature Biotechnology* 13(2), 142-150.
Robinson, M. D. et al. (2010) "A scaling normalization method for differential expression analysis of RNA-seq data," *Genome Biology* 11(3), R25.
Rogers, J. C. (1985) "Two barley alpha-amylase gene families are regulated differently in aleurone cells," *Journal of Biological Chemistry* 260(6), 3731-3738.
Roussell, D. L. et al. (1988) "Deletion of DNA sequences flanking an $M_r$ 19 000 zein gene reduces its transcriptional activity in heterologous plant tissues," *Molecular and General Genetics MGG* 211(2), 202-209.
Russell, D. A. et al. (1997) "Tissue-specific expression in transgenic maize of four endosperm promoters from maize and rice," *Transgenic Research* 6(2), 157-168.
Sambrook, J. et al. (1989) "Transfer and Fixation of Denatured RNA to Membranes," in *Molecular Cloning: A Laboratory Manual* (Sambrook, J., et al., Eds.) 2nd ed., pp. 7.39-7.52, Cold Spring Harbor Laboratory Press, New York.
Sambrook, J. et al. (1989) "Synthesis of Single-stranded RNA Proves by In Vitro Transcription," In *Molecular Cloning: A Laboratory Manual* (Sambrook, J., et al., Eds.) 2nd ed., pp. 9.31-9.58, Cold Spring Harbor Laboratory Press, New York.
Sambrook, J. et al. (1989) in *Molecular Cloning: A Laboratory Manual* (Sambrook, J., et al., Eds.) 2nd ed., pp. 16.07-16.08, Cold Spring Harbor Laboratory Press, New York.
Smith, T. F. et al. (1981) "Comparison of biosequences," *Advances in Applied Mathematics* 2(4), 482-489.
Stiefel, V. et al. (1990) "Expression of a maize cell wall hydroxyproline-rich glycoprotein gene in early leaf and root vascular differentiation," *Plant Cell* 2(8), 785-793.
Streatfield, S. et al. (2002) "Development of an edible subunit vaccine in corn against enterotoxigenic strains of Escherichia coli," *In Vitro Cellular & Developmental Biology Plant* 13(1), 11-17.
Streatfield, S. J. et al. (2001) "Plant-based vaccines: unique advantages," *Vaccine* 19(17-19), 2742-2748.
Takimoto, I. et al. (1994) "Non-systemic expression of a stress-responsive maize polyubiquitin gene (Ubi-1) in transgenic rice plants," *Plant Molecular Biology* 26(3), 1007-1012.

(56) References Cited

OTHER PUBLICATIONS

Thimm, O. et al. (2004) "MAPMAN: a user-driven tool to display genomics data sets onto diagrams of metabolic pathways and other biological processes," *The Plant Journal* 37(6), 914-939.
Thomann, E. B. et al. (1992) "Accumulation of Group 3 Late Embryogenesis Abundant Proteins in *Zea mays* Embryos: Roles of Abscisic Acid and the Viviparous-1 Gene Product," *Plant Physiology* 99(2), 607-614.
Thorvaldsdóttir, H. et al. (2013) "Integrative Genomics Viewer (IGV): high-performance genomics data visualization and exploration," *Briefings in Bioinformatics* 14(2), 178-192.
Usadel, B. et al. (2009) "A guide to using MapMan to visualize and compare Omics data in plants: a case study in the crop species, Maize," *Plant, Cell & Environment* 32(9), 1211-1229.
Velten, J. et al. (1985) "Selection-expression plasmid vectors for use in genetic transformation of higher plants," *Nucleic Acids Research* 13(19), 6981-6998.
Vernoud, V. et al. (2005) "Maize Embryogenesis," *Maydica* 13.
Vilardell, J. et al. (1991) "Regulation of the maizerab17 gene promoter in transgenic heterologous systems," *Plant Molecular Biology* 17(5), 985-993.
Voss, S. D. et al. (1986) "The role of enhancers in the regulation of cell-type-specific transcriptional control," *Trends in Biochemical Sciences* 11(7), 287-289.
Wan, Y. et al. (1994) "Generation of Large Numbers of Independently Transformed Fertile Barley Plants," *Plant Physiology* 104(1), 37-48.
Waterhouse, P. M. et al. (2001) "Gene silencing as an adaptive defence against viruses," *Nature* 411(6839), 834-842.
Weigel, D. et al. (1995) "A developmental switch sufficient for flower initiation in diverse plants," *Nature* 377(6549), 495-500.
Weising, K. et al. (1988) "Foreign Genes in Plants: Transfer, Structure, Expression, and Applications," *Annual Review of Genetics* 22, 421-477.
Wilcoxon, F. (1945) "Individual Comparisons by Ranking Methods," *Biometrics Bulletin* 1(6), 80-83.
Wohlleben, W. et al. (1988) "Nucleotide sequence of the phosphinothricin N-acetyltransferase gene from *Streptomyces viridochromogenes* Tu494 and its expression in *Nicotiana tabacum*," *Gene* 70(1), 25-37.
Woo, Y. M. et al. (2001) "Genomics analysis of genes expressed in maize endosperm identifies novel seed proteins and clarifies patterns of zein gene expression," *Plant Cell* 13(10), 2297-2317.
Woodard, S. L. et al. (2003) "Maize (*Zea mays*)-derived bovine trypsin: characterization of the first large-scale, commercial protein product from transgenic plants," *Biotechnology and Applied Biochemistry* 38(Pt 2), 123-130.
Wu, D. Y. et al. (1989) "The ligation amplification reaction (LAR)—Amplification of specific DNA sequences using sequential rounds of template-dependent ligation," *Genomics* 4(4), 560-569.
Wu, T. D. et al. (2010) "Fast and SNP-tolerant detection of complex variants and splicing in short reads," *Bioinformatics* 26(7), 873-881.
Yang, N. S. et al. (1990) "Maize sucrose synthase-1 promoter directs phloem cell-specific expression of Gus gene in transgenic tobacco plants," *Proceedings of the National Academy of Sciences* 87(11), 4144-4148.
Ye, X. et al. (2000) "Engineering the Provitamin A (β-Carotene) Biosynthetic Pathway into (Carotenoid-Free) Rice Endosperm," *Science* 287(5451), 303-305.
Yu, H. et al. (2003) "Post-transcriptional gene silencing in plants by RNA," *Plant Cell Reports* 22(3), 167-174.
Zeeberg, B. R. et al. (2005) "High-Throughput GoMiner, an 'industrial-strength' integrative gene ontology tool for interpretation of multiple-microarray experiments, with application to studies of Common Variable Immune Deficiency (CVID)," *BMC Bioinformatics* 6, 168.
Zhang, L. et al. (2009) "A genome-wide characterization of microRNA genes in maize," *PLoS Genetics* 5(11), e1000716.
Zhong, G.-Y. et al. (1999) "Commercial production of aprotinin in transgenic maize seeds," *Molecular Breeding* 5, 345-356.

\* cited by examiner

FIGURE 17

Sequence upstream of the unclassified gene GRMZM2G078441 [SEQ ID NO: 1]:
GATATGTCCTACTCCTTGACATGCCTGCGCGGTGGGGGAGGAAAGTAGGTCTTCAGGCTGAAGTT
TGTAATTTGATGGTTTGTTGGTTATCGGCTAACTGTTTTACGCTTGCTCTAAAATTAGTCGTTTA
AATTAAAAAACTAAACTTAGAAAAAAAAATTAAGTAAAATATATCAAGTTAAGTACCAAATTAAA
CATTCTCTCAATTAATCTCAAATGGTAGATTTTTCTGTTCAGTCGCGGTATAAAACCGTATTTTT
TAAGACTTTTACTTATTTCTATCTCTGCTGATTATGGTATTAAGATCCCTACTAAGTGTCCAATA
CTTTCATTAACTTATTACCAAAATAAAGTATTATAGGTATTAGAAATCCTCTTAGAGTCTAATA
CTGTCTCCGCTCTAAAATATAGTTGTTTCTAGTCCATTTTATTATATCTATATTTATTCAAATG
ATAATGAATTTATATATATATATATATATATATATATATATATATATATATATATATATATAT
ATATATATATATATATATATATATATAACGGGAGCCCTGGGCTTCCAATAGTTAAAGGAAA
CACAGGCCGACCATCCCTGCAAACTGGTTCAACCAGCGCGTCCAAACAGGCGGTCGGGTGCGCCA
CCTGCCCCACGTCTGTTAGCGCAAAAAAAGGAATGCATGCATAAGTCAAACACGATCCAATGCAT
GCGCATAAATTTAGGAAAGATATGTGCGGCAGTTTCTATTTTAAAATCCTTTATTTCCTCCATA
AATTTAGGATCGCTGCAACAGCCATGCAGCTAGACGCGTAAGGACCATTTTATGATATATACTGA
GACTAAATATGCTACACTGTGTTAATAATTATGCAATTCGATATACTGCGTAAAAATCTGTTACC
AGCTGCATGCACACGAATTTATGATAAAAATGTGCAATGAAAGGAAATGAATTACACGCATAGA
AACAAAAAATCGTATTTAATGTTTTATTTCCTTCATAAATATAAGGTCCCTCCAACAGCCATGCA
GCTAAAACACATTAAATCTAGTTTATGACATATACTGATACAAATTATACTACATGGTGTAGGTA
TTTATGCAATTCGTTACACTGCGTAAAAAATCTGGCATGTTGTTCACTGGTGGATGCACCTCCGG
GTTGGAGCGTAATAACCTTAAGTTTTAAGCATAAAATCCCTCAATTATAAGTGTATATACCGAGC
CAATGTGAGAGGTTGATAGCTCTAGTAGGTTGTTATTACGATCCTATTTTATGGCAGATCCGAA
AAATATGGCAGTCGCATGCATGCGGTTATACAGATCCTAAAATTATGGCAAAATGCATGCATGAG
TCAAACACGTTCCCTTGCATGCGCGTAAATTTAGGAAAGATATGTGTGGCGGTTTCTATTTTAAA
TGCTTTATTTCCTCCATAAATTTAGGATCGCTGCAACAGACATGCAACTAAAACTCGTAATGACC
ATTTTATGCTATATACTGATACTAAATATGCTACACTGTGTAGATAATTATGCAATTCGGTATAC
TGCGTAAAAATCTGCTACAGGCTGCATGCACACGAATTTATGATGGAAAGAATATGCAATGAAAG
GAAATGAATTGCATGCATAGAAACAAAAATCATATTTAATATTTTAATTTTGCTTCCTAAATAT
AGGATCCCTCCAACAGCCATGCAAATATAACGCATTAGAACTAGTTTATGATGTATACTGAAACA
AATTATAATACACGGTGTAGGTATTTATGCAATTCCTTACAAAGCGTAAAAAATCTGGCATGTTG
TTCACTGGTGGACGCATCTCCGGGTGGAGCGTAAAAACCTTAAGTTTTGAGCATAAAATCCCTCA
ATTATAAGCATAAATACCGAGTCAATTAGAGGTTGATAGCTTTAGTAGGTTGTTATTACGATCCT
ATTTTTATGACAGATCCGAAAAACATGGCAGCCGCATGCATGCGGTTTCTGTCGGGGACCATAAT
TAGGGGTACCCTCAAGACGCCTAATTCTCAGCTGGTAACCCCATCAGCATAAAGCTGCAGAGGC FIGURE 17 (continued)

```
CTGATGGGTGCGATTAAGTCAGGGATCAGTCCATACGAGCGACTCGATCACGCCTCGCCCGAGCC
TAGCCTCGGGCAAGGGCAGCCGACCCCGAGGGGTTTCCGTCTCGCCCGAGGCCCCCTTTTTAAC
GGCGGACACATCTCCGGCTCGCCCGAGGCCTTGGCTTCGCTAAGAAGCAACCCTGACTAAATCGC
CGCGCCGACCGACCGAGTCGCAGGGGCATTTAACGCAAAGGTGGCCTGACACCTTTATCCTGACA
CGCGCCCTCCGGCAGAGCCGAAGTGACCGCCGTCACTTCGCCGCTCCACTGACTGGTCTGACAGA
AGGACAGCGCCGCCTGCGCCACTCCGACTGCAGCGCCACTTGACAGAGTGATGCTGACAGGAAGC
CAGGCCTTGCCAAAGGCGCCATAGGAAGCTCCGCCCGACCCAGGGCTCGGACTCGGGCTAAGCCT
CGGAAGACGGCGAACTCCGCTCCGCCCGACCCAGGGCTCGGACTCGGGCTAAGCCCCGGAAGACG
GCGAACTCCGCTCCGCCCGACCCAGGGCTCGCACTCGGGCTAAGGCCCCGGAAGACGGCGAACTC
CGCTCCGCCCGACCCAGGGCTCGGACTCGGGCTAAGGCCCCGGAAGACGGCGAACTCCGCTCCGC
CCGACCCAGGGCTCGGACTCAGGCTAAGGCCCCGGAAGACGGCGAACTCCACTCCGCCCGACCCA
GGGCTCGGACTCGGGCTCAGCCCCAGAAGACGACGAACTCCGCTCCGCCCGACCCCAGGGCTCGG
ACTCGGGCTAAGACCCGGAAGACGACGAACTCCGCTTCGCCCGACCCCAGGGCTCGGACTCCGCC
CGGGCCTCTGCCGAACGATCTCCGCCTTGCCCGACCCGGGGGCTCGGCCTCGGCCTCGGCCACGG
AAGACAGACTCGACCCTGGCTTCGGAGGAGCCCCACGTCGCCCGACCTAGGGCACAGGCCCGCC
ACGTCAACAGGAAGCGCCA
```

FIGURE 18

GRMZM2G078441 gene sequence [SEQ ID NO: 2]:

ATGGCGGTGGCGACGACTGCTCGGTGGCTCCTGCTCCTGGCTGTCGTCTCGGCGGCCGCGGCGTC
CGGGAAGCACGAGAGGTGGAGGGTGGGCGGCCAGGTGGTGGAGAAGGAGCGACGGCGGGTGGTGG
CGGAGAGCGAGGCCGGCTCGGTCTCGGCCGTGGACGTCGCCGACGCGGCGGGCACGGCGTACCGG
CTGCACTTCATCACCATGGACCCCGGGGCGCTGTTCCTGCCCGTGCAGCTGCATGCCGACATGGT
GTTCTACGTTCACAGCGGGCGGGGCAAGGTGACTTCCATAGAAGAAGAGAGCAGCGAACAGAGCT
CCCTGGAGGTGGAGCGAGGAGACGTATACAACTTTGAGCAGGGGAGCATCCTGTACATCCAGAGC
TACCCCAACGCCAGTAGACAGCGTCTTCGGATCTACGCCATCTTCACCAGCGAAGGCATCAACGC
CGATGACCCCTCGAAGCCCAAGGTGGAAGCTTACTCCAGCGTCAGCAATCTGGTCAAAGGGTTCG
AGACAGACGTTCTTCGCCTGGGATTTGGGGTCAAACCCGAGGTGGTAGAAGCGATCAAGTCTGCC
AAGACACCGCCACCGATCATAGCCTACAACCCAGAGGAGGAGAAGGGGGACAAGAAACCCGGCTG
GACCGAGAACATCATCGACGCTCTGCTGGGCGTGCGCGATCCGGAGGAGTTCCTTAACAAGAAGA
AGAAGAAGAAGGACAAGCACAAGGACAAGAAGTCCAAGAGCAAGGCGTTCAACTTCTACTCCGGA
AAGCCAGACGTCCAGAACTGCTACGGGTGGAGCCGGATGATGACTAGCAAGGACCTCGACGCGCT
GCACGGATCCAGCATTGGCATGTTCATGGTGAACCTGACTACGGGTTCGATGATGGGGCCTCACT
GGAACCCCAAGGCCACGGAGATCGCCATCGTGACAGAGGGTTCAGGAATCGTGCAGACGGTGTGC
CCGAGCAGCAGCAGCAGCAGCAGCAGCCCGTCGGGCGGGAGCAGTGGAGACCACCACCACGGTCA
CAAGCGGCGCGGCGGGCCGGGAGGCCGCGGCGATGAGGGCGAAGGCGAAGGCGGCCGCGCGCGGT
GGCAGTGCAGGAACTCGGTGTTCCGTGTGAAGGAAGGCGACGTCTTCGTGGTGCCGCGGTTCCAC
CCGATGGCGCAGATGTCGTTCAACGACGACTCGTTCGTGTTCGTCGGGTTCAGCACCCACATGGG
GCAAAACCACCCGCAGTTCCTGGCCGGGAAGGGCTCCGTGCTGCAGGCCATTGGGAAGAAGGTGC
TGGCGCTGGCGCTGGGGCAGCGGGACCCGACCGCCGTGGACAAGCTGCTGTCCGCGCAGCGCGAG
TCGACGATACTGCCGTGCGTATCGTGCGCTGAGGAGCTGGCGGAGAAGGCCGAGGAGGAGAGGAA
GCGACGGGAGGAGGAAGGGGGAGGGAAAGGGAAGGACCGGGAGAACGTGAGAAGGAAAAGGAGA
GGAGGGAACGGGAGGAGAAGGAAAAGGAGGAAGAGCGGGAGAGGGAACGGGAGGAAAAGGAGAGG
AAGGAAAGGGAACGGGAGGAAAAGGAGAGGAAGGAAAGGGAACGGGAGGAAGAAGAGAGGAGGGA
AGAGGAAGAAGAGCGGGCCAGGAAGGAGCAAGAGAAGCAGCGGAGGAGAGAGAAAGAGGAGGAGG
AGCGTGCACGGAGACGCGAGGAGGAAGAAAGAGAGGGAGGAGGAAGAAGAACGGCGGAGGGAG
GAGGAAGAAGGTGGAGGCGGACGTGGTGACGAGCCAGAGAGGGAGGAAGAAGGCGGTGACAAGCC
GCCATACCGGTTGTCCAAGAAACTGAAGAAACGCTACCATGCACGTGCCGGTGTGTTCAGCAGGA
GTGGCTGA

FIGURE 19

Shortened sequence upstream of the unclassified gene GRMZM2G078441 [SEQ ID NO: 3]:
GATATGTCCTACTCCTTGACATGCCTGCGCGGTGGGGGAGGAAAGTAGGTCTTCAGGCTGAAGTT
TGTAATTTGATGGTTTGTTGGTTATCGGCTAACTGTTTACGCTTGCTCTAAAATTAGTCGTTTA
AATTAAAAAACTAAACTTAGAAAAAAAATTAAGTAAAATATATCAAGTTAAGTACCAAATTAAA
CATTCTCTCAATTAATCTCAAATGGTAGATTTTCTGTTCAGTCGCGGTATAAAACCGTATTTTT
TAAGACTTTTACTTATTTCTATCTCTGCTGATTATGGTATTAAGATCCCTACTAAGTGTCCAATA
CTTTCATTAACTTATTACCAAAAATAAAGTATTATAGGTATTAGAAATCCTCTTAGAGTCTAATA
CTGTCTCCGCTCTAAAATATAGTTGTTTCTAGTCCATTTTATTATATCTATATTTATTCAAATG
ATAATGAATTTATATATATATATATATATATATATATATATATATATATATATATATATATAT
ATATATATATATATATATATATATATATAACGGGAGCCCTGGGCTTCCAATAGTTAAAGGAAA
CACAGGCCGACCATCCCTGCAAACTGGTTCAACCAGCGCGTCCAAACAGGCGGTCGGGTGCGCCA
CCTGCCCCACGTCTGTTAGCGCAAAAAAAGGAATGCATGCATAAGTCAAACACGATCCAATGCAT
GCGCATAAATTTAGGAAAGATATGTGCGGCAGTTTCTATTTTTAAAATCCTTTATTTCCTCCATA
AATTTAGGATCGCTGCAACAGCCATGCAGCTAGACGCGTAAGGACCATTTTATGATATATACTGA
GACTAAATATGCTACACTGTGTTAATAATTATGCAATTCGATATACTGCGTAAAAATCTGTTACC
AGCTGCATGCACACGAATTTATGATAAAAATGTGCAATGAAAGGAAATGAATTACACGCATAGA
AACAAAAAATCGTATTTAATGTTTTATTTCCTTCATAAATATAAGGTCCCTCCAACAGCCATGCA
GCTAAAACACATTAAATCTAGTTTATGACATATACTGATACAAATTATACTACATGGTGTAGGTA
TTTATGCAATTCGTTACACTGCGTAAAAAATCTGGCATGTTGTTCACTGGTGGATGCACCTCCGG
GTTGGAGCGTAATAACCTTAAGTTTTAAGCATAAAATCCCTCAATTATAAGTGTATATACCGAGC
CAATGTGAGAGGTTGATAGCTCTAGTAGGTTGTTATTACGATCCTATTTTATGGCAGATCCGAA
AAATATGGCAGTCGCATGCATGCGGTTATACAGATCCTAAAATTATGGCAAAATGCATGCATGAG
TCAAACACGTTCCCTTGCATGCGCGTAAATTTAGGAAAGATATGTGTGGCGGTTTCTATTTTAAA
TGCTTTATTTCCTCCATAAATTTAGGATCGCTGCAACAGACATGCAACTAAAACTCGTAATGACC
ATTTTATGCTATATACTGATACTAAATATGCTACACTGTGTAGATAATTATGCAATTCGGTATAC
TGCGTAAAAATCTGCTACAGGCTGCATGCACACGAATTTATGATGGAAAGAATATGCAATGAAAG
GAAATGAATTGCATGCATAGAAACAAAAATCATATTTAATATTTAATTTGCTTCCTAAATAT
AGGATCCCTCCAACAGCCATGCAAATATAACGCATTAGAACTAGTTTATGATGTATACTGAAACA
AATTATAATACACGGTGTAGGTATTTATGCAATTCCTTACAAAGCGTAAAAATCTGGCATGTTG
TTCACTGGTGGACGCATCTCCGGGTGGAGCGTAAAACCTTAAGTTTTGAGCATAAAATCCCTCA
ATTATAAGCATAAATACCGAGTCAATTAGAGGTTGATAGCTTTAGTAGGTTGTTATTACGATCCT
ATTTTTATGACAGATCCGAAAACATGGCAGCCGCATGCATGCGGTTTCTGTCGGGGACCATAAT
TAGGGGTACCCTCAAGACGCCTAATTCTCAGCTGGTAACCCCATCAGCATAAAGCTGCAGAGGC

FIGURE 19 (continued)

```
CTGATGGGTGCGATTAAGTCAGGGATCAGTCCATACGAGCGACTCGATCACGCCTCGCCCGAGCC
TAGCCTCGGGCAAGGGCAGCCGACCCCGAGGGGTTTCCGTCTCGCCCGAGGCCCCCTTTTTAAC
GGCGGACACATCTCCGGCTCGCCCGAGGCCTTGGCTTCGCTAAGAAGCAACCCTGACTAAATCGC
CGCGCCGACCGACCGAGTCGCAGGGGCATTTAACGCAAAGGTGGCCTGACACCTTTATCCTGACA
CGCGCCCTCCGGCAGAGCCGAAGTGACCGCCGTCACTTCGCCGCTCCACTGACTGGTCTGACAGA
AGGACAGCGCCGCCTGCGCCACTCCGACTGCAGCGCCACTTGACAGAGTGATGCTGACAGGAAGC
CAGGCCTTGCCAAAGGCGCCATAGGAAGCT
```

REGULATORY SEQUENCE OF CUPIN FAMILY GENE

CROSS-REFERENCE TO RELATED APPLICATIONS

The present application claims the benefit of U.S. Provisional Patent Application No. 61/932,511, filed on Jan. 28, 2014, which is incorporated herein by reference.

STATEMENT OF GOVERNMENTAL SUPPORT

The invention was made with government support awarded by the National Science Foundation (EPS-730 0701890) and (EPS-1003970), by the Department of Energy EERE (DE FG36 G088025), and by the USDA NIFA (2012-70001-20163). The government has certain rights in the invention.

A Sequence Listing has been submitted in an ASCII text file named "17929gtk.txt", created on Feb. 19, 2015, consisting of 15,448 bytes, the entire content of which is herein incorporated by reference.

FIELD OF THE INVENTION

This invention is in the field of plant biology and agriculture and relates to novel seed specific promoter regions. The present invention further provides methods of producing proteins and other products of interest and methods of controlling expression of nucleic acid sequences of interest using the seed specific promoter regions.

BACKGROUND OF THE INVENTION

Promoters are vital molecular tools that have been applied widely in plant biotechnology to control the expression of introduced genes. There are many applications for promoters in driving gene expression in plant tissues. These include the synthesis of scoreable and selectable markers to identify transgenic plants (Jefferson et al., 1987 [1]; Wohlleben et al., 1988 [2]) and the over-expression of control point enzymes to modify metabolic flux through key pathways, so affecting the yields of important plant products (Nessler, 1994 [3]; Lessard et al., 2002 [4]). Other uses of plant promoters include the expression of genes conferring resistance to pests, thus conferring protection (Estruch et al., 1997 [5]), and the expression of non-native enzymes to facilitate the production of foreign metabolites in particular plant species (Poirier et al., 1995 [6]; Ye et al., 2000 [7]). A further application of plant promoters is to over-express controlling regulatory genes affecting aspects of plant physiology such as flowering time and so modify plant growth characteristics (Weigel and Nilsson, 1995 [8]). Promoters are also used to repress the expression of specific genes by driving the synthesis of interfering RNA species (Waterhouse et al., 2001 [9]), thus affecting plant metabolic and developmental pathways (Yu and Kumar, 2003 [10]). Although high levels of expression may not be necessary for all of the above applications, there is clearly a need for promoters showing activity in plant tissues.

Apart from these and other applications of promoters to modify plant traits, promoters are also required for plants to act as production systems for heterologous proteins. Plants have been used to produce a wide range of recombinant proteins of potential economic and/or medicinal importance. These include research chemicals (Hood et al., 1997 [11]; Zhong et al., 1999 [12]), processing enzymes that are used, for example, in the pharmaceutical industry (Woodard et al., 2003 [13]), industrial enzymes that are deployed in large-scale processing operations such as bleaching (Hood et al., 2003 [14]; Bailey et al., 2004 [15]), candidate vaccine antigens for animal or plant disease prevention (Mason et al., 1992 [16]; Haq et al., 1995 [17]; Carrillo et al., 1998 [18]; Streatfield et al., 2001 [19]), and therapeutic pharmaceuticals including antibodies (Daniell et al., 2001 [20]; Hood et al., 2002 [21]). The expressed proteins may either be purified from the plant tissues (Hood et al., 1997 [11]; Woodard et al., 2003 [13]) or, if as with vaccines the final application allows it, the recombinant plant material may be processed into a suitable form for use or even deployed directly (Streatfield et al., 2002 [22]; Lamphear et al., 2002 [23]). For these and other protein products to be produced in plant systems it is necessary that promoters drive a sufficiently high level of expression to ensure commercial viability.

Spatial and temporal control is also often important in driving gene expression in plants. For example selectable and scoreable markers must be expressed at a suitable time and in an appropriate tissue to allow for screening, and controlling enzymes and regulatory factors must be produced in metabolically active and physiologically responsive tissues, respectively. Similarly, genes conferring host protection must be expressed in the target tissues for the pathogen or pest, and plant produced protein products should be expressed in tissues suitable for protein accumulation and storage. Furthermore, since certain protein products may have detrimental affects on plant health and yield when expressed in metabolically active plant tissues that are essential for survival and growth, promoters may be favored that are active in the chosen plant storage tissues but show low or no activity in other, non-storage tissues.

Promoters that preferentially express relatively high levels of foreign proteins in tissues suitable for stable protein accumulation and storage are particularly useful for commercial protein production. The seed tissues of the cereals are especially well suited to the large-scale production of recombinant proteins. Thus, there is a requirement for promoters that show a seed tissue preferred expression pattern in plants and particularly cereals and drive relatively high levels of protein accumulation in these tissues.

Several promoters of plant and plant pathogen (bacterial and viral) origin have been used to direct transgene expression in plants. Prominent examples include the French bean beta-phaseolin promoter (Bustos et al., 1989 [24]), the mannopine synthase promoter of *Agrobacterium tumefaciens* (Leung et al., 1991 [25]), and the 35S promoter of cauliflower mosaic virus (Guilley et al., 1982 [26]). These and several other promoters in widespread use in plants were originally developed and utilized in dicot species. Promoter sequences from one species are predictably used in other species (see discussion below). The cereals comprise particularly important crops and there is therefore a pressing need for promoters that have high activity and/or tissue preference in monocots. Cereals, such as grasses, are cultivated for their grain. Since the nutritional value of cereals is in their seeds, and these tissues are also well suited for recombinant protein accumulation and storage, promoters that are active in cereal seed tissues are especially useful.

Two broad classes of promoters are typically deployed: constitutive and tissue preferred. Constitutive promoters, such as maize polyubiquitin-1 drive expression in the seed but also in other tissues (Christensen et al., 1992 [27]). A drawback with such constitutive promoters is that expression in tissues other than seed storage tissues may result in plant health being compromised, for example if a potentially toxic protein is expressed in metabolically active tissues required for germination or growth (Hood et al., 2003 [14]). Furthermore, constitutive expression may result in the expressed foreign protein being synthesized in pollen grains and thus being difficult to contain. By contrast, seed preferred promoters limit all or the bulk of transgene expression to seed tissues, so avoiding such concerns. Tissue preferred expression can include seed preferred expression. An example of one such promoter providing seed preferred expression is the phaseolin promoter. See, Bustos et al. (1989) [24].

The principle tissue types in maize seeds are the embryo, the endosperm including a surrounding aleurone cell layer and the maternally derived pericarp. Of these, the endosperm and to a lesser extent the embryo, comprise most of the volume of the seed. Thus, endosperm and embryo promoters are particularly important for modifying seed characteristics and contents. The proximal 1.1 kb of a maize 27 kD γ-zein promoter (Russell and Fromm, 1997 [28]) and the proximal 1.45 kb of a maize globulin-1 promoter (Belanger and Kriz, 1991 [29]; Genbank accession L22344) are prominent examples of seed preferred promoters that have been used to express transgenes in the seeds of monocots.

However, despite these examples, there is currently a very limited repertoire of promoters for preferentially expressing foreign or heterologous proteins or transcripts in the seed tissues of plants, and in particular, cereals. There is a need for further promoters that express transgenes at similar or higher levels to those currently deployed and with similar or improved tissue specificity. The best promoters would facilitate the expression of foreign proteins in seeds at higher levels than are currently achieved, while restricting expression specifically or predominantly to seed tissues. Also, a range of new promoters would allow the expression of multiple copies of a single transgene in seeds without the need to repeatedly use the same promoter. This should reduce silencing phenomena associated with promoter methylation (De Wilde et al., 2000 [30]), and thereby it should also serve to boost expression. Similarly, multiple distinct transgenes could be simultaneously expressed from different promoters in seed tissues, allowing more complex traits and foreign protein products to be reliably introduced into seeds.

SUMMARY OF THE INVENTION

This invention is in the field of plant biology and agriculture and relates to novel seed specific promoter regions. The present invention further provides methods of producing proteins and other products of interest and methods of controlling expression of nucleic acid sequences of interest using the seed specific promoter regions.

The endosperm of plants comprises almost entirely nutritional reserves, primarily of complex carbohydrate and insoluble protein, but the embryo also contains considerable stores, mainly of oils and soluble proteins. The data presented herein indicate that the transcript of unclassified gene GRMZM2G078441 is one of the most abundant RNA transcripts in maize embryo tissue. Given the high concentration of this transcript observed in embryo tissues the unclassified gene GRMZM2G078441 promoter is identified as being a good candidate to direct high levels of transgene expression in the embryo. It is believed that still more active promoters including unclassified gene GRMZM2G078441 promoter and variants thereof are very desirable for some applications, such as the expression of cost sensitive foreign or heterologous transcripts and proteins in cereal seeds.

In one embodiment, the invention relates to an isolated DNA molecule comprising a plant promoter region, wherein the promoter region is selected from the group consisting of SEQ ID NO: 3 and variants thereof that are at least 95% identical to SEQ ID NO: 3, and a heterologous gene operably linked to the promoter. In one embodiment, the invention relates to an expression vector, comprising the DNA molecule described above (SEQ ID NO: 3 and variants thereof that are at least 95% identical to SEQ ID NO: 3, and a heterologous gene operably linked to the promoter). In one embodiment, the invention relates to a transgenic plant cell, comprising the DNA molecule described above (SEQ ID NO: 3 and variants thereof that are at least 95% identical to SEQ ID NO: 3, and a heterologous gene operably linked to the promoter). In one embodiment, the invention relates to a transgenic plant, comprising the DNA molecule described above (SEQ ID NO: 3 and variants thereof that are at least 95% identical to SEQ ID NO: 3, and a heterologous gene operably linked to the promoter). In one embodiment, the invention relates to a transgenic plant embryo, comprising the DNA molecule described above (SEQ ID NO: 3 and variants thereof that are at least 95% identical to SEQ ID NO: 3, and a heterologous gene operably linked to the promoter). In one embodiment, the invention relates to a plant gene expression cassette comprising, in sequence, a promoter region selected from the group consisting of SEQ ID NO: 3 and variants thereof that are at least 95% identical to SEQ ID NO: 3, the coding region of a heterologous gene and a 3' polyadenylation signal.

In one embodiment, the invention relates to a method for selectively expressing a nucleotide sequence in a plant embryo, the method comprising transforming a plant embryo with a transformation vector comprising an expression cassette, the expression cassette comprising a regulatory element and a heterologous nucleotide sequence operably linked to the regulatory element, said regulatory element comprising the sequence of SEQ ID NO: 3.

In one embodiment, the invention relates to a method of producing a protein of interest in a plant embryo, comprising: a) providing a transgenic embryo comprising a heterologous nucleic acid sequence encoding the protein of interest operably linked to a promoter region, wherein the promoter region is selected from the group consisting of SEQ ID NO: 3 and variants thereof that are at least 95% identical to SEQ ID NO: 3; and b) growing the plant under conditions such that the protein is produced in said embryo. In one embodiment, said embryo is a monocot. In one embodiment, said expression corresponds with the embryonic stage of plant development.

In one embodiment, the invention relates to an isolated DNA molecule comprising a plant promoter region, wherein the promoter region is selected from the group consisting of SEQ ID NO: 1 and variants thereof that are at least 95% identical to SEQ ID NO: 1, and a heterologous gene operably linked to the promoter. In one embodiment, the invention relates to an expression vector, comprising the DNA molecule described above (SEQ ID NO: 1 and variants thereof that are at least 95% identical to SEQ ID NO: 1, and a heterologous gene operably linked to the promoter). In one embodiment, the invention relates to an expression vector, comprising the DNA molecule described above SEQ ID NO: 1 and variants thereof that are at least 95% identical to SEQ ID NO: 1 with intron removed, and a heterologous gene operably linked to the promoter). In one embodiment, the invention relates to a transgenic plant cell, comprising the DNA molecule described above (SEQ ID NO: 1 and variants thereof that are at least 95% identical to SEQ ID NO: 1, and a heterologous gene operably linked to the promoter). In one embodiment, the invention relates to a transgenic plant, comprising the DNA molecule described above (SEQ ID NO: 1 and variants thereof that are at least 95% identical to SEQ ID NO: 1, and a heterologous gene operably linked to the promoter). In one embodiment, the invention relates to a transgenic plant embryo, comprising the DNA molecule described above (SEQ ID NO: 1 and variants thereof that are at least 95% identical to SEQ ID NO: 1, and a heterologous gene operably linked to the promoter). In one embodiment, the invention relates to a plant gene expression cassette comprising, in sequence, a promoter region selected from the group consisting of SEQ ID NO: 1 and variants thereof that are at least 95% identical to SEQ ID NO: 1, the coding region of a heterologous gene and a 3' polyadenylation signal.

In one embodiment, the invention relates to a method for selectively expressing a nucleotide sequence in a plant embryo, the method comprising transforming a plant embryo with a transformation vector comprising an expression cassette, the expression cassette comprising a regulatory element and a heterologous nucleotide sequence operably linked to the regulatory element, said regulatory element comprising the sequence of SEQ ID NO 1.

In one embodiment, the invention relates to a method of producing a protein of interest in a plant embryo, comprising: a) providing a transgenic embryo comprising a heterologous nucleic acid sequence encoding the protein of interest operably linked to a promoter region, wherein the promoter region is selected from the group consisting of SEQ ID NO: 1 and variants thereof that are at least 95% identical to SEQ ID NO: 1; and b) growing the plant under conditions such that the protein is produced in said embryo. In one embodiment, said embryo is a monocot. In one embodiment, said expression corresponds with the embryonic stage of plant development.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Other objects, advantages, and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term "plant" is used in it broadest sense. It includes, but is not limited to, any species of woody, ornamental or decorative, crop or cereal, fruit or vegetable plant, and photosynthetic green algae (for example, *Chlamydomonas reinhardtii*). It also refers to a plurality of plant cells which are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including those present in roots, shoots, leaves, pollen, seeds and tumors, as well as cells in culture (for example, single cells, protoplasts, embryos, callus, etc.). Plant tissue may be in planta, in organ culture, tissue culture, or cell culture. The term "plant part" as used herein refers to a plant structure or a plant tissue. The term "seed" as used herein includes all tissues which result from the development of a fertilized plant egg; thus, it includes a matured ovule containing an embryo and stored nutrients, as well as the integument or integuments differentiated as the protective seed coat, or testa. The nutrients in seed tissues may be stored in the endosperm or in the body of the embryo, notably in the cotyledons, or both.

The term "crop" or "crop plant" is used in its broadest sense. The term includes, but is not limited to, any species of plant or algae edible by humans or used as a feed for animals or used, or consumed by humans, or any plant or algae used in industry or commerce.

The term plant cell "compartments or organelles" is used in its broadest sense. The term includes but is not limited to, the endoplasmic reticulum, Golgi apparatus, trans Golgi network, plastids, sarcoplasmic reticulum, glyoxysomes, mitochondrial, chloroplast, and nuclear membranes, and the like.

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein.

The term "portion" or "fragment" when used in reference to a protein (as in "a portion of a given protein") refers to fragments of that protein. The fragments may range in size from four amino acid residues to the entire amino acid sequence minus one amino acid.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences include those obtained from the same or from different species of organisms.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferrably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (for example, 99 percent sequence identity). Preferably, residue positions, which are not identical differ by conservative amino acid substitutions.

The terms "variant" and "mutant" when used in reference to a nucleic acid sequence means sequences that are at least 90% identical. Preferred variants have less than 10%, and preferably less than 5%, and still more preferably less than 2% changes (whether substitutions, deletions, and so on).

The nucleic acid molecules of this invention are typically DNA molecules, and include cDNA, genomic DNA, synthetic forms, and mixed polymers, both sense and antisense strands, and may be chemically or biochemically modified, or may contain non-natural or derivatised nucleotide bases as will be appreciated by those skilled in the art. Such modifications include labels, methylation, intercalators, alkylators and modified linkages.

The term "gene" refers to a nucleic acid (for example, DNA or RNA) sequence that comprises coding sequences necessary for the production of an RNA, or a polypeptide or its precursor. A functional polypeptide can be encoded by a full length coding sequence or by any portion of the coding sequence as long as the desired activity or functional properties (for example, enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences, which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers, which control or influence the transcription of the gene. The 3' flanking region may contain sequences, which direct the termination of transcription, posttranscriptional cleavage and polyadenylation.

The term "expression cassette" means a part of a vector DNA used for cloning and transformation. In each successful transformation, the expression cassette directs the cell's machinery to make RNA and protein. Some expression cassettes are designed for modular cloning of protein-encoding sequences so that the same cassette can easily be altered to make different proteins. An expression cassette is composed of one or more genes and the sequences controlling their expression. Three components comprise an expression cassette: a promoter sequence, an open reading frame, and a 3' untranslated region that, in eukaryotes, usually contains a polyadenylation site. Different expression cassettes can be transformed into different organisms including bacteria, yeast, plants, and mammalian cells as long as the correct regulatory sequences are used.

The phrase "expression corresponds with the embryonic stage of plant development" means that the production of RNA transcripts and/or subsequently related proteins under control of the preceeding promoter is significantly produced during the embryonic stage of plant development.

The phrase "embryonic stage of plant development" refers to a process that produces a plant embryo from a fertilized ovule by asymmetric cell division and the differentiation of undifferentiated cells into tissues and organs. It occurs during seed development, when the single-celled zygote undergoes a programmed pattern of cell division resulting in a mature embryo.

The term "heterologous" when used in reference to a gene refers to a gene that is not in its natural environment (in other words, has been altered by the hand of man). For example, a heterologous gene includes a gene from one species introduced into another species. A heterologous gene also includes a gene native to an organism that has been altered in some way (for example, mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (for example, genes expressed in loci where the gene is not normally expressed).

The term "oligonucleotide" refers to a molecule comprising two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The term "nucleotide sequence of interest" or "nucleic acid sequence of interest" refers to any nucleotide sequence (for example, RNA or DNA), the manipulation of which may be deemed desirable for any reason (for example, treat disease, confer improved qualities, etc.), by one of ordinary skill in the art. Such nucleotide sequences include, but are not limited to, coding sequences of structural genes (for example, reporter genes, selection marker genes, oncogenes, drug resistance genes, growth factors, etc.), and non-coding regulatory sequences which do not encode an mRNA or protein product (for example, promoter sequence, polyadenylation sequence, termination sequence, enhancer sequence, etc.).

The term "structural" when used in reference to a gene or to a nucleotide or nucleic acid sequence refers to a gene or a nucleotide or nucleic acid sequence whose ultimate expression product is a protein (such as an enzyme or a structural protein), an rRNA, an sRNA, a tRNA, etc.

The term "fragment" or "portion" when used in reference to an oligonucleotide sequence or a nucleic acid sequence refers to a length of the sequence which is less than the entire length as it occurs naturally (for example, as a DNA, RNA, or cDNA molecule). The fragments may range in size from a few nucleotides to the entire nucleic acid sequence minus one nucleotide. Thus, "a nucleotide comprising at least a portion of a gene" may comprise fragments of the gene or the entire gene.

The term "an oligonucleotide having a nucleotide sequence encoding a gene" or "a nucleic acid sequence encoding" a specified gene product refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (in other words, the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule, which comprises segments of nucleic acid joined together by means of molecular biological techniques. The term "recombinant" when made in reference to a protein or a polypeptide refers to a protein molecule, which is expressed using a recombinant nucleic acid molecule.

The terms "complementary" and "complementarity" refer to polynucleotides (in other words, a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (in other words, identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (in other words, the hybridization) of a sequence, which is completely homologous to a target under conditions of low stringency. This is not to say that conditions of low stringency are such that non-specific binding is permitted; low stringency conditions require that the binding of two sequences to one another be a specific (in other words, selective) interaction. The absence of non-specific binding may be tested by the use of a second target which lacks even a partial degree of complementarity (for example, less than about 30% identity); in the absence of non-specific binding the probe will not hybridize to the second non-complementary target.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (in other words, a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (in other words, gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math 2: 482 (1981) [31]) by the homology alignment algorithm of Needleman and Wunsch (Needleman and Wunsch, J. Mol. Biol. 48:443 (1970) [32]), by the search for similarity method of Pearson and Lipman (Pearson and Lipman, Proc. Natl. Acad. Sci. (U.S.A.) 85:2444 (1988) [33]), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (in other words, resulting in the highest percentage of homology over the comparison window) generated by the various methods is selected. The term "sequence identity" means that two polynucleotide sequences are identical (in other words, on a nucleotide-by-nucleotide basis) over the window of comparison. The term "percentage of sequence identity" is calculated by comparing two optimally aligned sequences over the window of comparison, determining the number of positions at which the identical nucleic acid base (for example, A, T, C, G, U, or I) occurs in both sequences to yield the number of matched positions, dividing the number of matched positions by the total number of positions in the window of comparison (in other words, the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

The term "substantially homologous" when used in reference to a double-stranded nucleic acid sequence such as a cDNA or genomic clone refers to any probe that can hybridize to either or both strands of the double-stranded nucleic acid sequence under conditions of low to high stringency as described below.

The term "substantially homologous" when used in reference to a single-stranded nucleic acid sequence refers to any probe that can hybridize (in other words, it is the complement of) the single-stranded nucleic acid sequence under conditions of low to high stringency as described below.

The term "hybridization" refers to the pairing of complementary nucleic acids. Hybridization and the strength of hybridization (in other words, the strength of the association between the nucleic acids) is impacted by such factors as the degree of complementary between the nucleic acids, stringency of the conditions involved, the Tm of the formed hybrid, and the G:C ratio within the nucleic acids. A single molecule that contains pairing of complementary nucleic acids within its structure is said to be "self-hybridized."

The term "Tm" refers to the "melting temperature" of a nucleic acid. The melting temperature is the temperature at which a population of double-stranded nucleic acid molecules becomes half dissociated into single strands. The equation for calculating the Tm of nucleic acids is well known in the art. As indicated by standard references, a simple estimate of the $T_m$ value may be calculated by the equation: $T_m=81.5+0.41$ (% G+C), when a nucleic acid is in aqueous solution at 1 M NaCl (See for example, Anderson and Young, Quantitative Filter Hybridization, in Nucleic Acid Hybridization (1985) [34]). Other references include more sophisticated computations that take structural as well as sequence characteristics into account for the calculation of $T_m$.

The term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent (50×Denhardt's contains per 500 ml: 5 g Ficoll (Type 400, Pharmacia), 5 g BSA (Fraction V; Sigma)) and 100 µg/ml denatured salmon sperm DNA followed by washing in a solution comprising 5×SSPE, 0.1% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1× SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (for example, the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (for example, increasing the temperature of the hybridization and/or wash steps, the use of formamide in the hybridization solution, etc.).

"Amplification" is a special case of nucleic acid replication involving template specificity. It is to be contrasted with non-specific template replication (in other words, replication that is template-dependent but not dependent on a specific template). Template specificity is here distinguished from fidelity of replication (in other words, synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q-replicase, MDV-1 RNA is the specific template for the replicase (Kacian et al., Proc. Natl. Acad. Sci. USA, 69:3038 (1972) [35]). Other nucleic acids will not be replicated by this amplification enzyme. Similarly, in the case of T7 RNA polymerase, this amplification enzyme has a stringent specificity for its own promoters (Chamberlin et al., Nature, 228:227 (1970) [36]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 (1989) [37]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press (1989) [38]).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (in other words, in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "probe" refers to an oligonucleotide (in other words, a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (for example, ELISA, as well as enzyme-based histochemical assays), fluorescent, radioactive, and luminescent systems. It is not intended that the present invention be limited to any particular detection system or label.

The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification [39-41]. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (in other words, denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (for example, hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

The term "gene expression" refers to the process of converting genetic information encoded in a gene into RNA (for example, mRNA, rRNA, tRNA, or snRNA) through "transcription" of the gene (in other words, via the enzymatic action of an RNA polymerase), and into protein, through "translation" of mRNA. Gene expression can be regulated at many stages in the process. "Up-regulation" or "activation" refers to regulation that increases the production of gene expression products (in other words, RNA or protein), while "down-regulation" or "repression" refers to regulation that decrease production. Molecules (for example, transcription factors) that are involved in up-regulation or down-regulation are often called "activators" and "repressors," respectively.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. By "promoter" is meant a regulatory region of DNA capable of regulating the transcription of a sequence linked thereto. It usually comprises a TATA box capable of directing RNA polymerase II to initiate RNA synthesis at the appropriate transcription initiation site for a particular coding sequence. The promoter is the minimal sequence sufficient to direct transcription in a desired manner. The term "regulatory region" is also used to refer to the sequence capable of initiating transcription in a desired manner. By "seed preferred" is intended favored expression in the seed of the plant, and "embryo preferred" indicates favored expression in the embryo of the seed of the plant.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987 [42]). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986 [43]; and Maniatis, et al., supra 1987 [42]).

The terms "promoter element," "promoter," or "promoter sequence" refer to a DNA sequence that is located at the 5' end (in other words precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "regulatory region" refers to a gene's 5' transcribed but untranslated regions, located immediately downstream from the promoter and ending just prior to the translational start of the gene.

The term "promoter region" refers to the region immediately upstream of the coding region of a DNA polymer, and is typically between about 500 bp and 4 kb in length, and is preferably about 1 to 1.5 kb in length. A promoter region controls or regulates transcription of a gene to which it is operably linked, either naturally or by recombinant nucleic acid technology. A promoter region may include smaller sequences which are effective to control or regulate transcription. One skilled in the art can determine such smaller sequences by creating fragments of decreasing size from a promoter region, and operably linking such fragments to a reporter gene, and determining expression of such constructs in transgenic tissue, as described further herein.

Promoters may be tissue specific or cell specific. The term "tissue specific" as it applies to a promoter refers to a promoter that is capable of directing selective expression of a nucleotide sequence of interest to a specific type of tissue (for example, seeds) in the relative absence of expression of the same nucleotide sequence of interest in a different type of tissue (for example, leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (for example, detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, for example, immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (for example, peroxidase conjugated) secondary antibody which is specific for the primary antibody is allowed to bind to the sectioned tissue and specific binding detected (for example, with avidin/biotin) by microscopy.

A promoter is "effective" as a tissue specific or cell type promoter when expression in the presence of the promoter is greater in the tissue or cell type than expression in the presence of the promoter in other tissues or cell types. Preferably, the greater level of expression is at least about two-fold greater; more preferably, it is at least about four-fold greater; and most preferably, it is at least about ten-told greater. An effective promoter may comprise all of the promoter region, or a modification or fragment of a promoter region, or a motif of a promoter region.

A "seed-specific promoter" is a promoter which controls or regulates expression of a gene to which it is operably linked in a seed or seed tissue; such expression may occur in developing seed tissue only, at differing times or levels, or in mature seed tissue, or in both. Preferably, expression of the gene in seed tissue is greater than in non-seed tissue when under control of a seed-specific promoter. Preferably, the greater level of expression is at least about two-fold greater; more preferably, it is at least about four-fold greater; and most preferably, it is at least about ten-fold greater.

A gene, which is preferentially expressed in seeds or seed tissue, is expressed at a higher level than it is in non-seed tissue. Preferably, expression of the gene in seed tissue is greater than in non-seed tissue. Preferably, the greater level of expression is at least about two-fold greater; more preferably, it is at least about four-fold greater; and most preferably, it is at least about ten-fold greater Promoters may be constitutive or inducible. The term "constitutive" when made in reference to a promoter means that the promoter is capable of directing transcription of an operably linked nucleic acid sequence in the absence of a stimulus (for example, heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see for example, U.S. Pat. No. 5,352,605 [44], incorporated herein by reference), mannopine synthase, octopine synthase (ocs), superpromoter (see for example, WO 95/14098 [45]), and ubi3 (see for example, Garbarino and Belknap, Plant Mol. Biol. 24:119-127 (1994) [46]) promoters. Such promoters have been used successfully to direct the expression of heterologous nucleic acid sequences in transformed plant tissue.

In contrast, an "inducible" promoter is one which is capable of directing a level of transcription of an operably linked nucleic acid sequence in the presence of a stimulus (for example, heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (in other words, molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (for example, the first and second genes can be from the same species, or from different species).

The term "naturally linked" or "naturally located" when used in reference to the relative positions of nucleic acid sequences means that the nucleic acid sequences exist in nature in the relative positions.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory Manual,* 2nd ed., Cold Spring Harbor Laboratory Press, New York (1989) pp. 16.7-16.8 [47]). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly (A) signal. The SV40 poly(A) signal is contained on a 237 bp BamHI/BclI restriction fragment and directs both termination and polyadenylation (Sambrook, supra, at 16.6-16.7 [47]).

The term "termination signal" or "termination sequence" refers to a 3' non-translated DNA sequence which functions in plant cells to cause the addition of polyadenylated ribonucleotides to the 3' end of an mRNA sequence transcribed from a gene; the gene may be an endogenous or native gene, or it may be a heterologous gene. The termination sequence may be endogenous or heterologous to the gene.

The term "vector" refers to nucleic acid molecules that transfer DNA segment(s) from one cell to another. The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (in other words, particle bombardment) and the like.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 (1973) [48]), has been modified by several groups to optimize conditions for particular types of cells. The art is well aware of these numerous modifications.

The terms "infecting" and "infection" when used with a bacterium refer to co-incubation of a target biological sample, (for example, cell, tissue, etc.) with the bacterium under conditions such that nucleic acid sequences contained within the bacterium are introduced into one or more cells of the target biological sample.

The term "*Agrobacterium*" refers to a soil-borne, Gram-negative, rod-shaped phytopathogenic bacterium, which causes crown gall. The term "*Agrobacterium*" includes, but is not limited to, the strains *Agrobacterium tumefaciens*, (which typically causes crown gall in infected plants), and *Agrobacterium rhizogens* (which causes hairy root disease in infected host plants). Infection of a plant cell with *Agrobacterium* generally results in the production of opines (for example, nopaline, agropine, octopine etc.) by the infected cell. Thus, *Agrobacterium* strains which cause production of nopaline (for example, strain LBA4301, C58, A208, GV3101) are referred to as "nopaline-type" Agrobacteria; *Agrobacterium* strains which cause production of octopine (for example, strain LBA4404, Ach5, B6) are referred to as "octopine-type" Agrobacteria; and *Agrobacterium* strains which cause production of agropine (for example, strain EHA105, EHA101, A281) are referred to as "agropine-type" Agrobacteria.

The terms "bombarding," "bombardment," and "biolistic bombardment" refer to the process of accelerating particles towards a target biological sample (for example, cell, tissue, etc.) to effect wounding of the cell membrane of a cell in the target biological sample and/or entry of the particles into the target biological sample. Methods for biolistic bombardment are known in the art (for example, U.S. Pat. No. 5,584,807 [49], the contents of which are incorporated herein by reference), and are commercially available (for example, the helium gas-driven microprojectile accelerator (PDS-1000/He, BioRad).

The term "microwounding" when made in reference to plant tissue refers to the introduction of microscopic wounds in that tissue. Microwounding may be achieved by, for example, particle bombardment as described herein.

The term "transgene" refers to a foreign gene that is placed into an organism by the process of transfection. The term "foreign gene" refers to any nucleic acid (for example, gene sequence) that is introduced into the genome of an organism by experimental manipulations and may include gene sequences found in that organism so long as the introduced gene does not reside in the same location as does the naturally-occurring gene.

The term "transgenic" when used in reference to a plant or fruit or seed (in other words, a "transgenic plant" or "transgenic fruit" or a "transgenic seed") refers to a plant or fruit or seed that contains at least one heterologous or foreign gene in one or more of its cells. The term "transgenic plant material" refers broadly to a plant, a plant structure, a plant tissue, a plant seed or a plant cell that contains at least one heterologous gene in one or more of its cells.

The term "host cell" refers to any cell capable of replicating and/or transcribing and/or translating a heterologous gene. Thus, a "host cell" refers to any eukaryotic or prokaryotic cell (for example, bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "selectable marker" refers to a gene which encodes an enzyme having an activity that confers resistance to an antibiotic or drug upon the cell in which the selectable marker is expressed, or which confers expression of a trait which can be detected (for example., luminescence or fluorescence). Selectable markers may be "positive" or "negative." Examples of positive selectable markers include the neomycin phosphotransferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, luciferase (See for example, deWet et al., Mol. Cell. Biol. 7:725 (1987) [50] and U.S. Pat. No. 6,074,859 [51]; U.S. Pat. No. 5,976,796 [52]; U.S. Pat. No. 5,674,713 [53]; and U.S. Pat. No. 5,618,682 [54]; all of which are incorporated herein by reference), green fluorescent protein (for example, GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

The term "wild-type" when made in reference to a nucleic acid sequence refers to a nucleic acid sequence which has the characteristics of the sequence isolated from a naturally occurring source. The term "wild-type" when made in reference to a gene product refers to a gene product which has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is that which is most frequently observed in a population and is thus arbitrarily designated the "normal" or "wild-type" form of the gene. In contrast, the term "modified" or "mutant" when made in reference to a nucleic acid sequence (such as a regulatory sequence or a sequence encoding a gene) or to a gene product refers, respectively, to a nucleic acid sequence or to a gene product which displays modifications in sequence and/or functional properties (in other words, altered characteristics) when compared to the wild-type gene or gene product. Modifications include additions or deletions of the units making up the nucleic acid sequence or gene product (a unit is, for example, a nucleotide), or substitutions of at least one of the units. It is noted that naturally-occurring mutants can be isolated; these are identified by the fact that they have altered characteristics when compared to the wild-type nucleic acid sequence or gene product.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, in other words, at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "overexpression" refers to the production of a gene product in transgenic organisms that exceeds levels of production in normal or non-transformed organisms. The term "cosuppression" refers to the expression of a foreign gene which has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook et al. (1989) *Molecular Cloning: A Laboratory Manual* (Cold Spring Harbor Press, NY), pp 9.31-9.58 [55]).

The term "Northern blot analysis" and "Northern blot" and "Northern" refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. (1989) supra, pp 7.39-7.52 [56]).

The terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabelled antibodies.

The term "antigenic determinant" refers to that portion of an antigen that makes contact with a particular antibody (in other words, an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (in other words, the "immunogen" used to elicit the immune response) for binding to an antibody.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (for example, a gene) is found on the host cell chromosome in proximity to neighboring genes; RNA sequences, such as a specific mRNA sequence encoding a specific protein, are found in the cell as a mixture with numerous other mRNA s which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (in other words, the oligonucleotide may single-stranded), but may contain both the sense and anti-sense strands (in other words, the oligonucleotide may be double-stranded).

The term "purified" refers to molecules, either nucleic or amino acid sequences that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "sample" is used in its broadest sense. In one sense it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

Abbreviations

DAP: Days after pollination; qRT-PCR: Quantitative real time polymerase chain reaction; ABA: Abscisic Acid; GA: Gibberllic Acid; GSNAP: Genomic short-read nucleotide alignment program; FC: Fold-changes; GO: Gene Ontology; RPKM: Reads per kilobase of exon per million mapped reads; TCA: Tricaboxylic Acid Cycle; TAG: Triacylglycerol; LTP: Lipid transfer proteins; LEA: Late embryogenesis abundant; glb2: Globulin 2 gene; SNP: Single nucleotide polymorphism

DESCRIPTION OF THE FIGURES

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

FIG. 1A. Scutellar surface; FIG. 1B. Embryonic axis. Limits of axis [A] are indicated by brackets. Bar=1 mm.

FIG. 5A. Each set of 3 vertical bars (blue, red, green) indicates the number of transcripts counted for the respective time points for the individual locus enumerated on the X-axis. FIG. 5B. qPCR counts for glb-1 and cupin genes.

FIG. 17 shows the sequence upstream of the unclassified gene GRMZM2G078441 [SEQ ID NO: 1].

FIG. 18 shows the GRMZM2G078441 gene sequence [SEQ ID NO: 2].

FIG. 19 shows the shortened sequence upstream of the unclassified gene GRMZM2G078441 [SEQ ID NO: 3].

DETAILED DESCRIPTION OF THE INVENTION

Figure 1:
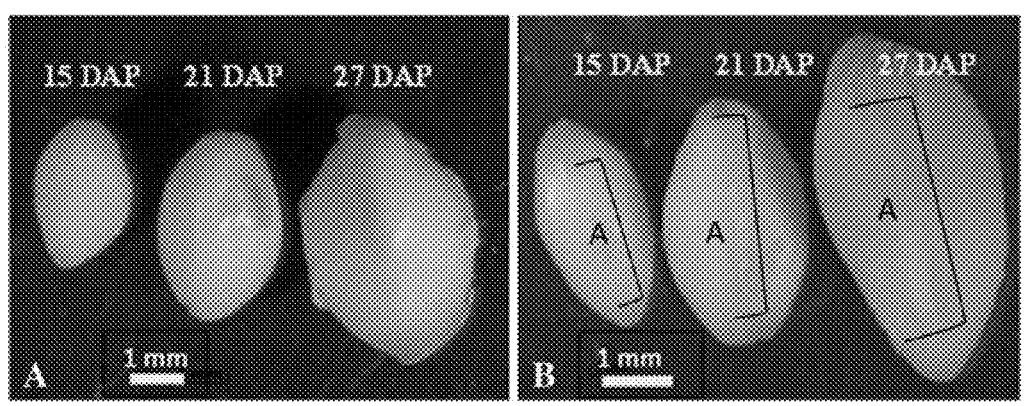
FIG. 1 shows maize embryos removed from seeds at 15, 21, and 27 days after pollination (DAP).

The present invention relates to novel specific promoter regions. The present invention further comprises methods of producing proteins and other products of interest and methods of controlling expression of nucleic acid sequences of interest using the specific promoter regions.

The maize embryo has been used to express foreign proteins for industrial applications [14, 57, 58]. For example, genes for an endocellulase, E1, and an exocellulase, CBH I, have been transformed into maize, plants recovered, and seed collected. The original maize tissue culture germplasm, Hi-II, is transformation competent but not agronomically productive [59]. Thus, high-expressing transformants must be bred into elite germplasm for improved field performance to optimize the production system for commercialization. In each case, when original transformants are bred into elite germplasm, higher accumulation of the target protein can be achieved by selection [22, 58, 60]. While this has been observed empirically many times in corn, the mechanism of this phenomenon is not known. In order to understand the genetic basis of this mechanism, an understanding of the genes involved in normal embryo development is critical. The embryo maturation stage is critical for these studies because the foreign genes of interest, i.e. the cellulases, are expressed from the globulin-1 promoter—an embryo seed storage protein promoter that is active during the mid-maturation phase of embryo development [29].

The process of seed development in maize is understood from the perspective of morphology, storage protein accumulation and hormone responses [61-65]. For example, Kiesselbach [63] published one of the earliest treatises on the development of maize, including the gametes, embryo and seed. His was primarily a visual study using the light microscope with limited sub-cellular detail though elegantly detailed on the developmental timeline. In addition, Kriz added detail on reserves by showing that the globulins (1 and 2) are the most abundant storage proteins in the embryo [64]. These proteins are formed during maturation and degraded during germination, providing carbon and nitrogen sources for the growing seedling. In the endosperm, zeins are the major storage reserves and their accumulation is intricately staged [62]. These reserves are also degraded during germination to feed the growing embryo. McCarty reviewed the viviparous mutants of maize and their phenotypic responses to abscisic acid (ABA) and gibberellins (GAs) during embryo development and maturation [61]. ABA is best known for its control of plant responses to stress, including drought [66]. Similarly, dessication in seeds is controlled by ABA [61]. Collectively these studies describe a framework that defines seed development and maturation. However, to fully understand these processes, we must take advantage of the new technologies that are available, such as transcriptome sequencing.

Specifically for the embryo, Kiesselbach [63] showed that at 13-15 days after pollination (DAP) the embryo has only the rudimentary structures of a scutellum (cotyledon) and meristem. By 21 DAP, the embryo structure is apparent with the shoot and root tips discernible. By 25 DAP, the embryonic structures are fully formed with shoot tip and radical covered by the coleoptile and the coleorhiza, respectively [63]. According to Vernoud et al. [61], the embryo starts maturation at 15 DAP and storage reserves are accumulating by 21 DAP. These early studies were used to design transcriptome sequencing experiments of maturing embryos.

Previous gene expression studies describe the regulation of seed development and maturation, including patterns for cell division, DNA replication, induction of morphological changes, storage protein accumulation and desiccation for dormancy [67-70]. Vernoud et al. provide an overview of gene expression during maize embryogenesis, including descriptions of mutants and cloned genes [68]. Microarray profiling of gene expression changes during embryo development was performed by Lee et al. [67]. Their custom array included 900 genes from EST libraries that were predicted to be involved in metabolism and embryogenesis. They found groups of genes that were expressed at different stages during seed development, moving from cell division activities at early stages to storage reserve synthesis and dessication. Genome-wide microRNA genes are also being surveyed to eventually determine their functional role in regulation of seed growth and development [70].

A transcriptomic analysis was undertaken of normal maturing embryos of one elite germplasm line that is utilized for the crosses to transgenic events originally made in Hi II germplasm. In this study, the transcriptome of embryos from 15, 21 and 27 DAP were analyzed to determine the genes that are expressed at these time points. More than 19,000 genes were analyzed by this method and the challenge was to choose subsets of genes that are vitally important to embryo development and maturation for the initial analysis. The changes in expression of genes relating to primary metabolic pathways, DNA synthesis, late embryogenesis proteins, and embryo storage proteins are described herein. Changes shown through transcriptome analysis and confirmed expression levels of a subset of genes in the tranriptome through qRT-PCR are also described.

Results

Collection of Embryos

The elite inbred, SP114, from which the embryos were analyzed is a Stiff Stalk variety germplasm (U.S. Pat. No. 6,252,148 [71]). A parallel Lancaster variety was used as a complement for the hybrid but is not described here. Embryos were isolated under sterile conditions using immature ears from plants grown in the greenhouse with 16 hour light and 8 hour dark periods. We have chosen to study the expression of maize embryo genes at three time points, 15, 21 and 27 days after pollination (DAP), referred to as S15, S21 and S27, combining the genotype (SP114) with the harvest time. Interest herein was in gene expression changes over the greatest range of active maturation, and these three times correspond to the early, mid and late phases of embryo maturation (FIG. 1). The first observation is the dramatic change in size during this time period. Clearly, much growth has occurred between 15 and 27 DAP, as well as significant development of the embryonic axis. Analysis of embryos at stages encompassing storage protein accumulation were desired because the promoter that drives the expression of our transgenes is the globulin-1 promoter, an embryo storage protein. The three time points chosen correspond with the expression pattern of the globulin-1 gene. The transcripts of the globulin-1 gene have been shown to begin accumulating at approximately 18 DAP, peak at 24 DAP and begin to decline at 27 DAP [29].

Overview of the Maize Embryo Transcriptome

Total RNA was isolated from pooled maturing embryos from a single ear at each sampling time. RNA sequencing was performed using Illumina GA II/Solexa instrumentation (Tufts Core Facility, Tufts University School of Medicine, Boston, Mass.). Single end reads of seventy-two nucleotides were conducted. A total of 56.2 million raw reads were generated for the three samples, out of which 52.9 million trimmed reads were available for mapping to the maize reference genome ZmB73AGPv1 (Table 1). The number of trimmed reads actually mapped to the reference genome was 42.9 million but only 10.4 million of these reads (20%) were uniquely mapped to individual loci. Almost 70% of the uniquely mapped reads were mapped within known exons. The summary of the trimming and alignment for each sample is shown in Table 1.

TABLE 1

Summary of trimming and alignment

| Samples | Raw reads | Trimmed reads | Mapped reads (%, mapped/trimmed) | Uniquely mapped reads (%, unique/trimmed) | Uniquely mapped reads in genes (%, in genes/unique) |
|---|---|---|---|---|---|
| S15 | 22,449,515 | 20,907,381 | 16,987,823 81.3% | 4,078,452 19.5% | 2,879,805 70.6% |
| S21 | 19,673,902 | 18,922,999 | 14,712,171 77.7% | 3,950,666 20.9% | 2,801,575 70.9% |
| S27 | 14,104,109 | 13,104,891 | 11,217,261 85.6% | 2,405,976 18.4% | 1,577,049 65.5% |
| Total | 56,227,526 | 52,935,271 | 42,917,255 | 10,435,094 | 7,258,429 |

Figure 2:
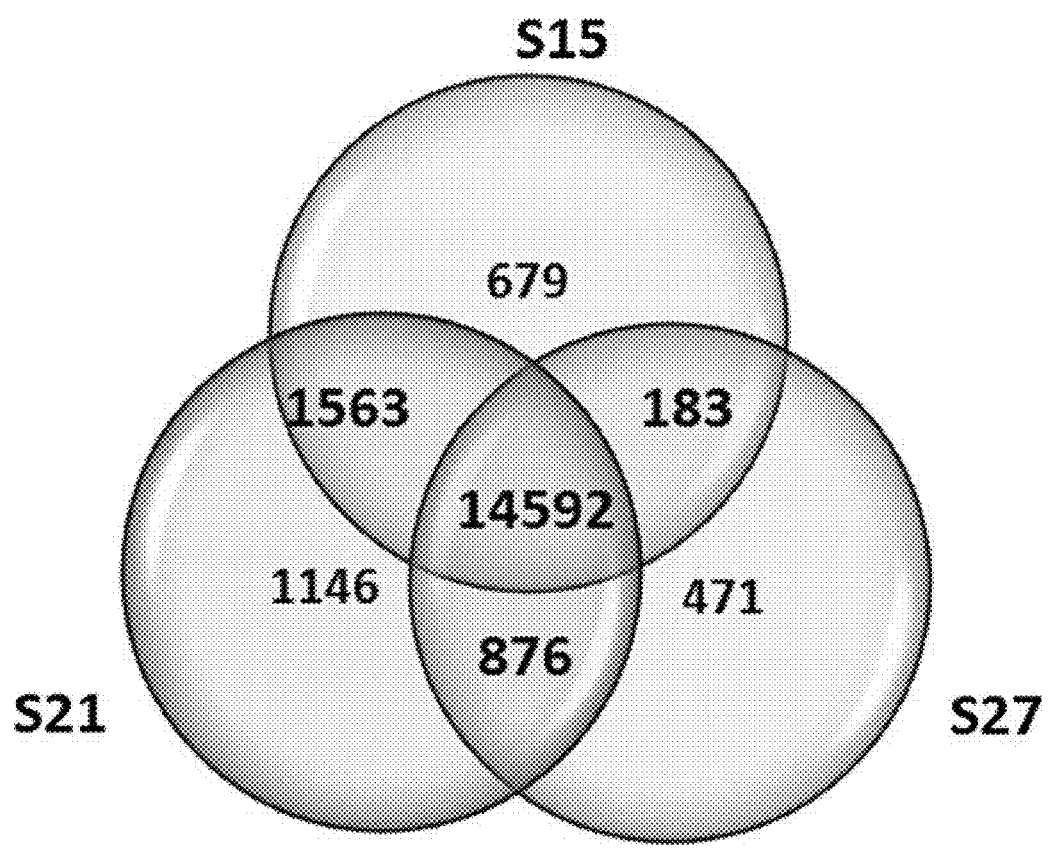
FIG. 2 shows the shared and unique genes (RPKM≥1) among the three maturing stages of the maize embryo. 19,510 genes are expressed at the 3 stages with the majority (14,592) expressed at all stages. S15=679 unique genes; S21=1146 unique genes; S27=471 unique genes.
Figure 3:
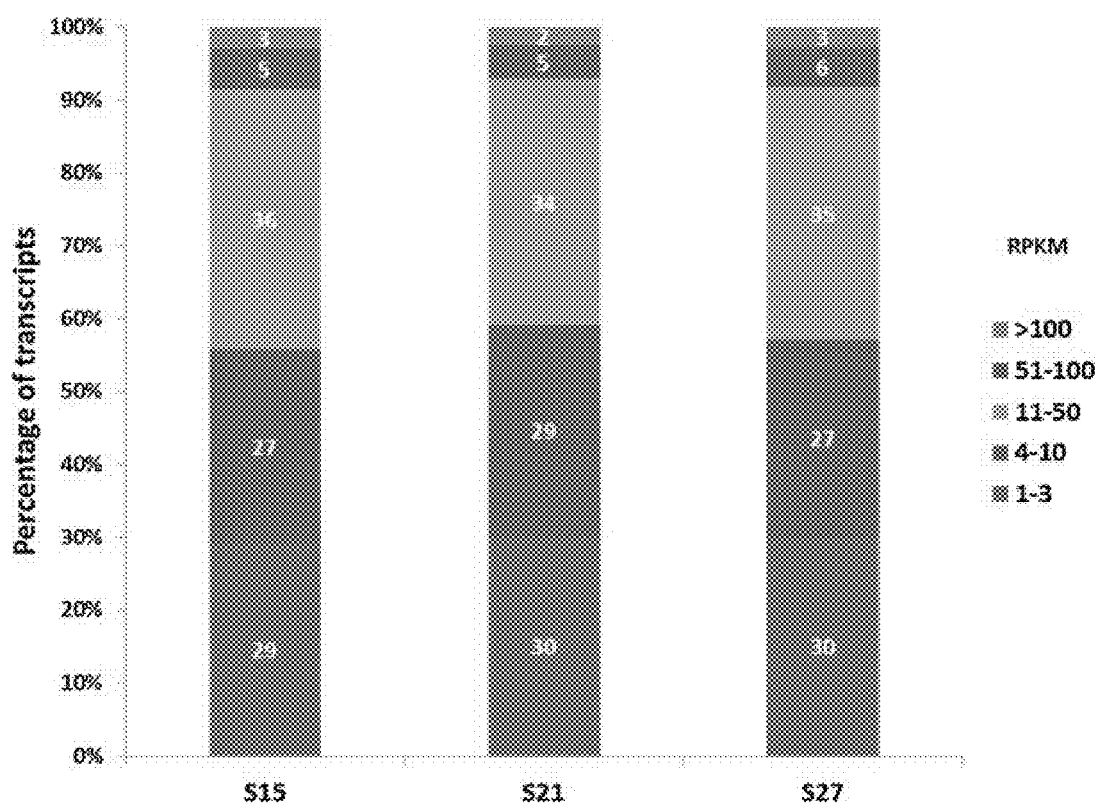
FIG. 3 shows the percent of transcripts with different expression abundances based on RPKM. Genes showing 11-50 copies per transcriptome were most highly represented at each stage.

The normalized reads referred to as reads per kilobase of exon per million mapped reads (RPKM), were used to estimate the total number of genes expressed throughout embryo maturation. The RPKM method corrects for biases in total gene exon size and normalizes for the total number of read sequences of each library obtained from each sample [72]. RPKM values≥1 were used in the estimation of the number of genes expressed. The total number of genes counted in the maturing embryo was 19,510 representing almost 60% of the annotated transcriptome of maize. Of these, 17,017 (87%) were expressed in S15, 18,177 (93%) in S21 and 16,122 (83%) in S27 (Table 2). FIG. 2 shows the number of genes uniquely expressed in each stage, or genes that are shared with one or two other stages. In this study, 14,592 (75%) of the expressed genes are represented in all three stages of embryo maturation that were analyzed and 12% are expressed in a single stage. The differences in expression of shared genes are of interest to discover how they change throughout embryo maturation. Moreover, single genes are of interest because of their potential importance at that stage. The gene expression levels in each stage of embryo maturation are classified into five categories based on their RPKM values—very low (1-5 RPKM), low (>5-10 RPKM), moderate (>10-50 RPKM), high (>50-100) and very high (>100 RPKM) (FIG. 3). Only a small percentage of the genes fall into the high (5-6%) and very high abundance (2-3%) categories.

TABLE 2

Number of genes expressed at each stage of embryo maturation

| Stage | Total number of genes expressed |
|---|---|
| S15 | 17,107 |
| S21 | 18,177 |
| S27 | 16,122 |
| Average | 17,105 |

Differential Expression of Maize Embryo Genes

Figure 4:
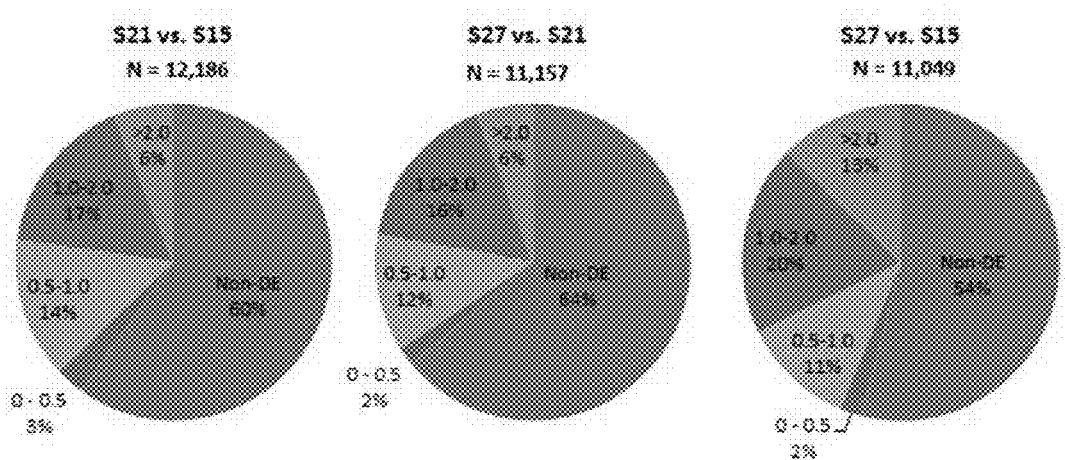
FIG. 4 shows the proportion of differentially expressed genes at each time point.
Figure 5:
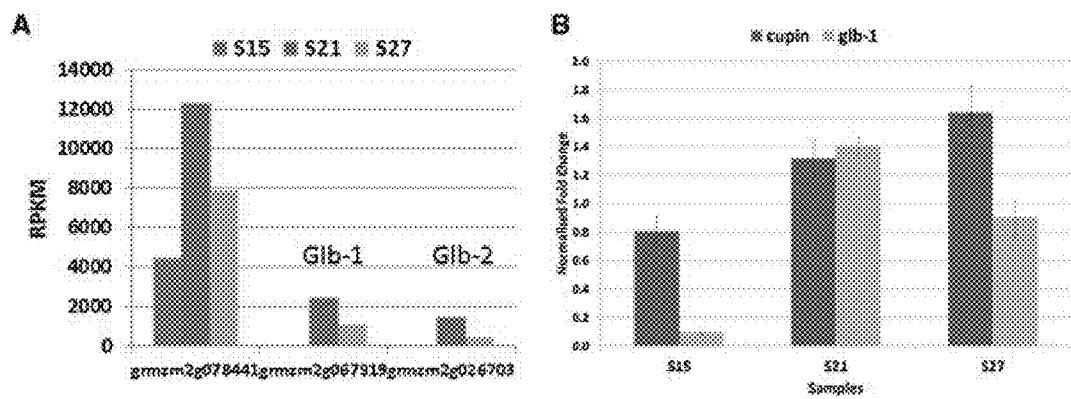
FIG. 5 shows the transcript profile (FIG. 5A) and qPCR results (FIG. 5B) of cupin family storage protein genes in maturing maize embryos.

The number of genes that showed differential expression (p<0.001 and q<0.001) is 7,124 out of the 19,510 total genes expressed in maturing embryos, representing approximately 36.5% of the embryo transcriptome. More than half of the differentially expressed genes showed at least a two-fold change in expression level in all three pairwise comparisons (Table 3). For genes that showed at least a two-fold change, almost as many were up-regulated as down-regulated, except between S27 and S15, where a higher proportion of genes were down-regulated, 56% compared to 44% that were up-regulated (Table 3). The proportion of differentially expressed genes was highest in the S27 vs S15 comparison (46%) and lowest in the S21 vs S27 comparison (36%) (FIG. 4). qRT-PCR was used to validate the expression levels of 11 transcripts and found a high correlation (R2=0.941) between mRNA-seq data and qRT-PCR (Table 4). The most notable result from the qRT-PCR was the high level of cupin expression compared to the globulin-1 gene during storage protein accumulation. (See FIG. 5 for details).

TABLE 3

Differential expression of genes between pairwise comparisons of embryo stages

| Comparison stages | No. of genes tested[1] | Differentially expressed[2] | \|log 2 FC\| [3] ≥1 | Up-regulated (≥1) | Down-regulated (≤1) |
|---|---|---|---|---|---|
| S15 vs S21 | 12,186 | 4,890 | 2,812 | 1,481 | 1,331 |
| S21 vs S27 | 11,157 | 4,032 | 2,499 | 1,243 | 1,256 |
| S27 vs S15 | 11,049 | 5,085 | 3,590 | 1,585 | 2,005 |

[1]Number of genes with 50 total reads combined from the two data sets in the pairwise comparison.
[2]p-value <0.001 and q-value <0.001. [3] Absolute value of log2 (fold change).

TABLE 4 qRT PCR of selected genes

| Gene ID | Forward Primer | Reverse Primer | RPKM | | | qRT-PCR | | | $R^2$ |
|---|---|---|---|---|---|---|---|---|---|
| | | | S15 | S21 | S27 | S15 | S21 | S27 | |
| Grmzm2g032905 | 5'-TCCAATAATTCGTAACCAT-3' [SEQ ID NO: 4] | 5'-CACTCACAGATAGTAACC-3' [SEQ ID NO: 5] | 10 | 0 | 0 | 0 | 0 | 0 | |
| Grmzm2g146283 | 5'-GATGCTGAGAGGAGGGATT-3' [SEQ ID NO: 6] | 5'-CCATTGTTGCCACCACTC-3' [SEQ ID NO: 7] | 0 | 0 | 31 | 0.34801 | 0.06485 | 1.08494 | 0.9277 |
| Grmzm2g123896 | 5'-GATGGATGGACAGTGAAG-3' [SEQ ID NO: 8] | 5'-AGCAGAACAAGAACAACA-3' [SEQ ID NO: 9] | 3 | 62 | 74 | 0.10724 | 1.01321 | 1.08494 | 0.9914 |
| Grmzm2g036448 | 5'-CTTCACCTTCCACTTCAA-3' [SEQ ID NO: 10] | 5'-AATGGGGTAAAAGCAAAG-3' [SEQ ID NO: 11] | 1 | 16 | 18 | 0.24669 | 1.12102 | 1.08494 | 0.9793 |
| Grmzm2g067919 | 5'-GCGAGTTCCAGTTCTTCTT-3' [SEQ ID NO: 12] | 5'-TCTTGTACGCAGCTCTCT-3' [SEQ ID NO: 13] | 62 | 2481 | 1118 | 0.09528 | 1.40596 | 0.9019 | 0.9528 |
| Grmzm2g057690 | 5'-AATGTGAAGAGTCCAGTGG-3' [SEQ ID NO: 14] | 5'-CGTCCTCAGGTGATGATG-3' [SEQ ID NO: 15] | 218 | 7 | 1 | 1.19848 | 0.07995 | 0.01837 | 0.9995 |
| Grmzm2g106980 | 5'-GCATACAAGAGCAACAAGATAC-3' [SEQ ID NO:16] | 5'-AAGAGTGTGGCGAGTAGT-3' [SEQ ID NO: 17] | 0 | 166 | 358 | 0.00023 | 0.68745 | 1.75852 | 0.993 |
| Grmzm2g034828 | 5'-TGCCTCCACACGGTTATCAC-3' [SEQ ID NO: 18] | 5'-GATGCTCATTCTTGCCTTGTTGT-3' [SEQ ID NO: 19] | 485 | 56 | 0 | 1.19848 | 0.07586 | 0.01985 | 0.996 |
| Grmzm2g080588 | 5'-GGGACATTAAACCAGAGAATC-3' [SEQ ID NO: 20] | 5'-GAACTCATAGCACAGAACAC-3' [SEQ ID NO: 21] | 351 | 16 | 0 | 1.19848 | 0.17478 | 0.13669 | 0.9999 |
| Grmzm2g159547 | 5'-GTGCGAGTTTGTATGAAT-3' [SEQ ID NO: 22] | 5'-AACTACACCTCTGAACTG-3' [SEQ ID NO: 23] | 36 | 0 | 0 | 1.14088 | 0.61555 | 0 | 0.7095 |
| Grmzm2g078441 | 5'-ATCCAGAGCTACCCCAACGC-3' [SEQ ID NO: 24] | 5'-CTTGGGCTTCGAGGGGTCAT-3' [SEQ ID NO: 25] | 4456 | 12331 | 7857 | 0.80477 | 1.31593 | 1.64051 | 0.2942 |

| Reference Genes | | | Accession number | Gene description |
|---|---|---|---|---|
| grmzm2g343543_T01 | 5'-GCCCGTTATGATGAGATT-3' [SEQ ID NO: 26] | 5'-AGAGATGGGAACAAAGTG-3' [SEQ ID NO: 27] | NM_001159196 | ef-1a |
| grmzm2g834758 | 5'-AATTGCGTTGTTACTTAATGTGTA-3' [SEQ ID NO:28] | 5'-CCTCCGACTTGGACTTGT-3' [SEQ ID NO: 29] | AJ131373 | Hmg-a |
| grmzm2g102471_T01 | 5'-GCTTGCTGACTACAACATC-3' [SEQ ID NO: 30] | 5'-CCTTGTCCTGGATCTTGG-3' [SEQ ID NO: 31] | NM_001154750 | Ubiquitin |

Embryo maturation follows embryo pattern formation and differentiation, beginning at 15 DAP and lasting for about 30 days [68]. Embryo maturation is marked by growth, active accumulation of reserve substances and some developmental events. Growth is characterized by a period of active precursor biosynthesis, DNA synthesis and cell division [73, 74], and reserve accumulation is characterized by the biosynthesis and deposition of storage proteins, fatty acids and starch [75-77].

Figure 6:
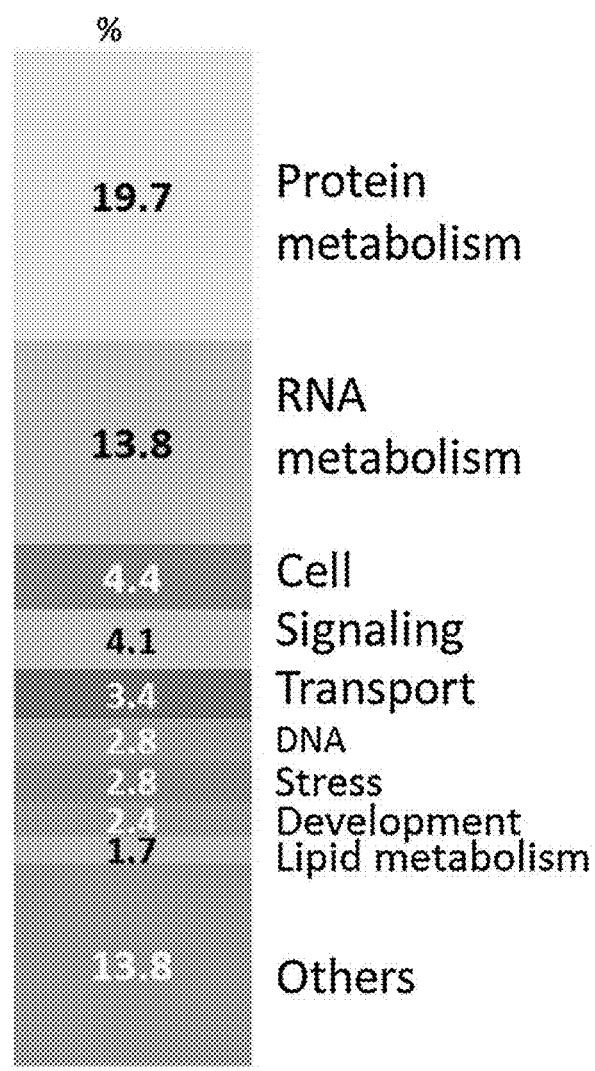
FIG. 6 shows the functional distribution of genes in maturing embryo. Categories are based on those present in Mapman software. Approximately 35% of all genes expressed are involved in protein and RNA metabolism.

Mapman annotation was adopted for the SP114 embryo transcriptome using the mapping file Zm_Genome_Release_09 [78, 79] to assign genes to 35 functional categories (Table 5). Protein and RNA metabolism are the two functional categories showing the greatest number of transcribed genes. The distribution of normalized reads among the top nine functional categories is shown in FIG. 6 excluding the 30% belonging to the 'not assigned or unknown' category (category 35).

TABLE 5

Functional categories

| Bincode | Functional Category |
|---|---|
| 1 | PhotoSynthesis |
| 2 | major CHO metabolism |
| 3 | minor CHO metabolism |
| 4 | glycolysis |
| 5 | fermentation |
| 6 | gluconeogenesis/glyoxylate cycle |
| 7 | OPP |
| 8 | TCA/org. transformation |
| 9 | mitochondrial electron transport/ATP synthesis |
| 10 | cell wall |
| 11 | lipid metabolism |
| 12 | N-metabolism |
| 13 | amino acid metabolism |
| 14 | S-assimilation |
| 15 | metal handling |
| 16 | secondary metabolism |
| 17 | hormone metabolism |
| 18 | Co-factor and vitamin metabolism |
| 19 | tetrapyrrole synthesis |
| 20 | stress |
| 21 | redox.regulation |
| 22 | polyamine metabolism |
| 23 | nucleotide metabolism |
| 24 | Biodegradation of Xenobiotics |
| 25 | C1-metabolism |
| 26 | misc |
| 27 | RNA |
| 28 | DNA |
| 29 | protein |
| 30 | signalling |
| 31 | cell |
| 32 | MicroRNA |
| 33 | development |
| 34 | transport |
| 35 | not assigned |

Figure 7:
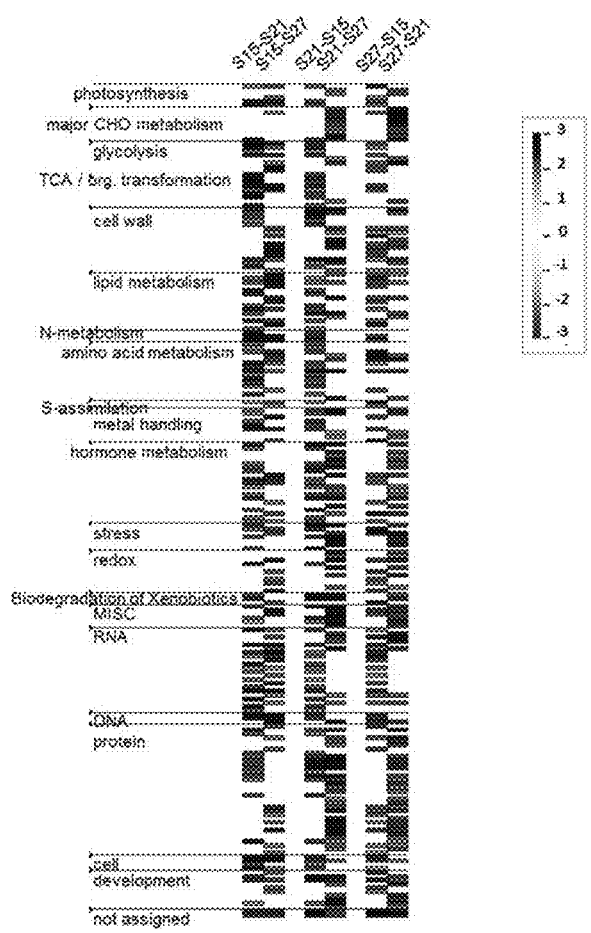
FIG. 7 shows the enriched functional categories in each of the pair-wise comparison. Each vertical column represents the genes that are dramatically up (blue) or down (red) regulated when comparing the 2 sampling times indicated at the top. Lines to the left show each functional category derived from the Mapman software. Each color bar represents an individual locus.

PageMan was used to obtain a statistics-based overview of enriched functional categories in each of the three pairwise comparisons (S15 vs. S21, S21 vs S27 and S27 vs S15) [80]. The transcriptome data were loaded into PageMan and a Wilcoxon test [81] was applied to each category. The Wilcoxon test compares the log base 2 fold change values of genes in a functional category against all genes not in that category. This reveals whether the genes in a particular category behave differently compared to all the other genes. This analysis condensed and compressed the genes by removing categories that did not show a significantly different change and displaying the categories that did show significant change using a false color heat-map-like display to show up- or down-regulated classes. Visual display of the Wilcoxon test results revealed enriched specific functional categories in each of the three pairwise comparisons (FIG. 7). Genes encoding enzymes for light independent photosynthetic reactions, glycolysis, TCA cycle, lipid metabolism, RNA and DNA synthesis and cellular functions are strongly up-regulated during the early stage of embryo maturation (S15). At 21 DAP, gene enrichment is shifted to functional categories that include cell wall, metal handling, hormone metabolism, stress, biodegradation of xenobiotics and synthesis of storage proteins. At the later stage of embryo maturation (S27), genes in almost all the functional categories are down-regulated with the exception of major carbohydrate metabolism, sulfur assimilation and subclasses of amino acid metabolism, RNA and protein.

Glycolysis

Figure 8:
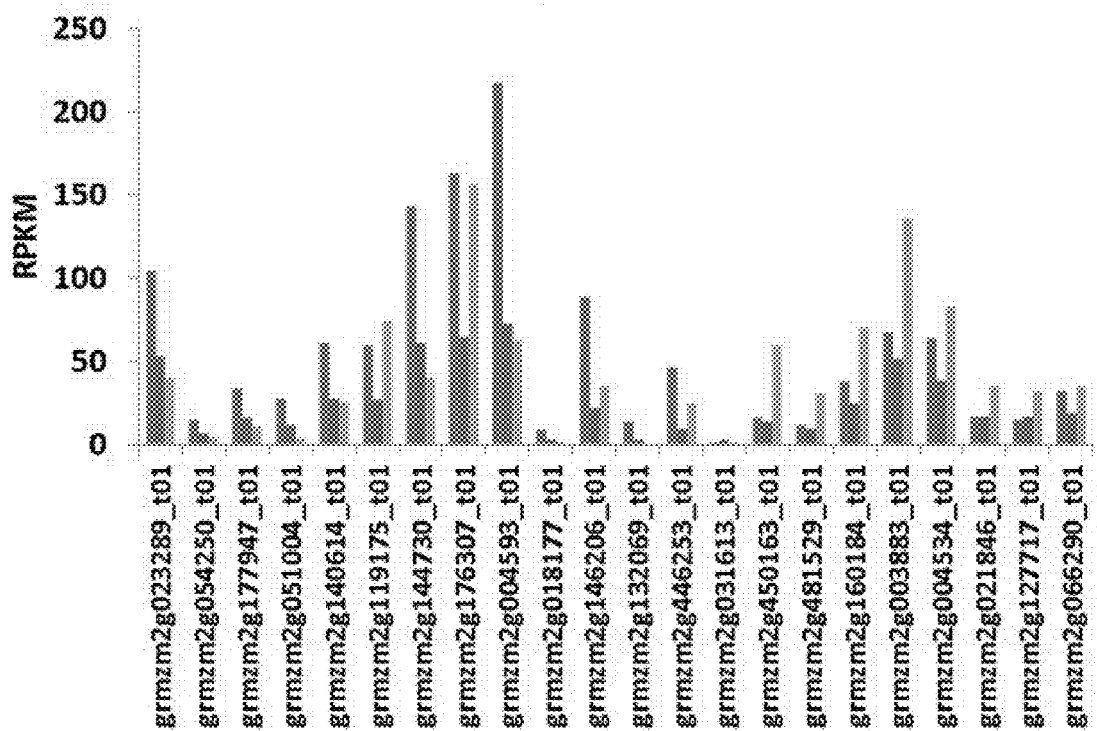
FIG. 8 shows the transcript profile of genes assigned to Glycolysis in maturing maize embryos. Each set of 3 vertical bars (blue, red, green) indicates the number of transcripts counted for the respective time points for the individual locus enumerated on the X-axis.
Figure 9:
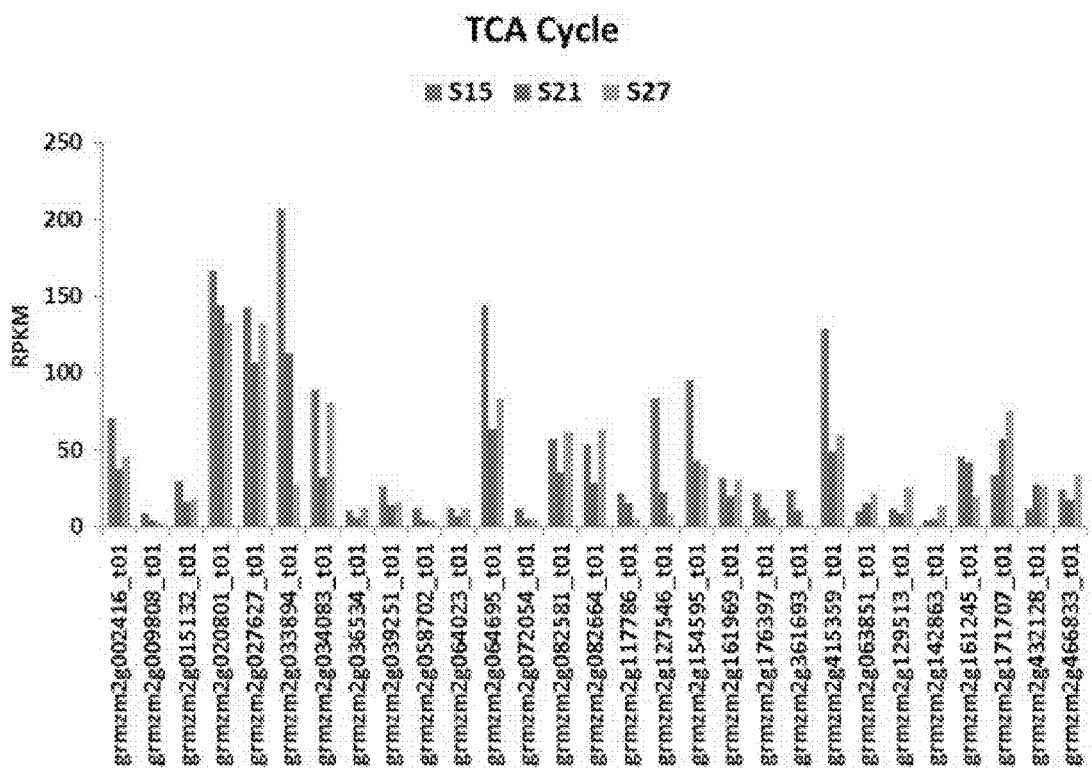
FIG. 9 shows the transcript profile of genes assigned to the TCA Cycle in maturing maize embryos. Each set of 3 vertical bars (blue, red, green) indicates the number of transcripts counted for the respective time points for the individual locus enumerated on the X-axis.

Glycolysis and the mitochondrial TCA cycle are important pathways in embryo maturation. They provide the energy required for active growth. Transcripts assigned to these two pathways showed two distinct groups of genes (FIG. 8 & FIG. 9). The first group had high expression during the early stage of embryo maturation and was characterized by high overall levels of transcript accumulation. The second group was up-regulated at 27 DAP and is characterized by much lower relative levels of transcript accumulation. Almost all the genes in glycolysis and the TCA cycle appeared to have minimal expression levels at 21 DAP (FIG. 8 & FIG. 9).

Lipid Metabolism

Figure 10:
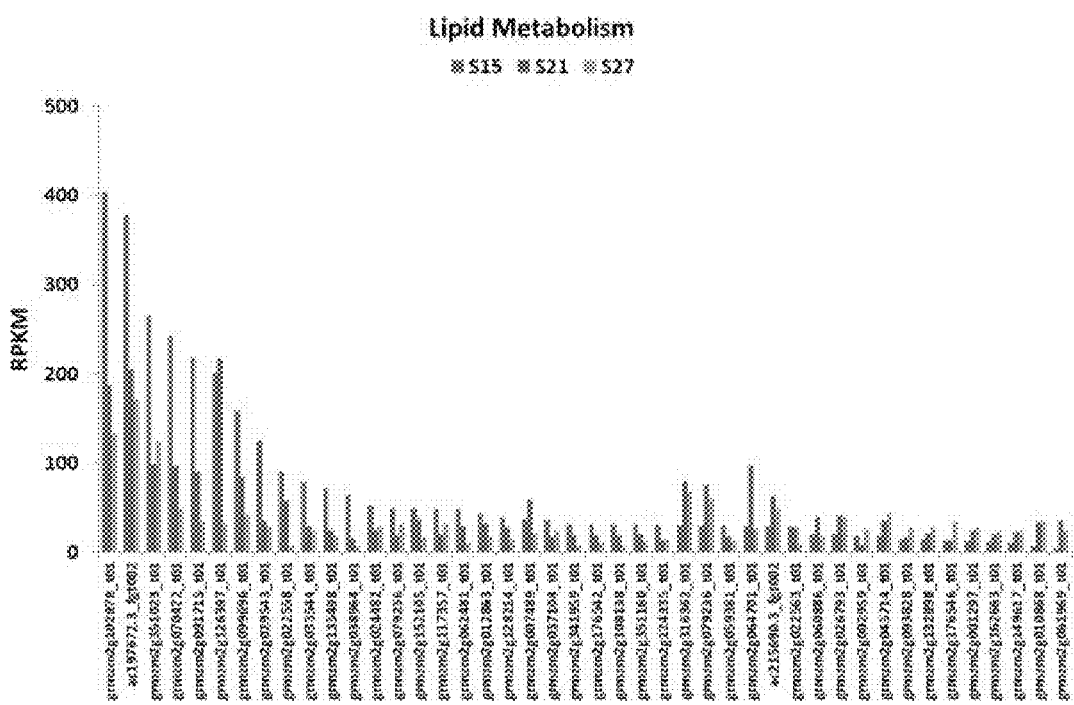
FIG. 10 shows the transcript profile of genes assigned to Lipid Metabolism in maturing maize embryos. Each set of 3 vertical bars (blue, red, green) indicates the number of transcripts counted for the respective time points for the individual locus enumerated on the X-axis.

The embryo is the site of active fatty acid production in the kernel. Lipids can accumulate at up to 50% of the dry weight of the maize embryo at maturation [82]. Active fatty acid biosynthesis occurs early in embryo maturation and continues to about 21 DAP. Three groups of genes are assigned to lipid metabolism (FIG. 10). The first comprises about 25 genes that are induced early during maturation. They are associated mainly with fatty acid synthesis and fatty acid elongation. This group is characterized by a higher overall transcript accumulation than the other two groups. A second smaller group of genes induced at 21 DAP comprises genes that encode a variety of enzymes associated with lipid modification such as ACP desaturases and biosynthesis of triacylglycerol (TAG). The third group of genes comprises a few that are associated with biosynthesis of sphingolipids, lipids derived from isoprenoids such as sterols and squalene, as well as with lipid degradation.

Figure 11:
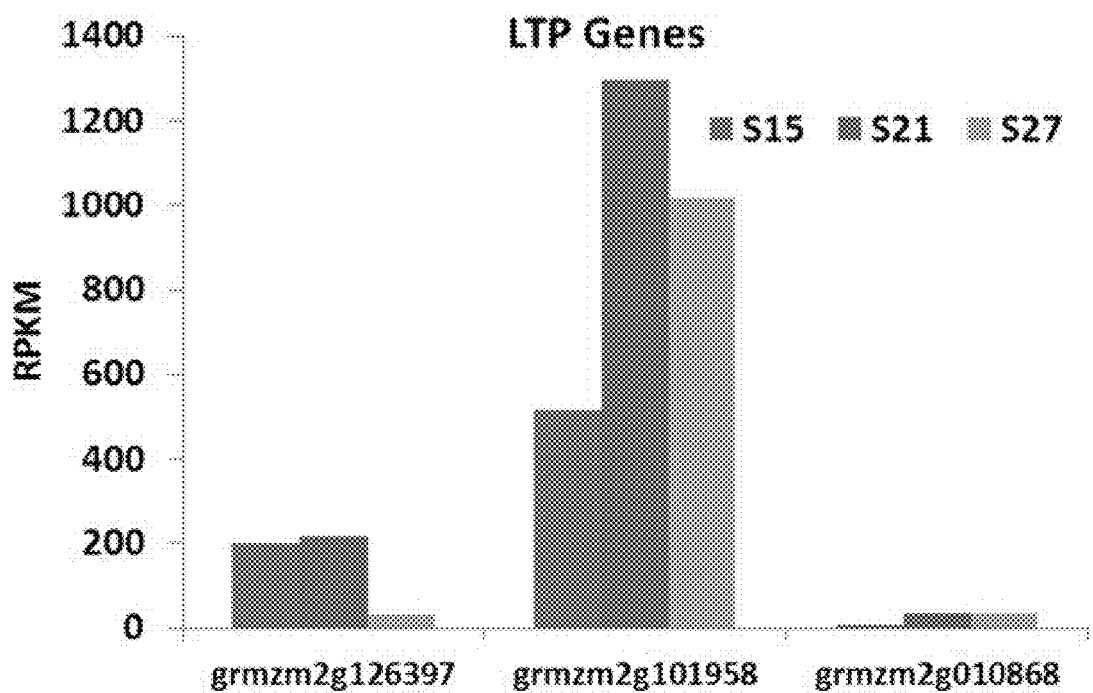
FIG. 11 shows the transcript profile of Lipid Transfer Protein genes in maturing maize embryos. Each set of 3 vertical bars (blue, red, green) indicates the number of transcripts counted for the respective time points for the individual locus enumerated on the X-axis.

Three genes are assigned to lipid transfer proteins (LTPs). Lipid transfer proteins have been shown to facilitate in vitro transfer of lipids between membranes and are assumed to play a role in membrane biogenesis [83]. Two of the genes, LTP1 and LTP2, are expressed at very high levels but their expression patterns are different from each other. The accumulation of the LTP1 transcript, grmzm2g126397_t01, was high at 15 DAP and continued through 21 DAP but dropped sharply by 27 DAP (FIG. 11). On the other hand, the accumulation of the LTP2 transcript, grmzm2g101958_t01, started at a high level at 15 DAP, increased dramatically at 21 DAP and maintained through 27 DAP. LTP3 is expressed at a low to moderate level and exhibited a similar expression pattern to LTP2.

DNA Synthesis

Figure 12:
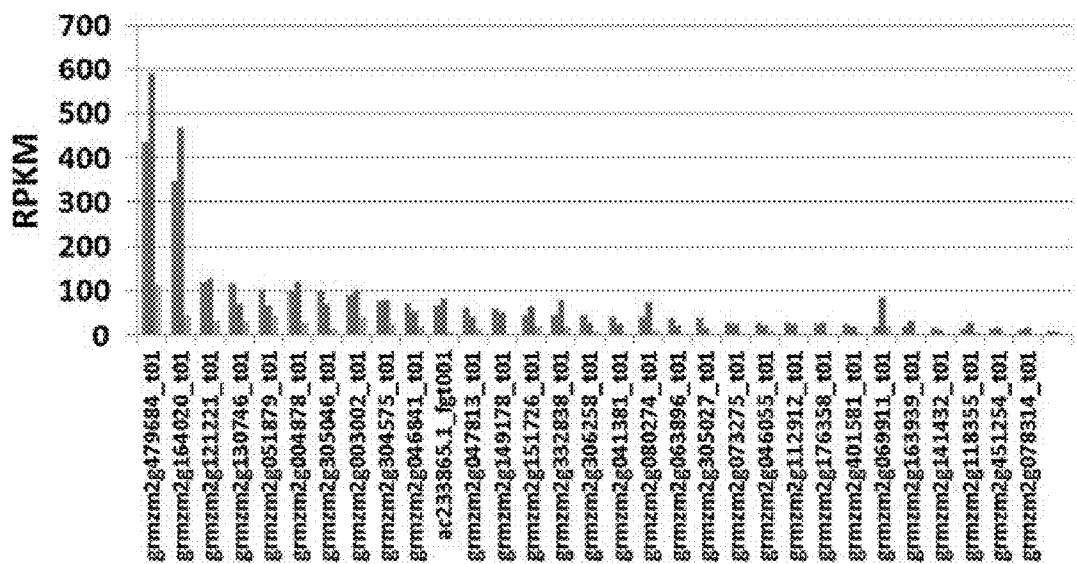
FIG. 12 shows the transcript profile of genes assigned to DNA Synthesis/Histone. Each set of 3 vertical bars (blue, red, green) indicates the number of transcripts counted for the respective time points for the individual locus enumerated on the X-axis.
Figure 13:
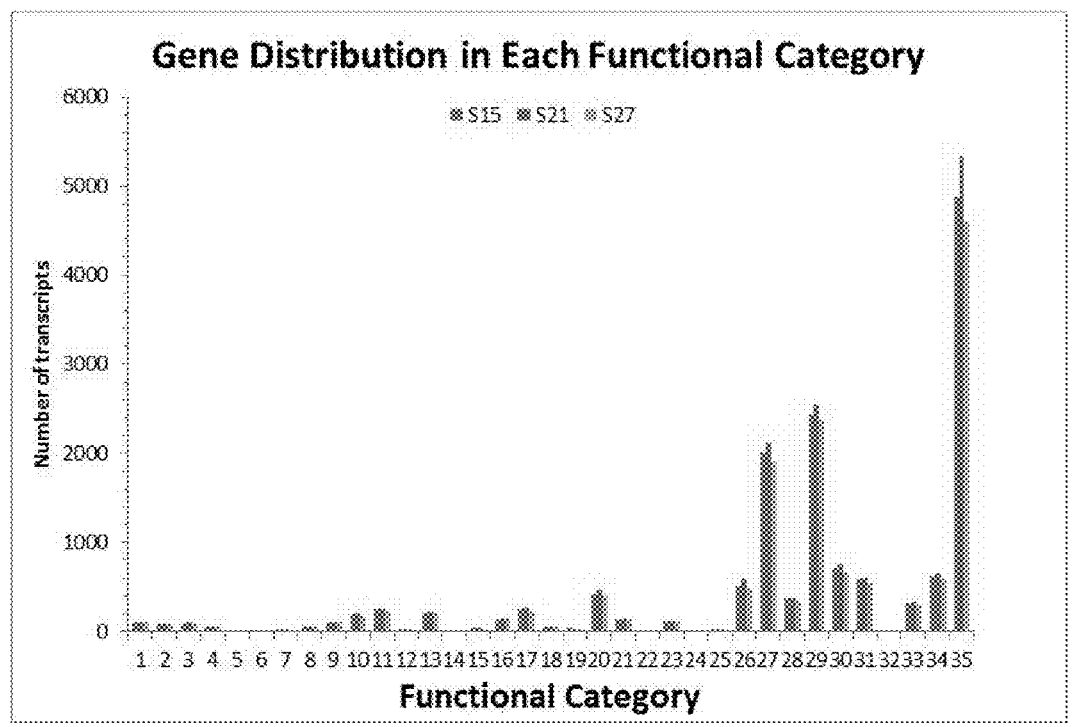
FIG. 13 shows the gene distribution in each functional category and number of transcripts detected.

DNA synthesis related genes such as those controlling chromatin structure and histone modification, are high in the early stages of embryo maturation (FIG. 12), reflected by the large number of genes and the relatively high level of their transcripts in the S15 and S21 embryos, either declining sharply by 27 DAP or in some cases no longer detected at all. A number of genes associated with chromatin structure showed high expression at 27 DAP (FIG. 13) but none are histone genes. Two histone genes, grmzm2g164020 and grmzm2g479684 that encode histone H1 and histone H4 respectively, are expressed at an exceptionally high level throughout the embryo maturation period in particular at 15 and 21 DAP (FIG. 12).

Development

Figure 14:
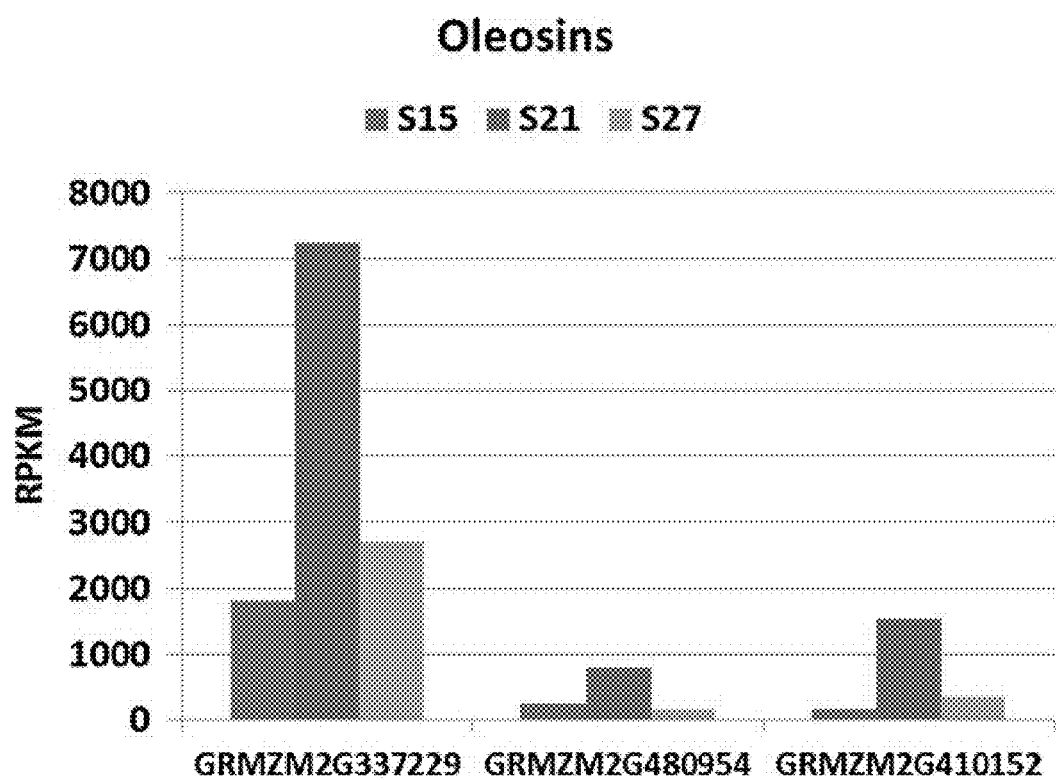
FIG. 14 shows the transcript profile of Oleosin genes in maturing maize embryos. Each set of 3 vertical bars (blue, red, green) indicates the number of transcripts counted for the respective time points for the individual locus enumerated on the X-axis.
Figure 15:
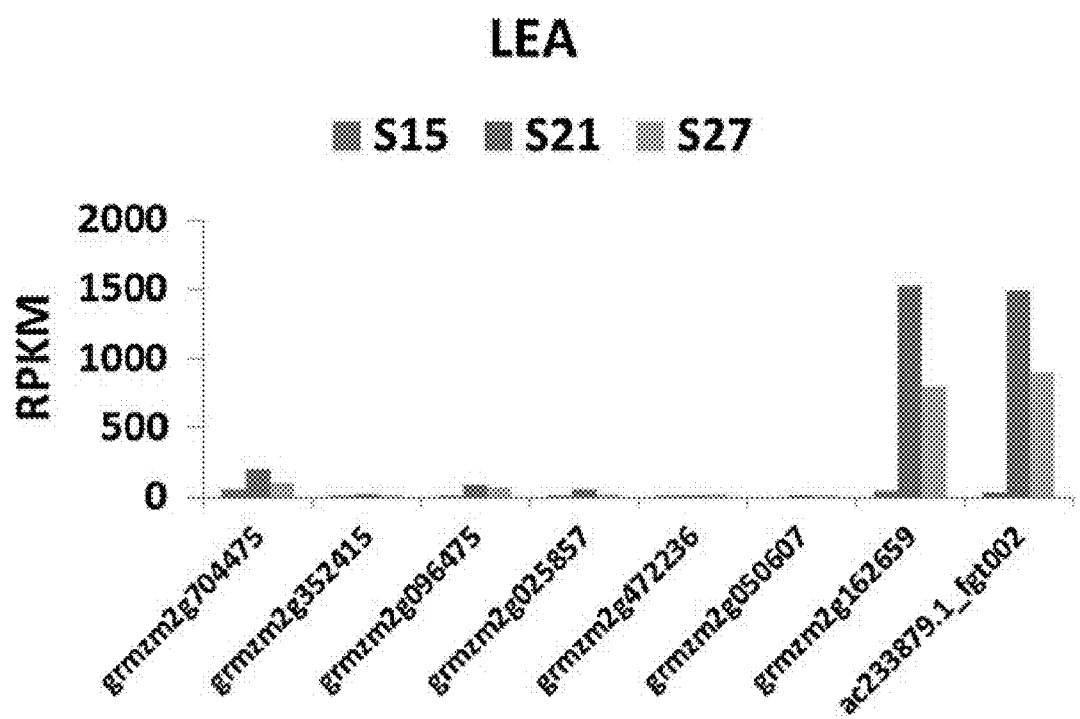
FIG. 15 shows the transcript profile of Late Embryogenesis Abundant genes in maturing maize embryos. Each set of 3 vertical bars (blue, red, green) indicates the number of transcripts counted for the respective time points for the individual locus enumerated on the X-axis.

Genes assigned to the development category code for storage proteins of the cupin family which include the globulin proteins, oleosins, and late embryogenesis abundant (LEA) proteins (FIGS. 5A&B, FIG. 14, and FIG. 15). In contrast to genes involved in DNA synthesis and cellular function, genes assigned to the development category showed low expression at 15 DAP, peaked at 21 DAP and then declined slightly as the embryos entered the later maturation stage. Transcripts of genes within this category accumulate to an exceptionally high level at 21 DAP.

Three prominent genes that encode storage proteins in the embryo, grmzm2g067919 (gib1), grmzm2g026703 (glb2) and grmzm2g078441, a gene in the cupin family of unknown function, are highly expressed (FIGS. 5A&B). The transcripts of these three genes taken together constitute about 99% of the transcripts of all storage protein genes. The globulin proteins are recognized as the major storage proteins in the mature embryo [64]. However, the transcriptome data suggest that their expression levels are not as high as grmzm2g078441. The transcript level of grmzm2g078441 even at its lowest (15 DAP) is higher than the peak levels of glb1 and glb2 (FIG. 5A). Because of our interest in embryo expression of foreign genes, we performed quantitative PCR to confirm the high levels of these critical genes from the transcriptome. As shown in FIG. 5B, expression level of the unknown cupin gene is 8-fold higher than glb-1 at 15 DAP, approximately equal at 21 DAP and 65% higher at 27 DAP. Although the qPCR results do not exactly mirror the transcriptome results, this unknown cupin gene holds interest for further analysis.

The oleosins represent the lipid storage proteins that are part of the structural unit of the single layer membrane surrounding lipid bodies in seed. Seven genes are assigned to the oleosins and three are highly represented in the maturing embryo transcriptome (FIG. 14). The most highly represented oleosin gene is grmzm2g337229 (oleosin 1), which at 21 DAP represents 75% of all the oleosin transcripts in the transcriptome.

Among the eight LEA genes in our transcriptome data, two stood out very prominently. These two LEA transcripts, grmzm2g162659_t01 and ac233879.1_fgt002, are homologs of *Arabidopsis* ATEM1 and ATEM6, respectively. These two LEA transcripts increased dramatically (30- to 50-fold) from 15 DAP to 21 DAP. The LEA transcripts have been shown to be inducible by abscisic acid (ABA) but do not require vp1 [84, 85]. The transcripts of the other LEA genes do not accumulate to a significant level (FIG. 15).

Gene Ontology

Figure 16:
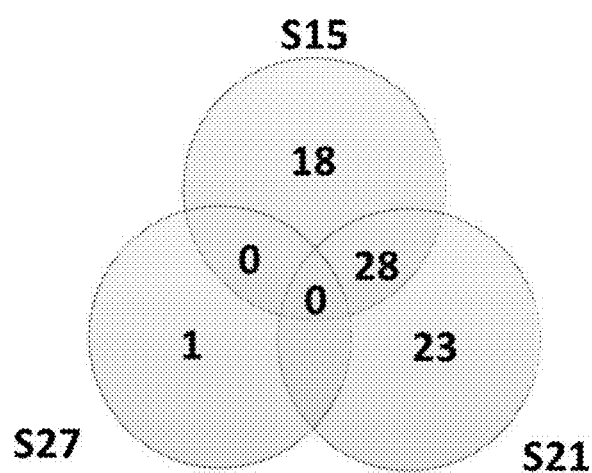
FIG. 16 shows the shared and Unique Gene Ontology Terms. S15=18 unique gene ontology terms; S21=23 unique gene ontology terms; S27=1 unique gene ontology term. There is no gene ontology term that is shared among all the three stages, between S15 and S27 and between S21 and S27.

Analysis of the Gene Ontology (GO) terms represented in the maize embryo transcripts revealed significantly over-represented GO terms that are unique to each of the embryo maturation stages as well as GO terms that are shared between S15 and S21 (FIG. 16). The most notably enriched GO terms that are unique to S15 are microtubule associated complex, microtubule motor activity, microtubule-based movement, motor activity, microtubule-based process, cytoskeletal part, fatty acid metabolic process, fatty acid biosynthetic process and lipid biosynthetic process. As for S21, the most notably unique GO terms are cellular components and cellular component organization, biological process and molecular functions associated with proteins such as protein oligomerization and protein-DNA complex assembly as well as GO terms associated with response to stress. There is only one GO term that is significantly enriched in S27 and that is nutrient reservoir activity. A list of the descriptions for the GO terms is presented in Table 6.

TABLE 6

GO terms found in embryo transcriptome.

| S15 | | S21 | | S27 | |
| --- | --- | --- | --- | --- | --- |
| GO ID | Description | GO ID | Description | GO ID | Description |
| GO: 0000786 | nucleosome | GO: 0000786 | nucleosome | GO: 0045735 | nutrient reservoir activity |
| GO: 0003677 | DNA binding | GO: 0001659 | temperature homeostasis | | |
| | | GO: 0003677 | DNA binding | | |
| | | GO: 0005198 | structural molecule activity | | |
| | | GO: 0005199 | structural constituent of cell wall | | |
| GO: 0003723 | RNA binding | | | | |
| GO: 0003774 | motor activity | | | | |
| GO: 0003777 | microtubule motor activity | | | | |
| GO: 0003824 | catalytic activity | | | | |
| GO: 0005634 | nucleus | GO: 0005634 | nucleus | | |
| GO: 0005875 | microtubule associated complex | | | | |
| GO: 0006260 | DNA replication | | | | |
| GO: 0006270 | DNA-dependent DNA replication initiation | | | | |
| GO: 0006325 | chromatin organization | GO: 0006325 | chromatin organization | | |
| GO: 0006334 | nucleosome assembly | GO: 0006334 | nucleosome assembly | | |
| GO: 0006631 | fatty acid metabolic process | | | | |
| GO: 0006633 | fatty acid biosynthetic process | | | | |
| GO: 0006996 | organelle organization | | | | |
| GO: 0007017 | microtubule-based process | | | | |
| GO: 0007018 | microtubule-based movement | | | | |
| GO: 0008150 | biological_process | GO: 0008150 | biological_process | | |
| GO: 0008610 | lipid biosynthetic process | GO: 0008898 | homocysteine S-methyltransferase activity | | |
| GO: 0016043 | cellular component organization | GO: 0009266 | response to temperature stimulus | | |
| GO: 0019219 | regulation of nucleobase, nucleoside, nucleotide and nucleic acid metabolism | GO: 0009409 | response to cold | | |

TABLE 6-continued

GO terms found in embryo transcriptome.

| S15 | | S21 | | S27 | |
|---|---|---|---|---|---|
| GO ID | Description | GO ID | Description | GO ID | Description |
| GO: 0022607 | cellular component assembly | GO: 0009628 | response to abiotic stimulus | | |
| GO: 0031323 | regulation of cellular metabolic process | GO: 0016043 | cellular component organization | | |
| GO: 0032501 | multicellular organismal process | GO: 0022607 | cellular component assembly | | |
| GO: 0032993 | protein-DNA complex | GO: 0032501 | multicellular organismal process | | |
| GO: 0034621 | cellular macromolecular complex subunit organization | GO: 0032993 | protein-DNA complex | | |
| GO: 0034622 | cellular macromolecular complex assembly | GO: 0034621 | cellular macromolecular complex subunit organization | | |
| GO: 0034728 | nucleosome organization | GO: 0034622 | cellular macromolecular complex assembly | | |
| GO: 0043227 | membrane-bounded organelle | GO: 0034660 | nc RNA metabolic process | | |
| GO: 0043231 | intracellular membrane-bounded organelle | GO: 0034728 | nucleosome organization | | |
| GO: 0043933 | macromolecular complex subunit organization | GO: 0042309 | homoiothermy | | |
| GO: 0044422 | organelle part | GO: 0042592 | homeostatic process | | |
| GO: 0044427 | chromosomal part | GO: 0043226 | organelle | | |
| GO: 0044430 | cytoskeletal part | GO: 0043227 | membrane-bounded organelle | | |
| GO: 0044446 | intracellular organelle part | GO: 0043229 | intracellular organelle | | |
| GO: 0050896 | response to stimulus | GO: 0043231 | intracellular membrane-bounded organelle | | |
| GO: 0051171 | regulation of nitrogen compound metabolic process | GO: 0043933 | macromolecular complex subunit organization | | |
| GO: 0051276 | chromosome organization | GO: 0044422 | organelle part | | |
| GO: 0065003 | macromolecular complex assembly | GO: 0044427 | chromosomal part | | |
| GO: 0065004 | protein-DNA complex assembly | GO: 0044446 | intracellular organelle part | | |
| GO: 0065007 | biological regulation | GO: 0048871 | multicellular organismal homeostasis | | |
| GO: 0071824 | protein-DNA complex subunit organization | GO: 0050824 | water binding | | |
| GO: 0071840 | cellular component organization or biogenesis | GO: 0050825 | ice binding | | |
| GO: 0071841 | cellular component organization or biogenesis at cellular level | GO: 0050826 | response to freezing | | |
| GO: 0071842 | cellular component organization at cellular level | GO: 0050896 | response to stimulus | | |
| GO: 0071844 | cellular component assembly at cellular level | GO: 0051259 | protein oligomerization | | |
| GO: 0080090 | regulation of primary metabolic process | GO: 0051260 | protein homooligomerization | | |
| | | GO: 0051276 | chromosome organization | | |
| | | GO: 0065003 | macromolecular complex assembly | | |
| | | GO: 0065004 | protein-DNA complex assembly | | |
| | | GO: 0065007 | biological regulation | | |
| | | GO: 0065008 | regulation of biological quality | | |
| | | GO: 0071824 | protein-DNA complex subunit organization | | |
| | | GO: 0071840 | cellular component organization or biogenesis | | |
| | | GO: 0071841 | cellular component organization or biogenesis at cellular level | | |
| | | GO: 0071842 | cellular component organization at cellular level | | |
| | | GO: 0071844 | cellular component assembly at cellular level | | |

Single Nucleotide Polymorphism (SNP) Discovery

Maize is generally considered highly polymorphic with a relatively high frequency of SNPs. The high frequency of SNPs coupled with improvements in sequencing technology and high throughput genotyping methods like DNA chips, allele-specific PCR and primer extension approaches, have made SNPs especially attractive as genetic markers [86] for discovering genes and identifying germplasm.

Table 7 shows the numbers of SNPs discovered per chromosome. The discovered SNPs and their context sequences are provided in Table 7. The highest numbers of SNPs lay in chromosomes 1 and 3 with 4,076 and 3,382 SNPs, respectively, whereas the lowest number of SNPs lays in chromosome 8 (717).

TABLE 7

Numbers of SNPs discovered per chromosome and per genotype via comparison to the reference genome

| Chr | S21 | (% total) |
|---|---|---|
| 0[1] | 76 | 0.4 |
| 1 | 4,076 | 20.3 |
| 2 | 1,664 | 8.3 |
| 3 | 3,382 | 16.9 |
| 4 | 1,926 | 9.6 |
| 5 | 1,586 | 7.9 |
| 6 | 1,945 | 9.7 |
| 7 | 2,116 | 10.6 |
| 8 | 717 | 3.6 |
| 9 | 1,136 | 5.7 |
| 10 | 1,408 | 7 |
| Total | 20,032 | |

[1]SNPs in sequences that have not been mapped to a chromosome.

Discussion

Transcriptomics is a powerful tool to analyze gene expression within any living system. The data generated in a single experiment will answer many questions about the system of interest. These data will also generate a host of new questions that can be explored in more detail using these same techniques on related samples. The drawback to this generation of megadata sets is that the analysis of the data requires large computing capability, multiple software packages and decisions based on value judgments about how to parse the data into package sizes that make sense and can be interpreted biologically.

The Mapman Pathway and Pageman programs have allowed us to observe changes in gene expression patterns that correlate with the maturing phases of the maize embryo. At 15 DAP, the embryo is at the transition between late development and early maturation, therefore many of the genes associated with the early events of embryo development are beginning to wane in their expression levels. For examples, genes encoding precursor biosynthesis (lipids, amino acids), DNA and RNA synthesis, as well as cell division and organization functions are more highly represented at 15 DAP than at later stages (FIG. 6). At 21 and 27 DAP which are firmly within the embryo maturation phase, gene expression for activities such as growth and build-up of reserves rose, while genes from the earlier phase dropped. These results are similar to those observed by Lee et al. [67] using microarray techniques. The advantage of transcriptomics over microarrays is the breadth of the discovery potential with RNA sequencing, in contrast to microarrays which are based on a limited number of gene sequences.

Almost 30% of the genes in this transcriptome do not have functions assigned to them. Many of these genes are unique to the specific stage of the embryo while others showed big differences in the level of expression in a pairwise comparison. Some of these uncategorized genes such as grmzm2g409101 and grmzm2g075042 are expressed at very high levels and are coordinately expressed with globulin-1 genes (data not shown). Further functional analysis will provide deeper insight into the roles these genes play in the maturation of the embryo or in the accumulation of storage proteins, roles that will be identified through mutations and network prediction and manipulation. This transcriptome data also showed that the total number of expressed genes was highest at 21 DAP and decreased as the embryos increased in maturity. This is in agreement with data published by Lee et al. [67] and Luo et al. [87] who showed accumulation of individual mRNAs during maize kernel development were much lower after 25 DAP. The 21 DAP embryo also represents a transition stage from 15 DAP to 27 DAP and a large number of genes were shared between 21 DAP and the other two stages. Davidson et al. [88] found 22,493 genes expressed in 25 DAP B73 embryos, very near the number that we discovered in maturing embryos from SP114.

The focus herein is upon several sets of genes to show the utility of our data in understanding the gene expression changes at specific time points of embryo maturation. For example, the 2 histone genes that encode histones H1 and H4 showed very high expression throughout maturation, suggesting a very important role for these two genes during this critical time. In contrast, the LEA genes have been proposed to play a role in desiccation tolerance [89, 90] which probably accounts for their increase in expression level later in embryo maturation. The accumulation of storage proteins in the maize embryo is also quite interesting because understanding the expression pattern of these genes may help understanding of how these genes are regulated. One of the most interesting observations relates to genes in the cupin family that encode storage proteins within the embryo. In the bio-factory experiments, the globulin-1 promoter was used [29] to drive expression of foreign genes for industrial enzyme production [58, 60]. The goal of the bio-factory production system is to increase foreign protein accumulation by as much as possible to lower the cost of production. Thus, the observation of a transcript in the cupin family, unknown gene grmzm2g078441 in FIGS. 5A&B, that shows significantly higher expression than the globulin-1 gene (grmzm2g067919) at 15 and 27 DAP, suggests that its promoter would be a more effective promoter for foreign gene expression. This is the major embodiment of the present invention. Belanger and Kriz [29] found glb-1 and 2 to be the most abundant proteins in the embryo. The question is why the cupin transcript appears to be expressed at a higher level than the globulins if this is the case. One explanation could be that the transcript does not produce a protein, but is a type of pseudo-gene. Another explanation is that the studies were performed on different types of maize, W64A and Va26 in the 1991 study, and SP114 in this study. In addition, globulins are produced by a multigene family and possibly were not fully accounted for by the alignment, whereas the cupin gene transcript could be higher, though the protein not as abundant. Each of these possibilities will be addressed in further studies.

"The GO project has developed three structured controlled vocabularies (ontologies) that describe gene products in terms of their associated biological processes, cellular components and molecular functions in a species-independent manner". This useful tool allows cross-species comparisons of gene functions because of the uniformity of gene annotation language. It also reduces complexity of gene expression categories to 3 functional categories in order to find unique functions in a particular transcriptome. A GO term that stands out as highly over-represented is notable for its activity and describes the basic functions going on at that particular time and place. When GO analysis was applied to the embryo maturation transcriptome, a few terms were found that were unique or shared at each stage (FIG. 16). These terms will drive some interesting analysis in the future.

Alexandrov et al. [69], through large scale sequencing of maize cDNAs, showed the distribution of mRNA characteristics associated with their promoters, transcriptional start site predictors, and GC content, especially in the third position of the codon. It would be interesting to understand if the genes expressed in a particular tissue at a particular time differ in their specific structural characteristics based on these authors' analysis. For example, groups of genes in one of the GC content modal groups may be preferred in one or another tissue or developmental event.

The results reported here provide a baseline for further studies on individual genes or groups of genes that will elucidate how a corn embryo matures and begins to shut down for dormancy. Results from those types of studies can be utilized to enhance genes that would improve yield for increased food or feed productivity. In this world of ever-increasing populations, such outcomes will be critical.

Conclusions

Numerous genes involved in embryo maturation have been identified, many of which show significant changes in expression level during the progression from 15 to 27 DAP. An expected array of genes involved in primary metabolism was identified. Of particular interest are the storage protein genes, globulin-1, globulin-2 and an unidentified cupin family gene. When expressing foreign proteins in maize, the globulin-1 promoter is most often used, but this cupin family gene has much higher expression and may be a better candidate for foreign gene expression in maize embryos. Results such as these allow identification of candidate genes and promoters that may not otherwise be available for use. The transcriptome data show patterns of expression of different genes involved in embryo development and storage protein accumulation. The transcriptome data will also serve as valuable resources for functional characterization of maize genes as more than 30% of transcripts represented un-annotated genes, leaving many functions to be discovered. As genes in *Arabidopsis* and other model systems are annotated, the identification of some of these novel genes will be accomplished.

Methods

Plant Materials and Growth Conditions

The maize (*Zea mays* L) inbred SP114 (U.S. Pat. No. 6,252,148 [71]) was grown in the greenhouse at the Arkansas Biosciences Institute in Metro Mix 200 (SunGro Horticulture, Bellevue, Wash.) soilless medium and fertilized with Osmocote. Temperature and light cycles were set at 27° C. to 31° C. for 16-h light and 20° C. to 24° C. for 8-h dark. The embryos were isolated at 15, 21 and 27 days after pollination (DAP) under aseptic conditions, frozen in liquid nitrogen and stored at −80° C. until used for RNA extraction.

RNA Extraction

The frozen embryos were ground into a fine powder in liquid nitrogen and homogenized in TRI Reagent solution (Ambion, Austin, Tex.). Total RNA at 15, 21 and 27 DAP was isolated following the RNA Isolation protocol from Invitrogen (Carlsbad, Calif.) and purified using Qiagen RNAeasy Mini Spin Columns (Qiagen, Valencia, Calif.). The concentration and purity of the total RNA were determined using an ND-1000 Spectrophotometer Nanodrop system (Thermo Scientific, Wilmington, Del.) as well as RNA gel electrophoresis (Formaldehyde buffer system).

cDNA Library Construction and Transcriptome Sequencing cDNA library construction and sequencing of the transcriptome were contracted to Tufts Core Facility at Tufts University School of Medicine, Boston, Mass. The cDNA libraries were constructed following the procedures outlined in the manufacturer's manual (Illumina, Inc, San Diego, Calif.). The sequencing of the transcriptome was done using the Illumina Genome Analyzer II/Solexa (Illumina, Inc, San Diego, Calif.). The cDNA library for the 21 DAP (S21) samples was run in a single Illumina flow cell lane while the cDNA libraries for 15 DAP (S15) and 27 DAP (S27) were each paired with a transgenic sample of the same age. The number of trimmed reads was 11.6 million for S15, 18.8 million for S21, and 15.4 million for S27. Single-end reads were obtained with ranges in length from 64 (S15 and S27) to 66 (S21) bases.

Alignment of Reads to the Genome and Data Analysis

Mapping of RNA-SEQ Reads

Raw reads were trimmed to remove low-quality nucleotides via a custom Data2Bio (Ames, Iowa) trimming script. GSNAP (Genomic Short-read Nucleotide Alignment Program, version 2010-07-37) [91], which allows for gapped alignments, including intron-spanning alignments, was used to map trimmed reads to the reference genome. Only reads with one unique best match in the reference genome and ≤2 mismatches every 36 bp, and ≤3 bp tails were used for subsequent analyses. The read depth of each gene was computed based on the coordinates of mapped reads and annotated locations of genes in the reference genome.

All reads were aligned to the reference genome for *Zea mays*, ZmB73AGPv1; Mitochondrian (AY506529.1) and Chloroplast (X8563.2). The alignment and initial analysis of the transcriptome data were done by Data2Bio (Ames, Iowa). Further analysis was conducted in-house using CLC Genomics Workbench (Cambridge, Mass.). Visualization of the mapping and pathways was carried out using publicly available software including Mapman [92] and Integrated Genomic Viewer (IGV) [93].

Identification of Differentially Expressed Genes Via Fisher's Exact Test

Normalization was conducted using a method that corrects for biases introduced by RNA composition and differences in the total numbers of mapped reads in the two samples [94]. Normalized read counts were used to calculate fold-changes (FC) and statistical significance. Fisher's exact test was used to test the null hypothesis that expression of a given gene is not different between the two samples. Only genes having at least 50 mapped reads from the two samples combined were tested. Genes identified as candidates for differential expression were further filtered by correcting for multiple testing [95] and a false discovery rate of 0.1% (q-value). Statistically significant variation can be a consequence of either biological or technical variation in gene expression between the two samples.

Gene Ontology (GO) Analysis

The software goatools was used to perform the GO analysis. Over- and under-representation of certain GO terms were determined based on Fisher's exact test. Two multiple correction controls (Bonferroni and permutation to control false discovery rate) [96] were implemented.

Single Nucleotide Polymorphism (SNP) Discovery

SNPs were called via comparisons to the reference genome, ZmB73AGPv1. Sequence variants identified by Genomic Short-read Nucleotide Alignment Program (GSNAP) were further filtered to identify SNPs using uniquely mapped reads. SNP sites were called if they have ≥3 reads supporting it, minimum SNP base quality value ≥15, and rare allele coverage among all the reads must exceed 0.8 which stringently controls false SNP discovery potentially derived from sequence errors and paralogs.

Real-Time PCR

To verify RNA-seq results, quantitative real-time PCR was conducted using SYBR green (Bio-Rad) and CFX384 Real-Time PCR detection system (Bio-Rad, Hercules, Calif.). SYBR® green primers for qPCR were designed using AlleleID® 7 software (Premier Biosoft, Palo Alto Calif.). To ensure target specificity gene sequences were blasted against non-redundant database (GenBank, NCBI) to determine cross homology with other sequences. Gene sequences were analyzed for secondary structures to avoid designing primers in these regions. Primers were designed to obtain a product between 75 and 200 bp. Primers were synthesized by Integrated DNA Technologies, Inc., San Diego, Calif. Two-step RT-qPCR was performed using SYBR Green detection chemistry. cDNA was synthesized from 1 μg of total RNA and oligo(dT) primers, using the iScript™ Select cDNA Synthesis kit (Bio-Rad), following the manufacturer's procedure. Quantitative real time PCR was carried out in a total volume of 5 uL containing 0.5 uL of template and 4.5 uL of master mix. The following amplification program was used: denaturation at 95° C. for 30 s, 40 cycles of amplification (95° C. for 10 s, 60° C. for 30 s) and a melting curve program (from 65° C. to 95° C., with an increment of 0.5° C. for 5 s). Three reference genes (Table 4) were used to normalize expression and these values were then compared to reads per kilobase of exon per million mapped reads (RPKM) estimates. All PCR reactions were done in triplicate on 384-well full-skirt PCR plates (USA Scientific, Ocala, Fla.).

Description of the Preferred Embodiments

Nucleotide sequences are described herein that regulate transcription with preferential expression to plant seed tissue, and preferential expression to plant embryo tissue in the seed. These novel nucleotide sequences are those natively associated with the nucleotide sequence upstream of the nucleotide sequence coding for Zea mays unclassified gene GRMZM2G078441 and comprise SEQ ID NO: 1 or SEQ ID NO: 3.

In one embodiment, the invention relates to an isolated DNA molecule comprising a plant promoter region, wherein the promoter region is selected from the group consisting of SEQ ID NO: 3 and variants thereof that are at least 95% identical to SEQ ID NO: 3, and a heterologous gene operably linked to the promoter. In one embodiment, the invention relates to an expression vector, comprising the DNA molecule described above (SEQ ID NO: 3 and variants thereof that are at least 95% identical to SEQ ID NO: 3, and a heterologous gene operably linked to the promoter). In one embodiment, the invention relates to a transgenic plant cell, comprising the DNA molecule described above (SEQ ID NO: 3 and variants thereof that are at least 95% identical to SEQ ID NO: 3, and a heterologous gene operably linked to the promoter). In one embodiment, the invention relates to a transgenic plant, comprising the DNA molecule described above (SEQ ID NO: 3 and variants thereof that are at least 95% identical to SEQ ID NO: 3, and a heterologous gene operably linked to the promoter). In one embodiment, the invention relates to a transgenic plant embryo, comprising the DNA molecule described above (SEQ ID NO: 3 and variants thereof that are at least 95% identical to SEQ ID NO: 3, and a heterologous gene operably linked to the promoter). In one embodiment, the invention relates to a plant gene expression cassette comprising, in sequence, a promoter region selected from the group consisting of SEQ ID NO: 3 and variants thereof that are at least 95% identical to SEQ ID NO: 3, the coding region of a heterologous gene and a 3' polyadenylation signal.

In one embodiment, the invention relates to a method for selectively expressing a nucleotide sequence in a plant embryo, the method comprising transforming a plant embryo with a transformation vector comprising an expression cassette, the expression cassette comprising a regulatory element and a heterologous nucleotide sequence operably linked to the regulatory element, said regulatory element comprising the sequence of SEQ ID NO: 3.

In one embodiment, the invention relates to a method of producing a protein of interest in a plant embryo, comprising: a) providing a transgenic embryo comprising a heterologous nucleic acid sequence encoding the protein of interest operably linked to a promoter region, wherein the promoter region is selected from the group consisting of SEQ ID NO: 3 and variants thereof that are at least 95% identical to SEQ ID NO: 3; and b) growing the plant under conditions such that the protein is produced in said embryo. In one embodiment, said embryo is a monocot. In one embodiment, said expression corresponds with the embryonic stage of plant development.

In one embodiment, the invention relates to an isolated DNA molecule comprising a plant promoter region, wherein the promoter region is selected from the group consisting of SEQ ID NO: 1 and variants thereof that are at least 95% identical to SEQ ID NO: 1, and a heterologous gene operably linked to the promoter. In one embodiment, the invention relates to an expression vector, comprising the DNA molecule described above (SEQ ID NO: 1 and variants thereof that are at least 95% identical to SEQ ID NO: 1, and a heterologous gene operably linked to the promoter). In one embodiment, the invention relates to a transgenic plant cell, comprising the DNA molecule described above (SEQ ID NO: 1 and variants thereof that are at least 95% identical to SEQ ID NO: 1, and a heterologous gene operably linked to the promoter). In one embodiment, the invention relates to a transgenic plant, comprising the DNA molecule described above (SEQ ID NO: 1 and variants thereof that are at least 95% identical to SEQ ID NO: 1, and a heterologous gene operably linked to the promoter). In one embodiment, the invention relates to a transgenic plant embryo, comprising the DNA molecule described above (SEQ ID NO: 1 and variants thereof that are at least 95% identical to SEQ ID NO: 1, and a heterologous gene operably linked to the promoter). In one embodiment, the invention relates to a plant gene expression cassette comprising, in sequence, a promoter region selected from the group consisting of SEQ ID NO: 1 and variants thereof that are at least 95% identical to SEQ ID NO: 1, the coding region of a heterologous gene and a 3' polyadenylation signal.

In one embodiment, the invention relates to a method for selectively expressing a nucleotide sequence in a plant embryo, the method comprising transforming a plant embryo with a transformation vector comprising an expression cassette, the expression cassette comprising a regulatory element and a heterologous nucleotide sequence operably linked to the regulatory element, said regulatory element comprising the sequence of SEQ ID NO 1.

In one embodiment, the invention relates to a method of producing a protein of interest in a plant embryo, comprising: a) providing a transgenic embryo comprising a heterologous nucleic acid sequence encoding the protein of interest operably linked to a promoter region, wherein the promoter region is selected from the group consisting of SEQ ID NO: 1 and variants thereof that are at least 95% identical to SEQ ID NO: 1; and b) growing the plant under conditions such that the protein is produced in said embryo. In one embodiment, said embryo is a monocot. In one embodiment, said expression corresponds with the embryonic stage of plant development.

A genomics approach can be used and is described to identify further sequences that can drive high levels of transgene expression in maize embryo tissues. The promoter sequences considered herein are shown in FIG. 17 and a shortened sequence is shown in FIG. 19. Promoter sequences are located near the transcription start sites of genes, on the same strand and upstream of the DNA that includes the sequences up to but not including the transcription start site. This is SEQ ID NO: 1 and includes the proximal approximately 3 kb of a maize unclassified gene GRMZM2G078441 promoter plus untranslated leader (also referred to as the "here cloned" promoter or regulatory region). Additionally the shortened sequence SEQ ID NO: 3 is a preferred promoter sequence. Transgenic plants generated using this sequence may show significantly increased expression of a recombinant protein. Furthermore, one of the new unclassified gene GRMZM2G078441 promoters plus untranslated leader sequence cloned here may be highly embryo preferred in its expression pattern. Thus, one of the new maize unclassified gene GRMZM2G078441 promoters plus untranslated leader sequence cloned here is well suited to drive transgene expression in maize and other plant seeds. The here cloned promoter may be particularly useful for the expression of gene sequences in cereal plants and especially in maize plants. However, it may be used in any plant species, including, for example, a monocotyledonous plant such as wheat, rye, rice, oat, barley, turfgrass, sorghum, millet or sugarcane. Alternatively, the plant may be a dicotyledonous plant, for example, tobacco, tomato, potato, soybean, cotton, canola, sunflower or alfalfa. Maize promoters have been used repeatedly to drive expression of genes in non-maize plants, including tobacco (Yang and Russell, 1990 [97]; Geffers et al., 2000 [98]; Vilardell et al., 1991 [99]), cultured rice cells (Vilardell et al., 1991 [99]), wheat (Oldach et al., 2001 [100]; Brinch-Pedersen et al., 2003 [101]), rice (Cornejo et al., 1993 [102]; Takimoto et al., 1994 [103]), sunflower (Roussell et al., 1988 [104]) and protoplasts of carrot (Roussell et al., 1988 [104]).

The nucleotide sequences of the invention can be used to isolate corresponding sequences from other organisms, particularly other plants, more particularly other monocots, or to synthesize synthetic sequences. In this manner, methods such as PCR, hybridization, synthetic gene construction and the like can be used to identify or generate such sequences based on their sequence homology to the sequences set forth herein. Sequences identified, isolated or constructed based on their sequence identity to the whole of or any portion of the maize unclassified gene GRMZM2G078441 promoter and untranslated leader sequences set forth herein (SEQ ID NO: 1 or SEQ ID NO: 3), and those that are distinct from other promoter and untranslated leader sequences previously reported are encompassed by the present invention. In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed (Sambrook et al., 1989 [105]; Innis et al., 1990 [106]; Innis et al., 1995 [107]; Innis et al., 1999 [108]). Known methods of PCR include, but are not limited to, methods using paired primers, nested primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the DNA sequences of the invention. Methods for preparation of probes for hybridization and for construction of cDNA and genomic libraries are generally known in the art and are disclosed (Sambrook et al., 1989 [105]).

For example, the proximal approximately 3 kb of a maize unclassified gene GRMZM2G078441 promoter plus untranslated leader (also referred to as the "here cloned" promoter or regulatory region) disclosed herein, or one or more portions thereof, may be used as a probe capable of specifically hybridizing to corresponding sequences. To achieve specific hybridization under a variety of conditions, such probes include sequences that are unique among the sequences to be screened and are preferably at least about 10 nucleotides in length, and most preferably at least about 20 nucleotides in length. Such sequences may alternatively be used to amplify corresponding sequences from a chosen plant by PCR. This technique may be used to isolate sequences from a desired plant or as a diagnostic assay to determine the presence of sequences in a plant. Hybridization techniques include hybridization screening of DNA libraries plated as either plaques or colonies (Sambrook et al., 1989 [105]).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1.0 M NaCl, 1% SDS at 37° C., and a wash in 0.1×SSC at 60 to 65° C.

Specificity is also the function of post-hybridization washes, the critical factors being the ionic strength and temperature of the final wash solution. For DNA-DNA hybrids, the $T_m$ can be approximated from the equation $T_m=81.5°$ C.+16.6 (log M)+0.41(% GC)−0.61(% form.)− 500/L, where M is the molarity of monovalent cations, % GC is the percentage of guanosine and cytosine nucleotides in the DNA, % form. is the percentage of formamide in the hybridization solution, and L is the length of the hybrid in base pairs (Meinkoth and Wahl, 1984 [109]). The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted for sequences of the desired identity to hybridize. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11 to 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Ausubel et al. (1993 [110]) and Sambrook et al. (1989 [105]).

Thus, isolated sequences that have promoter activity and which hybridize under stringent conditions to the promoter sequences disclosed herein, or to fragments thereof, are encompassed by the present invention.

The promoter of the invention may be combined with any number of other components to be introduced into the plant, including combined with a gene of interest to be expressed in the plant, provided the gene of interest is not the maize unclassified gene GRMZM2G078441. The "gene of interest" refers to a nucleotide sequence that encodes for a desired polypeptide or protein but also may refer to nucleotide sequences that do not constitute an entire gene, and which do not necessarily encode a polypeptide or protein. For example, when used in a homologous recombination process, the promoter may be placed in a construct with a sequence that targets and area of the chromosome in the plant but may not encode a protein. If desired, the gene of interest can be optimized for plant translation by optimizing the codons used for plants and the sequence around the translational start site for plants. Sequences resulting in potential mRNA instability can also be avoided.

The promoter of the invention may also be used in conjunction with another promoter. In one embodiment, the plant selection marker and the gene of interest can be both functionally linked to the same promoter. In another embodiment, the plant selection marker and the gene of interest can be functionally linked to different promoters. In yet third and fourth embodiments, the expression vector can contain two or more genes of interest that can be linked to the same promoter or different promoters. For example, the maize unclassified gene GRMZM2G078441 promoter described here can be used to drive the gene of interest and the selectable marker, or a different promoter used for one or the other. These other promoter elements can be those that are constitutive or sufficient to render promoter-dependent gene expression controllable as being cell-type specific, tissue-specific or time or developmental stage specific, or being inducible by external signals or agents. Such elements may be located in the 5' or 3' regions of the gene. Although the additional promoter may be the endogenous promoter of a structural gene of interest, the promoter can also be a foreign regulatory sequence. Promoter elements employed to control expression of product proteins and the selection gene can be any plant-compatible promoters. These can be plant gene promoters, such as, for example, the ubiquitin promoter (European patent application no. 0 342 926 [111]); the promoter for the small subunit of ribulose-1,5-bis-phosphate carboxylase (ssRUBISCO) (Coruzzi et al., 1984 [112]; Broglie et al., 1984 [113]); or promoters from the tumor-inducing plasmids from *Agrobacterium tumefaciens*, such as the nopaline synthase, octopine synthase and mannopine synthase promoters (Velten and Schell, 1985 [114]) that have plant activity; or viral promoters such as the cauliflower mosaic virus (CaMV) 19S and 35S promoters (Guilley et al., 1982 [26]; Odell et al., 1985 [115]), the figwort mosaic virus FLt promoter (Maiti et al., 1997 [116]) or the coat protein promoter of TMV (Grdzelishvili et al., 2000 [117]). Alternatively, plant promoters such as heat shock promoters for example soybean hsp 17.5-E (Gurley et al., 1986 [118]); or ethanol-inducible promoters (Caddick et al., 1998 [119]) may be used. See International Patent Application No. WO/1991/019806 [120] for a review of illustrative plant promoters suitably employed in the present invention.

A promoter can additionally comprise other recognition sequences generally positioned upstream or 5' to the TATA box, referred to as upstream promoter elements, which influence the transcription initiation rate. It is recognized that having identified the nucleotide sequences for the promoter region disclosed herein, it is within the state of the art to isolate and identify further regulatory elements in the 5' region upstream from the particular promoter region identified herein. Thus the promoter region disclosed herein is generally further defined by comprising upstream regulatory elements such as those responsible for tissue and temporal expression of the coding sequence, enhancers and the like. In the same manner, the promoter elements, which enable expression in the desired tissue such as the embryo can be identified, isolated, and used with other core promoters to confirm embryo-preferred expression. By core promoter is meant the sequence sometimes referred to as the TATA box (or similar sequence), which is common to promoters in all genes encoding proteins. Thus the upstream promoter of the maize unclassified gene GRMZM2G078441 can optionally be used in conjunction with its own or core promoters from other sources, provided they are not combined with the maize unclassified gene GRMZM2G078441.

In general, the methods available for construction of recombinant genes, optionally comprising various modifications for improved expression, can differ in detail. However, conventionally employed methods include PCR amplification, or the designing and synthesis of overlapping, complementary synthetic oligonucleotides, which are annealed and ligated together to yield a gene with convenient restriction sites for cloning, or subcloning from another already cloned source, or cloning from a library. The methods involved are standard methods for a molecular biologist (Sambrook et al., 1989 [105]).

One skilled in the art readily appreciates that the promoter can be used with any of a variety of nucleotide sequences comprising the gene of interest to be expressed in plants. For example, the gene of interest may encode a protein that is useful for industrial or pharmaceutical purposes or the like, or to impact the plant itself, such as through expression of a protein that provides disease resistance, insect resistance, herbicide resistance, or impacts agronomic traits as well as grain quality traits. The sequences used with the promoter can be native or non-native sequences to the plant. DNA sequences native to plants as well as non-native DNA sequences can be transformed into plants and used to modulate levels of native or non-native proteins.

The gene of interest can also be a nucleotide sequence used to target an area of the plant genome through homologous recombination. The promoter may be placed in a construct with such sequence, which sequence will not necessarily encode a protein. The sequence recombines in the genome and the promoter may be placed at the desired site targeted by the sequences to regulate the desired endogenous nucleotide sequence.

Further, the promoter can be used to drive mRNA that can be used for a silencing system, such as antisense, and in that instance, no protein is produced. Means of increasing or inhibiting a protein are well known to one skilled in the art and, by way of example, may include, transgenic expression, antisense suppression, co-suppression methods including but not limited to: RNA interference, gene activation or suppression using transcription factors and/or repressors, mutagenesis including transposon tagging, directed and site-specific mutagenesis, chromosome engineering and, homologous recombination. In the case of use with homologous recombination, no in vivo construct will be required. Once the gene is engineered to contain desired features, such as the desired subcellular localization sequences, it may then be placed into an expression vector by standard methods. The selection of an appropriate expression vector will depend upon the method of introducing the expression vector into host cells. A typical expression vector contains prokaryotic DNA elements coding for a bacterial origin of replication and an antibiotic resistance gene to provide for the growth and selection of the expression vector in the bacterial host; a cloning site for insertion of an exogenous DNA sequence; eukaryotic DNA elements that control initiation of transcription of the exogenous gene (such as the promoter of the invention or another promoter); and DNA elements that control the processing of transcripts, such as transcription termination/polyadenylation sequences. It also can contain such sequences as are needed for the eventual integration of the vector into the plant chromosome.

Clearly, many variations in use of the promoter of the invention are available to one skilled in the art.

In one embodiment, the expression vector also contains a gene encoding a selectable or scoreable marker that is operably or functionally linked to a promoter that controls transcription initiation, which can be the promoter of the invention or another promoter. By "operably linked" it is understood that the gene of interest (in this case the gene encoding a selectable or scoreable marker) is oriented in connection to the gene such that the promoter initiates transcription of the gene in order to allow its expression of the resulting protein in plants. For a general description of plant expression vectors and reporter genes, see Gruber et al. (1993) [121]. In one embodiment, the selective gene is a glufosinate-resistance encoding DNA and in another embodiment it can be phosphinothricin acetyl transferase (pat) or a maize optimized pat gene under the control of the CaMV 35S promoter. Such pat genes confer resistance to the herbicide bialaphos (Gordon-Kamm et al., 1990 [122]).

The expression vector can optionally also contain a signal sequence located between the promoter and the gene of interest. A signal sequence is a nucleotide sequence, translated to give an amino acid sequence, which is used by a cell to direct the protein or polypeptide of interest to be placed in a particular place within or outside the eukaryotic cell. One example of a plant signal sequence is the barley α-amylase secretion signal (Rogers, 1985 [123]). Many signal sequences are known in the art. See, for example Becker et al. (1992) [124], Fontes et al. (1991) [125], Matsuoka and Nakamura (1991) [126], Gould et al. (1989) [127], Creissen et al. (1992) [128], Kalderon et al. (1984) [129] and Stiefel et al. (1990) [130].

Leader sequences can be included to enhance translation. Instead of, or in addition to the untranslated leader sequence of the globulin-1 promoter, other leader sequences may be substituted or added. Translation leaders are known in the art and include: picomavirus leaders, for example, EMCV leader (Encephalomyocarditis 5' noncoding region) (Elroy-Stein et al. (1989) [131]; potyvirus leaders, for example, TEV leader (Tobacco Etch Virus) (Gallie et al. (1995) [132]); human immunoglobulin heavy-chain binding protein (BiP) (Macejak et al. (1991) [133]); untranslated leader from the coat protein mRNA of alfalfa mosaic virus (AMV RNA 4) (Jobling et al. (1987) [134]); tobacco mosaic virus leader (TMV); and maize chlorotic mottle virus leader (MCMV) (Lommel et al. (1991) [135]). See also, Della-Cioppa et al. (1987) [136]. Other methods known to enhance translation can also be utilized, for example, introns, and the like. Obviously, many variations on the promoters, selectable markers, signal sequences, leader sequences, termination sequences, introns, enhancers and other components of the construct are available to one skilled in the art.

Methods for introducing expression vectors into plant tissue available to one skilled in the art are varied and will depend on the plant selected. Procedures for transforming a wide variety of plant species are well known and described throughout the literature. See, for example, Mild and McHugh (2004) [137]; Klein et al. (1992) [138]; and Weising et al. (1988) [139]. For example, the DNA construct may be introduced into the genomic DNA of the plant cell using techniques such as microprojectile-mediated delivery (Klein et al. 1992 [138]), electroporation (Fromm et al., 1985 [140]), polyethylene glycol (PEG) precipitation (Mathur and Koncz, 1998 [141]), direct gene transfer (WO/1985/001856 [142]), in vitro protoplast transformation (U.S. Pat. No. 4,684,611 [143]) and microinjection of plant cell protoplasts or embryogenic callus (Crossway, 1985 [144]). Co-cultivation of plant tissue with Agrobacterium tumefaciens is another option, where the DNA constructs are placed into a binary vector system (Ishida et al., 1996 [145]). The virulence functions of the Agrobacterium tumefaciens host will direct the insertion of the construct into the plant cell DNA when the cell is infected by the bacteria. See, for example, Fraley et al. (1983) [146].

Standard methods for transformation of canola are described by Moloney et al. (1989) [147]. Corn transformation is described by Fromm et al. (1990) [140] and Gordon-Kamm et al. (1990) [122]. Agrobacterium is primarily used in dicots, but certain monocots such as maize can be transformed by Agrobacterium. See, for example, U.S. Pat. No. 5,550,318 [148]. Rice transformation is described by Hiei et al. (1994)[149] and Lee et al. (1991) [150]. Wheat can be transformed by techniques similar to those used for transforming corn or rice. Sorghum transformation is described by Casas et al. (1993) [151] and barley transformation is described by Wan and Lemaux (1994) [152]. Soybean transformation is described in a number of publications, including U.S. Pat. No. 5,015,580 [153].

In one preferred method, the Agrobacterium transformation methods of Ishida et al. (1996) [145] and also described in U.S. Pat. No. 5,591,616 [154], are generally followed, with modifications that the inventors have found improve the number of transformants obtained. The Ishida method uses the A188 variety of maize that produces Type I callus in culture. In one preferred embodiment, the Hi II maize line is used which initiates Type II embryogenic callus in culture (Armstrong et al., 1991 [155]).

While Ishida recommends selection on phosphinothricin when using the bar or pat gene for selection, another preferred embodiment provides use of bialaphos instead. In general, as set forth in the U.S. Pat. No. 5,591,616 [154], and as outlined in more detail below, dedifferentiation is obtained by culturing an explant of the plant on a dedifferentiation-inducing medium for not less than seven days, and the tissue during or after dedifferentiation is contacted with Agrobacterium having the gene of interest. The cultured tissue can be callus, an adventitious embryo-like tissue or suspension cells, for example. In this preferred embodiment, the suspension of Agrobacterium has a cell population of $10^6$ to $10^{11}$ cells/ml and are contacted for three to ten minutes with the tissue, or continuously cultured with Agrobacterium for not less than seven days. The Agrobacterium can contain plasmid pTOK162, with the gene of interest between border sequences of the T region of the plasmid, or the gene of interest may be present in another plasmid-containing *Agrobacterium*. The virulence region may originate from the virulence region of a Ti plasmid or Ri plasmid. The bacterial strain used in the Ishida protocol is LBA4404 with the 40 kb super binary plasmid containing three vir loci from the hypervirulent A281 strain. The plasmid has resistance to tetracycline. The cloning vector cointegrates with the super binary plasmid. Since the cloning vector has an *E. coli* specific replication origin, but not an *Agrobacterium* replication origin, it cannot survive in *Agrobacterium* without cointegrating with the super binary plasmid. Since the LBA4404 strain is not highly virulent, and has limited application without the super binary plasmid, the inventors have found in yet another embodiment that the EHA101 strain is preferred. It is a disarmed helper strain derived from the hypervirulent A281 strain. The cointegrated super binary/cloning vector from the LBA4404 parent is isolated and electroporated into EHA101, selecting for spectinomycin resistance. The plasmid is isolated to assure that the EHA101 contains the plasmid. EHA101 contains a disarmed pTi that carries resistance to kanamycin. See, Hood et al. (1986) [156].

Further, the Ishida protocol as described provides for growing fresh culture of the *Agrobacterium* on plates, scraping the bacteria from the plates, and resuspending in the co-culture medium as stated in the U.S. Pat. No. 5,591,616 [154] for incubation with the maize embryos. This medium includes 4.3 g MS salts, 0.5 mg nicotinic acid, 0.5 mg pyridoxine hydrochloride, 1.0 ml thiamine hydrochloride, casamino acids, 1.5 mg 2,4-D, 68.5 g sucrose and 36 g glucose per liter, all at a pH of 5.8. In a further preferred method, the bacteria are grown overnight in a 1 ml culture and then a fresh 10 ml culture is re-inoculated the next day when transformation is to occur. The bacteria grow into log phase, and are harvested at a density of no more than $OD_{600}=0.5$, preferably between 0.2 and 0.5. The bacteria are then centrifuged to remove the media and resuspended in the co-culture medium. Since Hi II is used, medium preferred for Hi II is used. This medium is described in considerable detail by Armstrong and Green (1985) [155]. The resuspension medium is the same as that described above. All further Hi II media are as described in Armstrong and Green (1985) [155]. The result is redifferentiation of the plant cells and regeneration into a plant. Redifferentiation is sometimes referred to as dedifferentiation, but the former term more accurately describes the process where the cell begins with a form and identity, is placed on a medium in which it loses that identity, and becomes "reprogrammed" to have a new identity. Thus the scutellum cells become embryogenic callus.

In accordance with the present invention, a transgenic plant is produced that contains an introduced globulin-1 promoter. It can be combined with any one of the components set forth above. In a preferred embodiment, the promoter is driving expression of a nucleotide sequence such that the sequence encodes a protein preferentially expressed in the seed of the plant. Preferably, the plant is a cereal plant, and most preferably, a maize plant.

In a further embodiment, plant breeding can be used to introduce the nucleotide sequences into other plants once transformation has occurred. This can be accomplished by any means known in the art for breeding plants such as, for example, cross pollination of the transgenic plants that are described above with other plants, and selection for plants from subsequent generations which express the amino acid sequence. The plant breeding methods used herein are well known to one skilled in the art. For a discussion of plant breeding techniques, see Poehlman and Sleper (1995) [157]. Many crop plants useful in this method are bred through techniques that take advantage of the plant's method of pollination. A plant is self-pollinating if pollen from one flower is transferred to the same or another flower of the same plant. A plant is cross-pollinating if the pollen comes from a flower on a different plant. For example, in *Brassica*, the plant is normally self-sterile and can only be cross-pollinated unless, through discovery of a mutant or through genetic intervention, self-compatibility is obtained. In self-pollinating species, such as rice, oats, wheat, barley, peas, beans, soybeans, tobacco and cotton, the male and female plants are anatomically juxtaposed. During natural pollination, the male reproductive organs of a given flower pollinate the female reproductive organs of the same flower. Maize plants (*Zea mays* L.) can be bred by both self-pollination and cross-pollination techniques. Maize has male flowers, located on the tassel, and female flowers, located on the ear, on the same plant. It can self or cross-pollinate.

Pollination can be by any means, including but not limited to hand, wind or insect pollination, or mechanical contact between the male fertile and male sterile plant. For production of hybrid seeds on a commercial scale in most plant species pollination by wind or by insects is preferred. Stricter control of the pollination process can be achieved by using a variety of methods to make one plant pool male sterile, and the other the male fertile pollen donor. This can be accomplished by hand detasslling, cytoplasmic male sterility, or control of male sterility through a variety of methods well known to the skilled breeder. Examples of more sophisticated male sterility systems include those described by Brar et al., U.S. Pat. No. 4,654,465 [158] and U.S. Pat. No. 4,727,219 [159] and Albertsen et al., U.S. Pat. No. 5,859,341 [160] and U.S. Pat. No. 6,013,859 [161].

Backcrossing methods may be used to introduce the gene into the plants. This technique has been used for decades to introduce traits into a plant. An example of a description of this and other plant breeding methodologies that are well known can be found in references such as Neal (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

Thus, specific compositions and methods of regulatory sequence of cupin family gene have been disclosed. It should be apparent, however, to those skilled in the art that many more modifications besides those already described are possible without departing from the inventive concepts herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims. The entire disclosures of all applications, patents, and publications cited above, and of the corresponding application are hereby incorporated by reference.

EXAMPLES

The following examples are provided in order to demonstrate and further illustrate certain preferred embodiments and aspects of the present invention and are not to be construed as limiting the scope thereof.

In the examples which follow, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); I or L (liters); ml (milliliters); µl (microliters); cm (centimeters); mm (millimeters); µm (micrometers); nm (nanometers); and ° C. (degrees Centigrade).

Example 1

Isolating and Utilizing a Maize Cupin Family Promoter for Recombinant DNA Technology The goal of this example research is to isolate and clone a cupin family promoter [SEQ ID NO: 1 or the shortened sequence SEQ ID NO: 3] that has been shown to express genes at higher levels than the currently used globulin-1 and globulin-2 promoters. A promoter is typically a region of DNA (about 2000 base pairs) that lies upstream of a gene. It signals to polymerases where to begin transcription of the genetic code into RNA—the template of protein synthesis. It follows from this that the stronger the promoter, the more highly the gene following it is expressed. Currently, the researchers use the globulin promoters to express foreign cellulases, which metabolize cellulose into monomers of glucose. The discovery of an unknown promoter that increased transcription 8-fold suggests that it is a much better candidate to maximize cellulase production in maize tissue. The production of glucose from cellulose is the basis of biomass conversion and is a promising technique for the future of renewable biofuels. If we maximize the amount of cellulase produced in plant tissue with this strong promoter, less biomass can be used to produce the enzyme and the cost of the process is dramatically reduced.

Objectives.
  Amplify and isolate the cupin promoter with polymerase chain reaction
  Create a plasmid vector with the promoter and a reporter gene that will allow for quantitative analysis of the promoter's activity
  Move the reporter gene and promoter to an *A. tumefaciens* plasmid that we will use to perform transient transformation of maize tissue
  Make stable maize transformants to confirm the transient results.

Experimental Methods
Objective 1: amplify and clone the cupin gene promoter. Rationale: to isolate and clone the sequence into a plasmid vector in *E. coli*.
Methods: The first objective of this research is to amplify the cupin promoter from maize DNA via polymerase chain reaction (PCR). Four "ingredients" are necessary for PCR. DNA polymerase from a thermophilic bacterium carries out synthesis of a new DNA strand in much the same way as in normal DNA replication in a living system. Primers, which are short sequences of DNA on each end of the PCR target region that signal to the polymerase where to begin and end replication, must be present in the reaction to prime the DNA polymerase. Since we know the sequence of most of the maize genome, the nucleotide sequence of the cupin family gene's promoter can be used to predict primers and the primers purchased. Template DNA, extracted from maize tissue with a Genomic DNA Isolation kit from Promega, and free deoxyribonucleoside triphosphates are also added to the PCR mix. During a polymerase chain reaction, added heat separates the strands of the template maize DNA, primers attach at a lower annealing temperature, DNA polymerase uses free monomers to assemble a complementary strand, starting at the first primer and detaching at the second. The process repeats until one "ingredient" is depleted, accumulating copies of target DNA at an exponential rate.

The primers purchased and put in the PCR mix have specific restriction sites designed onto their ends—locations where restriction enzymes cut the strand. The amplified promoter obtained from PCR will be digested with restriction enzymes and cloned into the pSK Blue Script vector from Invitrogen, which has the same restriction sites as the amplified promoter. The strands are cut at the specified locations and the "sticky" ends will spontaneously anneal with the help of T4 ligase, creating a vector containing pSK Blue Script and the cupin promoter.
Outcome: This plasmid is pRR01, the cupin promoter clone.
Objective 2: Place the cupin promoter upstream of a reporter gene, β-glucuronidase and prepare it for plant transformation. Rationale: In order to test the function of the promoter, a reporter gene must be aligned downstream of it and the construct put into a transformation-competent bacterial strain.
Methods: The second objective is to fuse the promoter to the reporter gene β-glucuronidase (GUS), whose enzymatic activity stains blue in transformed cells. This is achieved by digesting pRRO1 and a pSB1 vector that contains GUS and matching restriction sites. The pieces of each plasmid are run next to each other on an agarose gel. Using a Qiagen kit, the appropriate bands are purified after removing them from the gel. The bands corresponding to the isolated cupin promoter from pRRO1 and the opened pSB1 vector containing GUS are ligated to each other using T4 DNA ligase, producing what we will call pRR02, the plasmid vector that contains the cupin promoter followed by GUS. pRR02 is then inserted into an *E. coli* plasmid that includes a plant selective marker, like resistance to a certain drug or herbicide. Our *E. coli* plasmid donates the cupin promoter:GUS gene to *Agrobacterium tumefaciens* through a triparental mating.
Outcome: pRR02, a plasmid that contains the cupin promoter:GUS construct and a plant selectable marker in a plant transformation bacterium, *A. tumefaciens*.
Objective 3: Test the function of the cupin promoter in maize tissue. Rationale: The "theoretical" promoter sequence from maize can now be tested for function in plant material. Because it is a putative maize storage protein promoter, we will test it in embryos. Because maize transformation takes a long time, we will test it in a transient (temporary) transformation system.

Methods: Transient transformation of maize embryo tissue with the cupin family promoter:GUS gene will be performed in order to test the activity of our cupin promoter. The process begins with growing corn until it flowers, pollinating the ears, harvesting the ears at twelve days after pollination, and isolating the embryos under sterile conditions according to established protocols in the Hood lab. *A. tumefaciens* will be co-cultivated with the isolated embryos, and the embryos will be incubated for five days on plant tissue culture medium. After the five days, the embryos will be stained for GUS activity which turns any positive cells a blue color. If GUS is present, we will know that our transformation was successful and that the cupin family promoter is active in the embryo tissue. Outcome: An active test of the maize cupin promoter using a reporter gene.

Objective 4: Confirm results of transient transformation of cupin promoter:GUS activity in stable maize transformants. Rationale: Transient results are a great first test of a gene construct, but the most reliable test is making stable transformants and testing the developing or mature seeds for promoter activity.

Methods: We desire to determine if the temporary, transient transformation studies can be duplicated with a stably transformed corn plant. Immature embryos will be co-cultivated with fresh *A. tumefaciens* and in this case, the tissues will be cultivated for several months on a selective medium. A plant selective marker, herbicide resistance, will indicate whether the recombinant DNA is present in the target tissues. These experiments can be started but the results are in the future because of their long time line. Outcome: Transformed maize plants with the cupin promoter:GUS construct to determine its activity relative to GUS in seeds using a different promoter.

REFERENCES

1. Jefferson, R. A. et al. (1987) "GUS fusions: beta-glucuronidase as a sensitive and versatile gene fusion marker in higher plants," *EMBO J.* 6(13), 3901-3907.
2. Wohlleben, W. et al. (1988) "Nucleotide sequence of the phosphinothricin N-acetyltransferase gene from *Streptomyces viridochromogenes* Tu494 and its expression in *Nicotiana tabacum*," *Gene* 70(1), 25-37.
3. Nessler, C. L. (1994) "Metabolic engineering of plant secondary products," *Transgenic Res.* 3(2), 109-115.
4. Lessard, P. A. et al. (2002) "Manipulating gene expression for the metabolic engineering of plants," *Metab. Eng.* 4(1), 67-79.
5. Estruch, J. J. et al. (1997) "Transgenic plants: An emerging approach to pest control," *Nat. Biotechnol.* 15(2), 137-141.
6. Poirier, Y. et al. (1995) "Production of polyhydroxyalkanoates, a family of biodegradable plastics and elastomers, in bacteria and plants," *Nat. Biotechnol.* 13(2), 142-150.
7. Ye, X. et al. (2000) "Engineering the Provitamin A (β-Carotene) Biosynthetic Pathway into (Carotenoid-Free) Rice Endosperm," *Science* 287(5451), 303-305.
8. Weigel, D. and Nilsson, O. (1995) "A developmental switch sufficient for flower initiation in diverse plants," *Nature* 377(6549), 495-500.
9. Waterhouse, P. M. et al. (2001) "Gene silencing as an adaptive defense against viruses," *Nature* 411(6839), 834-842.
10. Yu, H. and Kumar, P. P. (2003) "Post-transcriptional gene silencing in plants by RNA," *Plant Cell Rep.* 22(3), 167-174.
11. Hood, E. E. et al. (1997) "Commercial production of avidin from transgenic maize: characterization of transformant, production, processing, extraction and purification," *Mol. Breed.* 3, 291-306.
12. Zhong, G.-Y. et al. (1999) "Commercial production of aprotinin in transgenic maize seeds," *Mol. Breed.* 5, 345-356.
13. Woodard, S. L. et al. (2003) "Maize (*Zea mays*)-derived bovine trypsin: characterization of the first large-scale, commercial protein product from transgenic plants," *Biotechnol. Appl. Biochem.* 38(Pt 2), 123-130.
14. Hood, E. E. et al. (2003) "Criteria for high-level expression of a fungal laccase gene in transgenic maize," *Plant Biotechnol. J.* 1(2), 129-140.
15. Bailey, M. R. et al. (2004) "Improved recovery of active recombinant laccase from maize seed," Appl. *Microbiol. Biotechnol.* 63(4), 390-397.
16. Mason, H. S. et al. (1992) "Expression of hepatitis B surface antigen in transgenic plants," *P.N.A.S.* 89(24), 11745-11749.
17. Haq, T. A. et al. (1995) "Oral immunization with a recombinant bacterial antigen produced in transgenic plants," *Science* 268(5211), 714-716.
18. Carrillo, C. et al. (1998) "Protective immune response to foot-and-mouth disease virus with VP1 expressed in transgenic plants," *J. Virol.* 72(2), 1688-1690.
19. Streatfield, S. J. et al. (2001) "Plant-based vaccines: unique advantages," *Vaccine* 19(17-19), 2742-2748.
20. Daniell, H. et al. (2001) "Medical molecular farming: production of antibodies, biopharmaceuticals and edible vaccines in plants," *Trends Plant Sci.* 6(5), 219-226.
21. Hood, E. E. et al. (2002) "Monoclonal antibody manufacturing in transgenic plants—myths and realities," *Curr. Opin. Biotechnol.* 13(6), 630-635.
22. Streatfield, S. et al. (2012) "Development of an edible subunit vaccine in corn against enterotoxigenic strains of *escherichia coli,*" *In Vitro Cell. Dev. Biol. Plant* 13(1), 11-17.
23. Lamphear, B. J. et al. (2002) "Delivery of subunit vaccines in maize seed," *J. Control. Release* 85(1-3), 169-180.
24. Bustos, M. M. et al. (1989) "Regulation of beta-glucuronidase expression in transgenic tobacco plants by an A/T-rich, cis-acting sequence found upstream of a French bean beta-phaseolin gene," *Plant Cell Environ.* 1(9), 839-853.
25. Leung, J. et al. (1991) "Functional analysis of cis-elements, auxin response and early developmental profiles of the mannopine synthase bidirectional promoter," *Mol. Gen. Genet.* 230(3), 463-474.
26. Guilley, H. et al. (1982) "Transcription of cauliflower mosaic virus DNA: detection of promoter sequences, and characterization of transcripts," *Cell* 30(3), 763-773.
27. Christensen, A. H. et al. (1992) "Maize polyubiquitin genes: structure, thermal perturbation of expression and transcript splicing, and promoter activity following transfer to protoplasts by electroporation," *Plant Mol. Biol* 18(4), 675-689.

28. Russell, D. A. and Fromm, M. E. (1997) "Tissue-specific expression in transgenic maize of four endosperm promoters from maize and rice," *Transgenic Res.* 6(2), 157-168.

29. Belanger, F. C. and Kriz, A. L. (1991) "Molecular basis for allelic polymorphism of the maize Globulin-1 gene," *Genetics* 129(3), 863-872.

30. De Wilde, C. et al. (2000) "Plants as bioreactors for protein production: avoiding the problem of transgene silencing," *Plant Mol. Biol* 43(2-3), 347-359.

31. Smith, T. F. and Waterman, M. S. (1981) "Comparison of biosequences," *Adv. Appl. Math.* 2(4), 482-489.

32. Needleman, S. B. and Wunsch, C. D. (1970) "A general method applicable to the search for similarities in the amino acid sequence of two proteins," *J. Mol. Biol.* 48(3), 443-453.

33. Pearson, W. R. and Lipman, D. J. (1988) "Improved tools for biological sequence comparison," *P.N.A.S.* 85(8), 2444-2448.

34. Anderson, M. L. M. and Young, B. D. (1985) "Quantitative Filter Hybridization," in *Nucleic Acid Hybridisation: A Practical Approach* (Hames, B. D. and Higgins, S. J., Eds.), pp 73-111, Oxford University Press, USA.

35. Kacian, D. L. et al. (1972) "A Replicating RNA Molecule Suitable for a Detailed Analysis of Extracellular Evolution and Replication," *Proc. Natl. Acad. Sci. U.S.A* 69(10), 3038-3042.

36. Chamberlin, M. et al. (1970) "New RNA Polymerase from *Escherichia coli* infected with Bacteriophage T7," *Nature* 228(5268), 227-231.

37. Wu, D. Y. and Wallace, R. B. (1989) "The ligation amplification reaction (LAR)—Amplification of specific DNA sequences using sequential rounds of template-dependent ligation," *Genomics* 4(4), 560-569.

38. Erlich, H. A., (Ed.) (1989) *PCR Technology: Principles and Applications for DNA Amplification*, Stockton Press, New York.

39. Mullis, K. B. et al. "Process for amplifying, detecting, and/or-cloning nucleic acid sequences," U.S. Pat. No. 4,683,195, application Ser. No. 06/828,144, filed Feb. 7, 1986. (issued Jul. 28, 1987).

40. Mullis, K. B. "Process for amplifying nucleic acid sequences," U.S. Pat. No. 4,683,202, application Ser. No. 06/791,308, filed Oct. 25, 1985. (issued Jul. 28, 1987).

41. Mullis, K. B. et al. "Process for amplifying, detecting, and/or cloning nucleic acid sequences using a thermostable enzyme," U.S. Pat. No. 4,965,188, application Ser. No. 07/063,647, filed Jun. 17, 1987. (issued Oct. 23, 1990).

42. Maniatis, T. et al. (1987) "Regulation of inducible and tissue-specific gene expression," *Science* 236(4806), 1237-1245.

43. Voss, S. D. et al. (1986) "The role of enhancers in the regulation of cell-type-specific transcriptional control," *Trends Biochem. Sci.* 11(7), 287-289.

44. Fraley, R. T. et al. "Plant proteins, promoters, coding sequences and use," U.S. Pat. No. 5,352,605, application Ser. No. 08/146,621, filed Oct. 27, 1993. (issued Oct. 4, 1994).

45. Gelvin, S., B. et al. "Chimeric Regulatory Regions and Gene Cassettes for Expression of Genes in Plants," WIPO PCT Patent Publication Number WO/1995/014098, Application PCT/US1994/012946, filed Nov. 17, 1994. (published May 26, 1995).

46. Garbarino, J. E. and Belknap, W. R. (1994) "Isolation of a ubiquitin-ribosomal protein gene (ubi3) from potato and expression of its promoter in transgenic plants," *Plant Mol. Biol* 24(1), 119-127.

47. Sambrook, J. et al. (1989) in *Molecular Cloning: A Laboratory Manual* (Sambrook, J., et al., Eds.) 2nd ed., pp 16.07-16.08, Cold Spring Harbor Laboratory Press, New York.

48. Graham, F. L. and van der Eb, A. J. (1973) "A new technique for the assay of infectivity of human adenovirus 5 DNA," *Virology* 52(2), 456-467.

49. Mccabe, D. E. "Gas driven gene delivery instrument," U.S. Pat. No. 5,584,807, application Ser. No. 08/376,319, filed Jan. 20, 1995. (issued Dec. 17, 1996).

50. de Wet, J. R. et al. (1987) "Firefly luciferase gene: structure and expression in mammalian cells," *Mol. Cell. Biol.* 7(2), 725-737.

51. Hirokawa, K. et al. "Mutant-type bioluminescent protein, and process for producing the mutant-type bioluminescent protein," U.S. Pat. No. 6,074,859, application Ser. No. 09/111,752, filed Jul. 8, 1998. (issued Jun. 13, 2000).

52. Szalay, A. A. et al. "Construction and expression of renilla luciferase and green fluorescent protein fusion genes," U.S. Pat. No. 5,976,796, application Ser. No. 08/771,850, filed Dec. 23, 1996. (issued Nov. 2, 1999).

53. Deluca, M. et al. "DNA sequences encoding coleoptera luciferase activity," U.S. Pat. No. 5,674,713, application Ser. No. 08/460,214, filed Jun. 2, 1995. (issued Oct. 7, 1997).

54. Scheirer, W. "Bioluminescence measurement system," U.S. Pat. No. 5,618,682, application Ser. No. 08/193,679, filed Feb. 8, 1994. (issued Apr. 8, 1997).

55. Sambrook, J. et al. (1989) "Synthesis of Single-stranded RNA Proves by In Vitro Transcription," in *Molecular Cloning: A Laboratory Manual* (Sambrook, J., et al., Eds.) 2nd ed., pp 9.31-.58, Cold Spring Harbor Laboratory Press, New York.

56. Sambrook, J. et al. (1989) "Transfer and Fixation of Denatured RNA to Membranes," in *Molecular Cloning: A Laboratory Manual* (Sambrook, J., et al., Eds.) 2nd ed., pp 7.39-.52, Cold Spring Harbor Laboratory Press, New York.

57. Clough, R. C. et al. (2006) "Manganese peroxidase from the white-rot fungus *Phanerochaete chrysosporium* is enzymatically active and accumulates to high levels in transgenic maize seed," *Plant Biotechnol. J.* 4(1), 53-62.

58. Hood, E. E. et al. (2007) "Subcellular targeting is a key condition for high-level accumulation of cellulase protein in transgenic maize seed," *Plant Biotechnol. J.* 5(6), 709-719.

59. Armstrong, C. et al. (1991) "Development and availability of germplasm with high type II culture formation response," *Maize Genet Coop Newsletter* 13, 92-93.

60. Hood, E. E. et al. (2012) "Manipulating corn germplasm to increase recombinant protein accumulation," *Plant Biotechnol. J.* 10(1), 20-30.

61. McCarty, D. R. (1995) "Genetic control and integration of maturation and germination pathways in seed development," *Annu. Rev. Plant Physiol. Plant Mol. Biol.* 13, 71-93.

62. Coleman, C. E. et al. (2012) "The Maize [gamma]-Zein Sequesters [alpha]-Zein and Stabilizes Its Accumulation in Protein Bodies of Transgenic Tobacco Endosperm," *Plant Cell* 13(12), 2335-2345.

63. Kiesselbach, T. A. (1949) "The Structure and Reproduction of Corn," *Res. Bull. Nebr. Agric. Exp. Sta.*, 96.

64. Kriz, A. (1989) "Characterization of embryo globulins encoded by the maizeGlb genes," *Biochem. Genet.* 27(3-4), 239-251.
65. Woo, Y. M. et al. (2001) "Genomics analysis of genes expressed in maize endosperm identifies novel seed proteins and clarifies patterns of zein gene expression," *Plant Cell* 13(10), 2297-2317.
66. Nakashima, K. et al. (2006) "Transcriptional regulation of ABI3- and ABA-responsive genes including RD29B and RD29A in seeds, germinating embryos, and seedlings of *Arabidopsis,*" *Plant Mol. Biol* 60(1), 51-68.
67. Lee, J.-M. et al. (2002) "DNA array profiling of gene expression changes during maize embryo development," *Funct. Integr. Genomics* 2(1-2), 13-27.
68. Vernoud, V. et al. (2005) "Maize Embryogenesis," *Maydica* 13.
69. Alexandrov, N. N. et al. (2009) "Insights into corn genes derived from large-scale cDNA sequencing," *Plant Mol. Biol* 69(1-2), 179-194.
70. Zhang, L. et al. (2009) "A genome-wide characterization of microRNA genes in maize," *PLoS Genet.* 5(11), e1000716.
71. Armstrong, M. F. "Inbred Corn Line Lh244," U.S. Pat. No. 6,252,148, application Ser. No. 09/455,440, filed Dec. 6, 1999. (issued Jun. 26, 2001).
72. Mortazavi, A. et al. (2008) "Mapping and quantifying mammalian transcriptomes by RNA-Seq," *Nat. Meth.* 5(7), 621-628.
73. Gideon, G. and Larkins, B. A. (1995) "Endoreduplication in Maize Endosperm: Involvement of M Phase-Promoting Factor Inhibition and Induction of S Phase-Related Kinases," *Science* 269(5228), 1262-1264.
74. Kowles, R. V. and Phillips, R. L. (1985) "DNA amplification patterns in maize endosperm nuclei during kernel development," *P.N.A.S.* 82(20), 7010-7014.
75. Girke, T. et al. (2000) "Microarray analysis of developing *Arabidopsis* seeds," *Plant Physiol.* 124(4), 1570-1581.
76. Herman, E. M. and Larkins, B. A. (1999) "Protein storage bodies and vacuoles," *Plant Cell* 11(4), 601-614.
77. Ohlrogge, J. and Browse, J. (1995) "Lipid biosynthesis," *Plant Cell* 7(7), 957-970.
78. Li, P. et al. (2010) "The developmental dynamics of the maize leaf transcriptome," *Nat. Genet.* 42(12), 1060-1067.
79. Hayano-Kanashiro, C. et al. (2009) "Analysis of gene expression and physiological responses in three Mexican maize landraces under drought stress and recovery irrigation," *PLoS. ONE* 4(10), e7531.
80. Usadel, B. et al. (2009) "A guide to using MapMan to visualize and compare Omics data in plants: a case study in the crop species, Maize," *Plant Cell Environ.* 32(9), 1211-1229.
81. Wilcoxon, F. (1945) "Individual Comparisons by Ranking Methods," *Biom. Bull.* 13(6), 80-83.
82. Bowman, V. B. et al. (1988) "Expression of lipid body protein gene during maize seed development. Spatial, temporal, and hormonal regulation," *J. Biol. Chem.* 263 (3), 1476-1481.
83. Kader, J. C. (1990) "Intracellular transfer of phospholipids, galactolipids, and fatty acids in plant cells," *Subcell. Biochem.* 16, 69-111.
84. Pla, M. et al. (1991) "Regulation of the abscisic acid-responsive gene rab28 in maize viviparous mutants," *Mol. Gen. Genet.* 230(3), 394-400.
85. Thomann, E. B. et al. (1992) "Accumulation of Group 3 Late Embryogenesis Abundant Proteins in *Zea mays* Embryos: Roles of Abscisic Acid and the Viviparous-1 Gene Product," *Plant Physiol.* 99(2), 607-614.
86. Bhattramakki, D. and Rafalsk, A. (2001) "Discovery and Application of Single Nucleotide Polymorphism Markers in Plants," in *Plant Genotyping: The DNA Fingerprinting of Plants* (R J, H., Ed.), pp 179-192, CABI Publishing, Wallingford.
87. Luo, M. et al. (2008) "Characterization of gene expression profiles in developing kernels of maize (*Zea mays*) inbred Tex6," *Plant Breed.* 13(6), 569-578.
88. Davidson, R. M. et al. (2011) "Utility of RNA Sequencing for Analysis of Maize Reproductive Transcriptomes," *Plant Genetics* 13(3), 191-203.
89. Baker, J. et al. (1988) "Sequence and characterization of 6 Lea proteins and their genes from cotton," *Plant Mol. Biol* 13(3), 277-291.
90. Dure, L. et al. (1989) "Common amino acid sequence domains among the LEA proteins of higher plants," *Plant Mol. Biol* 13(5), 475-486.
91. Wu, T. D. and Nacu, S. (2010) "Fast and SNP-tolerant detection of complex variants and splicing in short reads," *Bioinformatics* 26(7), 873-881.
92. Thimm, O. et al. (2004) "MAPMAN: a user-driven tool to display genomics data sets onto diagrams of metabolic pathways and other biological processes," *Plant J.* 37(6), 914-939.
93. Thorvaldsdóttir, H. et al. (2013) "Integrative Genomics Viewer (IGV): high-performance genomics data visualization and exploration," *Brief Bioinform.* 14(2), 178-192.
94. Robinson, M. D. and Oshlack, A. (2010) "A scaling normalization method for differential expression analysis of RNA-seq data," *Genome Biol.* 11(3), R25.
95. Benjamini, Y. and Hochberg, Y. (1995) "Controlling the false discovery rate: a practical and powerful approach to multiple testing," *Journal of the Royal Statistical Society. Series B (Methodological)* 57(1), 289-300.
96. Zeeberg, B. R. et al. (2005) "High-Throughput GoMiner, an 'industrial-strength' integrative gene ontology tool for interpretation of multiple-microarray experiments, with application to studies of Common Variable Immune Deficiency (CVID)," *BMC Bioinformatics* 6, 168.
97. Yang, N. S. and Russell, D. (1990) "Maize sucrose synthase-1 promoter directs phloem cell-specific expression of Gus gene in transgenic tobacco plants," *P.N.A.S.* 87(11), 4144-4148.
98. Geffers, R. et al. (2000) "Anaerobiosis-specific interaction of tobacco nuclear factors with cis-regulatory sequences in the maize GapC4 promoter," *Plant Mol. Biol* 43(1), 11-21.
99. Vilardell, J. et al. (1991) "Regulation of the maizerab17 gene promoter in transgenic heterologous systems," *Plant Mol. Biol* 17(5), 985-993.
100. Oldach, K. H. et al. (2001) "Heterologous expression of genes mediating enhanced fungal resistance in transgenic wheat," *Mol. Plant-Microbe Interact.* 14(7), 832-838.
101. Brinch-Pedersen, H. et al. (2003) "Concerted action of endogenous and heterologous phytase on phytic acid degradation in seed of transgenic wheat (*Triticum aestivum* L.)," *Transgenic Res.* 12(6), 649-659.
102. Cornejo, M.-J. et al. (1993) "Activity of a maize ubiquitin promoter in transgenic rice," *Plant Mol. Biol* 23(3), 567-581.
103. Takimoto, I. et al. (1994) "Non-systemic expression of a stress-responsive maize polyubiquitin gene (Ubi-1) in transgenic rice plants," *Plant Mol. Biol* 26(3), 1007-1012.
104. Roussell, D. L. et al. (1988) "Deletion of DNA sequences flanking an $M_r$ 19 000 zein gene reduces its 105. Sambrook, J. et al., (Eds.) (1989) *Molecular Cloning: A Laboratory Manual,* 2nd ed., Cold Spring Harbor Laboratory Press, New York.
106. Innis, M. A. et al. (1990) *PCR Protocols: A guide to methods and applications,* Academic Press, New York.
107. Innis, M. et al. (1995) *PCR Strategies,* Academic Press, New York.
108. Innis, M. et al. (1999) *PCR Applications: Protocols for Functional Genomics,* Academic Press, New York.
109. Meinkoth, J. and Wahl, G. (1984) "Hybridization of nucleic acids immobilized on solid supports," *Anal. Biochem.* 138(2), 267-284.
110. Ausubel, F. M. et al., (Eds.) (1993) *Current Protocols in Molecular Biology,* John Wiley & Sons, New York.
111. Quail, P. H. et al. "Plant Ubiquitin Promoter System," European Patent Publication Number EP0342926 A2, Application EP19890304930, filed May 16, 1989. (published Nov. 23, 1989).
112. Coruzzi, G. et al. (1984) "Tissue-specific and light-regulated expression of a pea nuclear gene encoding the small subunit of ribulose-1,5-bisphosphate carboxylase," *EMBO J.* 3(8), 1671-1679.
113. Broglie, R. et al. (1984) "Light-regulated expression of a pea ribulose-1,5-bisphosphate carboxylase small subunit gene in transformed plant cells," *Science* 224(4651), 838-843.
114. Velten, J. and Schell, J. (1985) "Selection-expression plasmid vectors for use in genetic transformation of higher plants," *Nucleic Acids Res.* 13(19), 6981-6998.
115. Odell, J. T. et al. (1985) "Identification of DNA sequences required for activity of the cauliflower mosaic virus 35S promoter," *Nature* 313(6005), 810-812.
116. Maiti, I. B. et al. (1997) "Promoter/leader deletion analysis and plant expression vectors with the figwort mosaic virus (FMV) full length transcript (FLt) promoter containing single or double enhancer domains," *Transgenic Res.* 6(2), 143-156.
117. Grdzelishvili, V. Z. et al. (2000) "Mapping of the Tobacco mosaic virus movement protein and coat protein subgenomic RNA promoters in vivo," *Virology* 275(1), 177-192.
118. Gurley, W. B. et al. (1986) "Upstream sequences required for efficient expression of a soybean heat shock gene," *Mol. Cell. Biol.* 6(2), 559-565.
119. Caddick, M. X. et al. (1998) "An ethanol inducible gene switch for plants used to manipulate carbon metabolism," *Nat. Biotechnol.* 16(2), 177-180.
120. Kishore, G. M. "Increased Starch Content In Plants," WIPO PCT Patent Publication Number WO/1991/019806, Application PCT/US1991/004036, filed Jun. 7, 1991. (published Dec. 26, 1991).
121. Gruber. (1993) "Vectors for plant transformation," in *Methods in Plant Molecular Biology and Biotechnology,* pp 89-119, CRC Press.
122. Gordon-Kamm, W. et al. (1990) "Transformation of Maize Cells and Regeneration of Fertile Transgenic Plants," *Plant Cell* 2(7), 603-618.
123. Rogers, J. C. (1985) "Two barley alpha-amylase gene families are regulated differently in aleurone cells," *J. Biol. Chem.* 260(6), 3731-3738.
124. Becker, T. W. et al. (1992) "Thecab-m7 gene: a light-inducible, mesophyll-specific gene of maize," *Plant Mol. Biol* 20(1), 49-60.
125. Fontes, E. B. et al. (1991) "Characterization of an immunoglobulin binding protein homolog in the maize floury-2 endosperm mutant," *Plant Cell Environ.* 3(5), 483-496.
126. Matsuoka, K. and Nakamura, K. (1991) "Propeptide of a precursor to a plant vacuolar protein required for vacuolar targeting," *P.N.A.S.* 88(3), 834-838.
127. Gould, S. J. et al. (1989) "A conserved tripeptide sorts proteins to peroxisomes," *J. Cell Biol.* 108(5), 1657-1664.
128. Creissen, G. et al. (1992) "Molecular characterization of glutathione reductase cDNAs from pea (*Pisum sativum* L.)," *Plant J.* 2(1), 129-131.
129. Kalderon, D. et al. (1984) "A short amino acid sequence able to specify nuclear location," *Cell* 39(3), 499-509.
130. Stiefel, V. et al. (1990) "Expression of a maize cell wall hydroxyproline-rich glycoprotein gene in early leaf and root vascular differentiation," *Plant Cell* 2(8), 785-793.
131. Elroy-Stein, O. et al. (1989) "Cap-independent translation of mRNA conferred by encephalomyocarditis virus 5' sequence improves the performance of the vaccinia virus/bacteriophage T7 hybrid expression system," *P.N.A.S.* 86(16), 6126-6130.
132. Gallie, D. R. et al. (1995) "The tobacco etch viral 5' leader and poly(A) tail are functionally synergistic regulators of translation," *Gene* 165(2), 233-238.
133. Macejak, D. G. and Sarnow, P. (1991) "Internal initiation of translation mediated by the 5' leader of a cellular mRNA," *Nature* 353(6339), 90-94.
134. Jobling, S. A. and Gehrke, L. (1987) "Enhanced translation of chimaeric messenger RNAs containing a plant viral untranslated leader sequence," *Nature* 325 (6105), 622-625.
135. Lommel, S. A. et al. (1991) "Identification of the Maize chlorotic mottle virus capsid protein cistron and characterization of its subgenomic messenger RNA," *Virology* 181(1), 382-385.
136. Della-Cioppa, G. et al. (1987) "Protein trafficking in plant cells," *Plant Physiol.* 84(4), 965-968.
137. Miki, B. and McHugh, S. (2004) "Selectable marker genes in transgenic plants: applications, alternatives and biosafety," *J. Biotechnol.* 107(3), 193-232.
138. Klein, T. M. et al. (1992) "Transformation of microbes, plants and animals by particle bombardment," *Nat. Biotechnol.* 10(3), 286-291.
139. Weising, K. et al. (1988) "Foreign Genes in Plants: Transfer, Structure, Expression, and Applications," *Annu. Rev. Genet.* 22, 421-477.
140. Fromm, M. et al. (1985) "Expression of genes transferred into monocot and dicot plant cells by electroporation," *P.N.A.S.* 82(17), 5824-5828.
141. Mathur, J. and Koncz, C. (1998) "PEG-Mediated Protoplast Transformation with Naked DNA," in *Arabidopsis Protocols* (Martinez-Zapater, J. and Salinas, J., Eds.), pp 267-276, Humana Press.
142. De Wet, J. M. J. "Method For The Transfer Of Exogenous Genes In Plants Using Pollen As A Vector" WIPO PCT Patent Publication Number WO/1985/001856, Application PCT/US1984/001774, filed Oct. 31, 1984. (published May 9, 1985).
143. Schilperoort, R. A. et al. "Process For The In-Vitro Transformation Of Plant Protoplasts With Plasmid Dna," U.S. Pat. No. 4,684,611, application Ser. No. 06/760,145, filed Jul. 29, 1985. (issued Aug. 4, 1987).
144. Crossway, A. et al. (1986) "Integration of foreign DNA following microinjection of tobacco mesophyll protoplasts," *Mol. Genet. Genomics* 202, 179-185.

145. Ishida, Y. et al. (1996) "High efficiency transformation of maize (*Zea mays* L.) mediated by *Agrobacterium tumefaciens*," *Nat. Biotechnol.* 14(6), 745-750.
146. Fraley, R. T. et al. (1983) "Expression of bacterial genes in plant cells," *P.N.A.S.* 80(15), 4803-4807.
147. Moloney, M. M. et al. (1989) "High efficiency transformation of *Brassica napus* using *Agrobacterium* vectors," *Plant Cell Rep.* 8(4), 238-242.
148. Rice, T. B. et al. "Methods And Compositions For The Production Of Stably Transformed, Fertile Monocot Plants And Cells Thereof," U.S. Pat. No. 5,550,318, application Ser. No. 07/565,844, filed Aug. 9, 1990. (issued Aug. 27, 1996).
149. Hiei, Y. et al. (1994) "Efficient transformation of rice (*Oryza sativa* L.) mediated by *Agrobacterium* and sequence analysis of the boundaries of the T-DNA," *Plant J.* 6(2), 271-282.
150. Lee, N. et al. (1991) "Efficient transformation and regeneration of rice small cell groups," *P.N.A.S.* 88(15), 6389-6393.
151. Casas, A. M. et al. (1993) "Transgenic sorghum plants via microprojectile bombardment," *P.N.A.S.* 90(23), 11212-11216.
152. Wan, Y. and Lemaux, P. (1994) "Generation of Large Numbers of Independently Transformed Fertile Barley Plants," *Plant Physiol.* 104(1), 37-48.
153. Christou, P. et al. "Particle-Mediated Transformation Of Soybean Plants And Lines," U.S. Pat. No. 5,015,580, application Ser. No. 07/193,357, filed May 12, 1988. (issued May 14, 1991).
154. Hiei, Y. and Komari, T. "Method For Transforming Monocotyledons," U.S. Pat. No. 5,591,616, application Ser. No. 08/193,058, filed May 3, 1994. (issued Jan. 7, 1997).
155. Armstrong, C. L. and Green, C. E. (1985) "Establishment and maintenance of friable, embryogenic maize callus and the involvement of L-proline," *Planta* 164(2), 207-214.
156. Hood, E. E. et al. (1986) "The hypervirulence of *Agrobacterium tumefaciens* A281 is encoded in a region of pTiBo542 outside of T-DNA," *J. Bacteriol.* 168(3), 1291-1301.
157. Poehlman, J. M. and Sleper, D. A. (1995) *Breeding field crops,* 4th Edition ed., Iowa State University Press.
158. Brar, G. S. and Nelson, O. "Genic Male-Sterile Maize," U.S. Pat. No. 4,654,465, application Ser. No. 06/756,746, filed Jul. 18, 1985. (issued Mar. 31, 1987).
159. Brar, G. S. and Nelson, O. "Genic Male-Sterile Maize Using A Linked Marker Gene," U.S. Pat. No. 4,727,219, application Ser. No. 06/935,976, filed Nov. 28, 1986. (issued Feb. 23, 1988).
160. Albertsen, M. C. et al. "Nucleotide Sequences Mediating Fertility And Method Of Using Same," U.S. Pat. No. 5,859,341, application Ser. No. 08/482,714, filed Jun. 7, 1995. (issued Jan. 12, 1999).
161. Fabijanski, S. F. et al. "Molecular Methods Of Hybrid Seed Production," U.S. Pat. No. 6,013,859, application Ser. No. 08/476,864, filed Jun. 7, 1995. (issued Jan. 11, 2000).

We claim:

1. An isolated DNA molecule comprising a plant regulatory element, wherein the regulatory element comprises SEQ ID NO: 3, and a heterologous gene operably linked to said regulatory element.

2. An expression vector, comprising the DNA molecule of claim 1.

3. A transgenic plant cell, comprising the DNA molecule of claim 1.

4. A transgenic plant, comprising the DNA molecule of claim 1.

5. A transgenic plant embryo, comprising the DNA molecule of claim 1.

6. A plant gene expression cassette comprising, in sequence, a regulatory element comprising SEQ ID NO: 3 operably linked to the coding region of a heterologous gene and a 3' polyadenylation signal.

7. A method for selectively expressing a nucleotide sequence in a plant embryo, the method comprising transforming a plant embryo with a transformation vector comprising an expression cassette, the expression cassette comprising a regulatory element and a heterologous nucleotide sequence operably linked to the regulatory element, said regulatory element comprising the sequence of SEQ ID NO: 3.

8. A method of producing a protein of interest in a plant embryo, comprising: a) providing a transgenic embryo comprising a heterologous nucleic acid sequence encoding the protein of interest operably linked to a regulatory element, wherein the regulatory element comprises SEQ ID NO:3; and b) growing the plant under conditions such that the protein is produced in said embryo.

9. The method of claim 8, wherein said embryo is a monocot embryo.

10. The method of claim 8, wherein said producing a protein corresponds with the embryonic stage of plant development.

* * * * *

```
                        SEQUENCE LISTING

<160> NUMBER OF SEQ ID NOS: 31

<210> SEQ ID NO 1
<211> LENGTH: 3074
<212> TYPE: DNA
<213> ORGANISM: Zea mays

<400> SEQUENCE: 1
gatatgtcct actccttgac atgcctgcgc ggtgggggag gaaagtaggt cttcaggctg      60
aagtttgtaa tttgatggtt tgttggttat cggctaactg ttttacgctt gctctaaaat     120
tagtcgttta aattaaaaaa ctaaacttag aaaaaaaaat taagtaaaat atatcaagtt     180
aagtaccaaa ttaaacattc tctcaattaa tctcaaatgg tagattttc  tgttcagtcg     240 cggtataaaa ccgtattttt taagactttt acttatttct atctctgctg attatggtat     300
taagatccct actaagtgtc caatactttc attaacttat taccaaaaat aaagtattat     360
aggtattaga aatcctctta gagtctaata ctgtctccgc tctaaaatat agttgtttct     420
agtccatttt tattatatct atatttattc aaatgataat gaatttatat atatatat      480 atatatatat atatatatat atatatatat atatatatat atatatatat atatatat      540 atatatatat aacgggagcc ctgggcttcc aatagttaaa ggaaacacag gccgaccatc     600
cctgcaaact ggttcaacca gcgcgtccaa acaggcggtc gggtgcgcca cctgccccac     660
gtctgttagc gcaaaaaaag gaatgcatgc ataagtcaaa cacgatccaa tgcatgcgca     720
taaatttagg aaagatatgt gcggcagttt ctatttttaa aatcctttat ttcctccata     780
aatttaggat cgctgcaaca gccatgcagc tagacgcgta aggaccattt tatgatatat     840
actgagacta aatatgctac actgtgttaa taattatgca attcgatata ctgcgtaaaa     900
atctgttacc agctgcatgc acacgaattt atgataaaaa atgtgcaatg aaaggaaatg     960
```

```
aattacacgc atagaaacaa aaaatcgtat ttaatgtttt atttccttca taaatataag    1020
gtccctccaa cagccatgca gctaaaacac attaaatcta gtttatgaca tatactgata    1080
caaattatac tacatggtgt aggtatttat gcaattcgtt acactgcgta aaaaatctgg    1140
catgttgttc actggtggat gcacctccgg gttggagcgt aataacctta agttttaagc    1200 ataaatccc tcaattataa gtgtatatac cgagccaatg tgagaggttg atagctctag     1260
taggttgtta ttacgatcct atttttatgg cagatccgaa aaatatggca gtcgcatgca    1320
tgcggttata cagatcctaa aattatggca aaatgcatgc atgagtcaaa cacgttccct    1380
tgcatgcgcg taaatttagg aaagatatgt gtggcggttt ctattttaaa tgctttattt    1440
cctccataaa tttaggatcg ctgcaacaga catgcaacta aaactcgtaa tgaccatttt    1500
atgctatata ctgatactaa atatgctaca ctgtgtagat aattatgcaa ttcggtatac    1560
tgcgtaaaaa tctgctacag gctgcatgca cacgaattta tgatggaaag aatatgcaat    1620
gaaaggaaat gaattgcatg catagaaaca aaaaatcata tttaatattt taattttgct    1680
tcctaaatat aggatccctc caacagccat gcaaatataa cgcattagaa ctagtttatg    1740
atgtatactg aaacaaatta taatacacgg tgtaggtatt tatgcaattc cttacaaagc    1800
gtaaaaaatc tggcatgttg ttcactggtg gacgcatctc cgggtggagc gtaaaaacct    1860
taagttttga gcataaaatc cctcaattat aagcataaat accgagtcaa ttagaggttg    1920
atagctttag taggttgtta ttacgatcct attttatga cagatccgaa aaacatggca     1980
gccgcatgca tgcggtttct gtcgggacc ataattaggg gtaccctcaa gacgcctaat     2040
tctcagctgg taaccccat cagcataaag ctgcagaggc ctgatgggtg cgattaagtc      2100
agggatcagt ccatacgagc gactcgatca cgcctcgccc gagcctagcc tcgggcaagg    2160
gcagccgacc ccgagggggtt tccgtctcgc ccgaggcccc cctttttaac ggcggacaca    2220
tctccggctc gcccgaggcc ttggcttcgc taagaagcaa ccctgactaa atcgccgcgc    2280
cgaccgaccg agtcgcaggg gcatttaacg caaaggtggc ctgacacctt tatcctgaca    2340
cgcgccctcc ggcagagccg aagtgaccgc cgtcacttcg ccgctccact gactggtctg    2400
acagaaggac agcgccgcct gcgccactcc gactgcagcg ccacttgaca gagtgatgct    2460
gacaggaagc caggccttgc caaaggcgcc ataggaagct ccgcccgacc cagggctcgg    2520
actcgggcta agcctcggaa gacggcgaac tccgctccgc ccgacccagg gctcggactc    2580
gggctaagcc ccggaagacg gcgaactccg ctccgcccga cccagggctc gcactcgggc    2640
taaggccccg gaagacggcg aactccgctc cgcccgaccc agggctcgga ctcgggctaa    2700
ggccccggaa gacggcgaac tccgctccgc cgacccagg gctcggactc aggctaaggc     2760
cccggaagac ggcgaactcc actccgcccg acccagggct cggactcggg ctcagcccca    2820
gaagacgacg aactccgctc cgcccgaccc agggctcgg actcgggcta agacccggaa     2880
gacgacgaac tccgcttcgc ccgacccag ggctcggact ccgccgggc ctctgccgaa      2940 cgatctccgc cttgcccgac ccgggggctc ggcctcggcc tcggccacgg aagacagact    3000
cgaccctggc ttcggaggag ccccacgtc gcccgaccta gggcacaggc ccgccacgtc     3060
aacaggaagc gcca                                                       3074
```

<210> SEQ ID NO 2
<211> LENGTH: 1893
<212> TYPE: DNA
<213> ORGANISM: Zea mays

<400> SEQUENCE: 2

```
atggcggtgg cgacgactgc tcggtggctc ctgctcctgg ctgtcgtctc ggcggccgcg        60
gcgtccggga agcacgagag gtggagggtg ggcggccagg tggtggagaa ggagcgacgg       120
cgggtggtgg cggagagcga ggccggctcg gtctcggccg tggacgtcgc cgacgcggcg       180
ggcacggcgt accggctgca cttcatcacc atggaccccg gggcgctgtt cctgcccgtg       240
cagctgcatg ccgacatggt gttctacgtt cacagcgggc ggggcaaggt gacttccata       300
gaagaagaga gcagcgaaca gagctccctg gaggtggagc gaggagacgt atacaacttt       360
gagcagggga gcatcctgta catccagagc taccccaacg ccagtagaca gcgtcttcgg       420
atctacgcca tcttcaccag cgaaggcatc aacgccgatg accctcgaa gcccaaggtg        480
gaagcttact ccagcgtcag caatctggtc aaagggttcg agacagacgt tcttcgcctg       540
ggatttgggg tcaaacccga ggtggtagaa gcgatcaagt ctgccaagac accgccaccg       600
atcatagcct acaacccaga ggaggagaag gggacaagaa acccggctg gaccgagaac        660
atcatcgacg ctctgctggg cgtgcgcgat ccggaggagt ccttaacaa gaagaagaag        720
aagaaggaca gcacaaggaa caagaagtcc aagagcaagg cgttcaactt ctactccgga       780
aagccagacg tccagaactg ctacggtgg agccggatga tgactagcaa ggacctcgac        840
gcgctgcacg gatccagcat tggcatgttc atggtgaacc tgactacggg ttcgatgatg       900
gggcctcact ggaaccccaa ggccacggag atcgccatcg tgacagaggg ttcaggaatc       960
gtgcagacgg tgtgcccgag cagcagcagc agcagcagca gcccgtcggg cgggagcagt      1020
ggagaccacc accacggtca aagcggcgc ggcgggccgg gaggccgcgg cgatgagggc        1080
gaaggcgaag gcggccgcgc gcggtggcag tgcaggaact cggtgttccg tgtgaaggaa       1140
ggcgacgtct tcgtggtgcc gcggttccac ccgatggcgc agatgtcgtt caacgacgac       1200
tcgttcgtgt tcgtcgggtt cagcacccac atggggcaaa accaccgca gttcctggcc       1260
gggaagggct ccgtgctgca ggccattggg aagaaggtgc tggcgctggc gctggggcag       1320
cgggacccga ccgccgtgga caagctgctg tccgcgcagc gcgagtcgac gatactgccg       1380
tgcgtatcgt gcgctgagga gctggcgag aaggccgagg aggagaggaa gcgacggag         1440
gaggaagggg gagggaaagg gaaaggaccg ggagaacgtg agaaggaaaa ggagaggagg       1500
gaacggagg agaaggaaaa ggaggaagag cgggagaggg aacggaagga aaggagagg        1560
aaggaaaggg aacgggagga aaggagagg aaggaaaggg aacgggagga agaagagagg        1620
agggaagagg aagaagagcg ggccaggaag gagcaagaga agcagcggag gagagagaaa       1680
gaggaggagg agcgtgcacg gagacgcgag gaggaagaaa gagagaggga ggaggaagaa       1740
gaacggcgga gggaggagga agaaggtgga ggcggacgtg gtgacgagcc agagagggag       1800
gaagaaggcg gtgacaagcc gccataccgg ttgtccaaga aactgaagaa acgctaccat       1860
gcacgtgccg gtgtgttcag caggagtggc tga                                   1893
```

<210> SEQ ID NO 3
<211> LENGTH: 2500
<212> TYPE: DNA
<213> ORGANISM: Zea mays

<400> SEQUENCE: 3

```
gatatgtcct actccttgac atgcctgcgc ggtgggggag gaaagtaggt cttcaggctg        60
aagtttgtaa tttgatggtt tgttggttat cggctaactg ttttacgctt gctctaaaat       120
tagtcgttta aattaaaaaa ctaaacttag aaaaaaaaat taagtaaaat atatcaagtt       180
```

```
aagtaccaaa ttaaacattc tctcaattaa tctcaaatgg tagattttc tgttcagtcg      240 cggtataaaa ccgtattttt taagactttt acttatttct atctctgctg attatggtat     300
taagatccct actaagtgtc caatactttc attaacttat taccaaaaat aaagtattat     360
aggtattaga atcctctta gagtctaata ctgtctccgc tctaaaatat agttgtttct      420
agtccatttt tattatatct atatttattc aaatgataat gaatttatat atatatatat    480
atatatatat atatatatat atatatatat atatatatat atatatatat atatatatat    540
atatatatat aacgggagcc ctgggcttcc aatagttaaa ggaaacacag gccgaccatc    600
cctgcaaact ggttcaacca gcgcgtccaa acaggcggtc gggtgcgcca cctgccccac   660
gtctgttagc gcaaaaaaag gaatgcatgc ataagtcaaa cacgatccaa tgcatgcgca   720
taaatttagg aaagatatgt gcggcagttt ctattttaa atcctttat ttcctccata    780 aatttaggat cgctgcaaca gccatgcagc tagacgcgta aggaccattt tatgatatat   840
actgagacta aatatgctac actgtgttaa taattatgca attcgatata ctgcgtaaaa   900
atctgttacc agctgcatgc acacgaattt atgataaaaa atgtgcaatg aaaggaaatg   960
aattacacgc atagaaacaa aaaatcgtat ttaatgtttt atttccttca taaatataag   1020
gtccctccaa cagccatgca gctaaaacac attaaatcta gtttatgaca tatactgata   1080
caaattatac tacatggtgt aggtatttat gcaattcgtt acactgcgta aaaaatctgg   1140
catgttgttc actggtggat gcacctccgg gttggagcgt ataaccctta agttttaagc   1200
ataaaatccc tcaattataa gtgtatatac cgagccaatg tgagaggttg atagctctag   1260
taggttgtta ttacgatcct attttttatgg cagatccgaa aaatatggca gtcgcatgca   1320 tgcggtttata cagatcctaa aattatggca aaatgcatgc atgagtcaaa cacgttccct   1380
tgcatgcgcg taaatttagg aaagatatgt gtggcggttt ctattttaaa tgctttattt   1440
cctccataaa tttaggatcg ctgcaacaga catgcaacta aaactcgtaa tgaccatttt   1500
atgctatata ctgatactaa atatgctaca ctgtgtagat aattatgcaa ttcggtatac   1560
tgcgtaaaaa tctgctacag gctgcatgca cacgaattta tgatggaaag aatatgcaat   1620
gaaaggaaat gaattgcatg catagaaaca aaaaatcata tttaatattt taattttgct   1680
tcctaaatat aggatccctc caacagccat gcaaatataa cgcattagaa ctagtttatg   1740
atgtatactg aaacaaatta taatacacgg tgtaggtatt tatgcaattc cttacaaagc   1800
gtaaaaaatc tggcatgttg ttcactggtg gacgcatctc cgggtggagc gtaaaaacct   1860 taagtttga gcataaaatc cctcaattat aagcataaat accgagtcaa ttagaggttg   1920
atagctttag taggttgtta ttacgatcct attttttatga cagatccgaa aaacatggca   1980
gccgcatgca tgcggtttct gtcggggacc ataattaggg gtaccctcaa gacgcctaat   2040
tctcagctgg taacccccat cagcataaag ctgcagaggc ctgatgggtg cgattaagtc   2100
agggatcagt ccatacgagc gactcgatca cgcctcgccc gagcctagcc tcgggcaagg   2160
gcagccgacc ccgagggggtt tccgtctcgc ccgaggcccc ccttttaac ggcggacaca    2220 tctccggctc gcccgaggcc ttggcttcgc taagaagcaa ccctgactaa atcgccgcgc   2280
cgaccgaccg agtcgcaggg gcatttaacg caaaggtggc ctgacacctt tatcctgaca   2340
cgcgccctcc ggcagagccg aagtgaccgc cgtcacttcg ccgctccact gactggtctg   2400
acagaaggac agcgccgcct gcgccactcc gactgcagcg ccacttgaca gagtgatgct   2460
gacaggaagc caggccttgc caaaggcgcc ataggaagct                          2500
```

```
<210> SEQ ID NO 4
<211> LENGTH: 19
<212> TYPE: DNA
<213> ORGANISM: Artificial sequence
<220> FEATURE:
<223> OTHER INFORMATION: synthetic

<400> SEQUENCE: 4
tccaataatt cgtaaccat                                               19

<210> SEQ ID NO 5
<211> LENGTH: 18
<212> TYPE: DNA
<213> ORGANISM: Artificial sequence
<220> FEATURE:
<223> OTHER INFORMATION: synthetic

<400> SEQUENCE: 5
cactcacaga tagtaacc                                                18

<210> SEQ ID NO 6
<211> LENGTH: 19
<212> TYPE: DNA
<213> ORGANISM: Artificial sequence
<220> FEATURE:
<223> OTHER INFORMATION: synthetic

<400> SEQUENCE: 6
gatgctgaga ggagggatt                                               19

<210> SEQ ID NO 7
<211> LENGTH: 18
<212> TYPE: DNA
<213> ORGANISM: Artificial sequence
<220> FEATURE:
<223> OTHER INFORMATION: synthetic

<400> SEQUENCE: 7
ccattgttgc caccactc                                                18

<210> SEQ ID NO 8
<211> LENGTH: 18
<212> TYPE: DNA
<213> ORGANISM: Artificial sequence
<220> FEATURE:
<223> OTHER INFORMATION: synthetic

<400> SEQUENCE: 8
gatggatgga cagtgaag                                                18

<210> SEQ ID NO 9
<211> LENGTH: 18
<212> TYPE: DNA
<213> ORGANISM: Artificial sequence
<220> FEATURE:
<223> OTHER INFORMATION: synthetic

<400> SEQUENCE: 9
agcagaacaa gaacaaca                                                18

<210> SEQ ID NO 10
<211> LENGTH: 18
<212> TYPE: DNA
<213> ORGANISM: Artificial sequence
<220> FEATURE:
<223> OTHER INFORMATION: synthetic
```

<400> SEQUENCE: 10
cttcaccttc cacttcaa                                            18

<210> SEQ ID NO 11
<211> LENGTH: 19
<212> TYPE: DNA
<213> ORGANISM: Artificial sequence
<220> FEATURE:
<223> OTHER INFORMATION: synthetic

<400> SEQUENCE: 11 aatgggtaa aagcaaaag                                            19

<210> SEQ ID NO 12
<211> LENGTH: 19
<212> TYPE: DNA
<213> ORGANISM: Artificial sequence
<220> FEATURE:
<223> OTHER INFORMATION: synthetic

<400> SEQUENCE: 12
gcgagttcca gttcttctt                                           19

<210> SEQ ID NO 13
<211> LENGTH: 18
<212> TYPE: DNA
<213> ORGANISM: Artificial sequence
<220> FEATURE:
<223> OTHER INFORMATION: synthetic

<400> SEQUENCE: 13
tcttgtacgc agctctct                                            18

<210> SEQ ID NO 14
<211> LENGTH: 19
<212> TYPE: DNA
<213> ORGANISM: Artificial sequence
<220> FEATURE:
<223> OTHER INFORMATION: synthetic

<400> SEQUENCE: 14
aatgtgaaga gtccagtgg                                           19

<210> SEQ ID NO 15
<211> LENGTH: 18
<212> TYPE: DNA
<213> ORGANISM: Artificial sequence
<220> FEATURE:
<223> OTHER INFORMATION: synthetic

<400> SEQUENCE: 15
cgtcctcagg tgatgatg                                            18

<210> SEQ ID NO 16
<211> LENGTH: 22
<212> TYPE: DNA
<213> ORGANISM: Artificial sequence
<220> FEATURE:
<223> OTHER INFORMATION: synthetic

<400> SEQUENCE: 16
gcatacaaga gcaacaagat ac                                       22

<210> SEQ ID NO 17

<211> LENGTH: 18
<212> TYPE: DNA
<213> ORGANISM: Artificial sequence
<220> FEATURE:
<223> OTHER INFORMATION: synthetic

<400> SEQUENCE: 17
aagagtgtgg cgagtagt                                              18

<210> SEQ ID NO 18
<211> LENGTH: 20
<212> TYPE: DNA
<213> ORGANISM: Artificial sequence
<220> FEATURE:
<223> OTHER INFORMATION: synthetic

<400> SEQUENCE: 18
tgcctccaca cggttatcac                                            20

<210> SEQ ID NO 19
<211> LENGTH: 23
<212> TYPE: DNA
<213> ORGANISM: Artificial sequence
<220> FEATURE:
<223> OTHER INFORMATION: synthetic

<400> SEQUENCE: 19
gatgctcatt cttgccttgt tgt                                        23

<210> SEQ ID NO 20
<211> LENGTH: 21
<212> TYPE: DNA
<213> ORGANISM: Artificial sequence
<220> FEATURE:
<223> OTHER INFORMATION: synthetic

<400> SEQUENCE: 20
gggacattaa accagagaat c                                          21

<210> SEQ ID NO 21
<211> LENGTH: 20
<212> TYPE: DNA
<213> ORGANISM: Artificial sequence
<220> FEATURE:
<223> OTHER INFORMATION: synthetic

<400> SEQUENCE: 21
gaactcatag cacagaacac                                            20

<210> SEQ ID NO 22
<211> LENGTH: 18
<212> TYPE: DNA
<213> ORGANISM: Artificial sequence
<220> FEATURE:
<223> OTHER INFORMATION: synthetic

<400> SEQUENCE: 22
gtgcgagttt gtatgaat                                              18

<210> SEQ ID NO 23
<211> LENGTH: 18
<212> TYPE: DNA
<213> ORGANISM: Artificial sequence
<220> FEATURE:
<223> OTHER INFORMATION: synthetic

<400> SEQUENCE: 23

```
aactacacct ctgaactg                                         18

<210> SEQ ID NO 24
<211> LENGTH: 20
<212> TYPE: DNA
<213> ORGANISM: Artificial sequence
<220> FEATURE:
<223> OTHER INFORMATION: synthetic

<400> SEQUENCE: 24
atccagagct accccaacgc                                       20

<210> SEQ ID NO 25
<211> LENGTH: 20
<212> TYPE: DNA
<213> ORGANISM: Artificial sequence
<220> FEATURE:
<223> OTHER INFORMATION: synthetic

<400> SEQUENCE: 25
cttgggcttc gagggtcat                                        20

<210> SEQ ID NO 26
<211> LENGTH: 18
<212> TYPE: DNA
<213> ORGANISM: Artificial sequence
<220> FEATURE:
<223> OTHER INFORMATION: synthetic

<400> SEQUENCE: 26
gcccgttatg atgagatt                                         18

<210> SEQ ID NO 27
<211> LENGTH: 18
<212> TYPE: DNA
<213> ORGANISM: Artificial sequence
<220> FEATURE:
<223> OTHER INFORMATION: synthetic

<400> SEQUENCE: 27
agagatggga acaaagtg                                         18

<210> SEQ ID NO 28
<211> LENGTH: 24
<212> TYPE: DNA
<213> ORGANISM: Artificial sequence
<220> FEATURE:
<223> OTHER INFORMATION: synthetic

<400> SEQUENCE: 28
aattgcgttg ttacttaatg tgta                                  24

<210> SEQ ID NO 29
<211> LENGTH: 18
<212> TYPE: DNA
<213> ORGANISM: Artificial sequence
<220> FEATURE:
<223> OTHER INFORMATION: synthetic

<400> SEQUENCE: 29
cctccgactt ggacttgt                                         18

<210> SEQ ID NO 30
<211> LENGTH: 19
<212> TYPE: DNA
```

```
<213> ORGANISM: Artificial sequence
<220> FEATURE:
<223> OTHER INFORMATION: synthetic

<400> SEQUENCE: 30
gcttgctgac tacaacatc                                                19

<210> SEQ ID NO 31
<211> LENGTH: 18
<212> TYPE: DNA
<213> ORGANISM: Artificial sequence
<220> FEATURE:
<223> OTHER INFORMATION: synthetic

<400> SEQUENCE: 31
ccttgtcctg gatcttgg                                                 18
```